United States Patent
Fujii et al.

[11] Patent Number: 5,594,768
[45] Date of Patent: Jan. 14, 1997

[54] LAMINOGRAPH AND INSPECTION AND REPAIR DEVICE USING THE SAME

[75] Inventors: Masashi Fujii; Kiichiro Uyama; Takeo Tsuchiya, all of Tokyo; Miki Mori, Kanagawa-ken; Hideo Kosuge, Chiba-ken; Hirokatsu Suzuki, Tokyo, all of Japan

[73] Assignee: Kabushiki Kaisha Toshiba, Kawasaki, Japan

[21] Appl. No.: 439,106

[22] Filed: May 11, 1995

[30] Foreign Application Priority Data

May 12, 1994 [JP] Japan ................................. 6-097796
Aug. 10, 1994 [JP] Japan ................................. 6-188297

[51] Int. Cl.⁶ .................................................. G01N 23/04
[52] U.S. Cl. ............................................. 378/21; 378/58
[58] Field of Search .................................. 378/21, 22, 23, 378/24, 25, 26, 58, 146

[56] References Cited

U.S. PATENT DOCUMENTS

| | | | |
|---|---|---|---|
| H1,495 | 10/1995 | Kirchner et al. | 378/21 X |
| 4,667,403 | 5/1987 | Edinger et al. | |
| 4,926,452 | 5/1990 | Baker et al. | |
| 5,081,656 | 1/1992 | Baker et al. | 378/21 |
| 5,388,136 | 2/1995 | Halliday et al. | 378/21 X |
| 5,461,653 | 10/1995 | Parker | 378/21 X |

FOREIGN PATENT DOCUMENTS

| | | |
|---|---|---|
| 0577414 | 1/1994 | European Pat. Off. |
| 4-238162 | 4/1907 | Japan |
| 6-097791 | 6/1912 | Japan |
| 4-184258 | 4/1913 | Japan |
| 3-337460 | 3/1920 | Japan |
| 6-198571 | 6/1923 | Japan |
| 6-199313 | 6/1924 | Japan |
| 5-299197 | 5/1930 | Japan |
| 61-154645 | 7/1986 | Japan |
| 63-157046 | 6/1988 | Japan |
| 2-501411 | 5/1990 | Japan |
| 3-10151 | 1/1991 | Japan |
| 4-210049 | 7/1992 | Japan |
| 5-157708 | 6/1993 | Japan |
| WO89/04477 | 5/1989 | WIPO |
| WO92/04620 | 3/1992 | WIPO |

OTHER PUBLICATIONS

Materials Evaluation, vol. 48, May 1990, pp. 618–622, S. F. Buchele, et al., "Forming Laminograms on Object–Dependent Surfaces".

Bio–Imaging Research, Inc., p. 6, "Industry's New Vision Computed Tomography and Other Imaging Techniques" No date.

*Primary Examiner*—David P. Porta
*Attorney, Agent, or Firm*—Oblon, Spivak, McClelland, Maier & Neustadt, P.C.

[57] ABSTRACT

A laminograph including, a radiation source for generating radiation towards a subject, a radiation surface sensor device with a two-dimensional resolution, fitted opposite to the radiation source for detecting the radiation from the radiation source which has passed through the subject, a scanning device for moving the subject to take a plurality of different positions between the radiation source and the radiation surface sensor device and for scanning the subject in each of the different positions by the radiation from the radiation source. The laminograph further includes a data collection device for collecting the plurality of outputs of the radiation surface sensor device during the scanning by the scanning device to obtain the plurality of radiographic images of the subject in the different positions, a position measurement device for measuring multiple positions of a focal plane at multiple places of the subject, a displacement measurement device for measuring multiple displacement based on the multiple positions of the focal plane measured by the position measurement device, and an image processing device for adding and averaging the plurality of radiographic images with the displacements to obtain a radiographic image of the subject focused on the focal plane as a tomographic image of the subject.

38 Claims, 44 Drawing Sheets

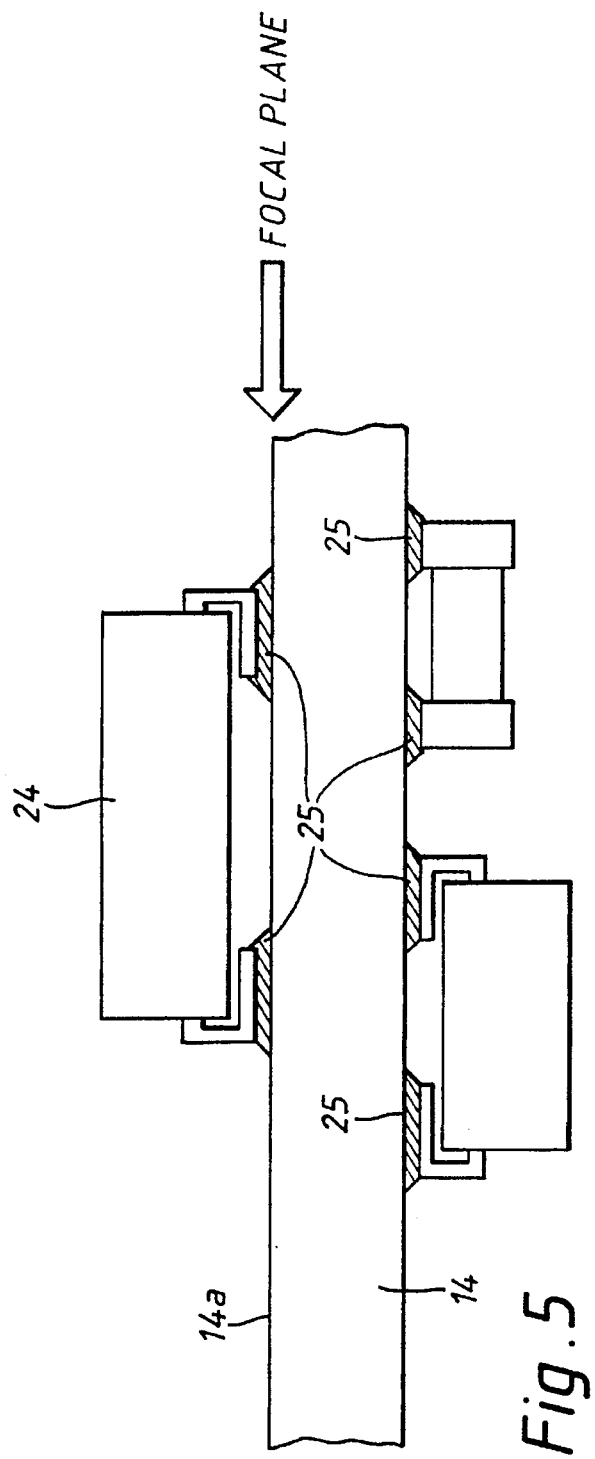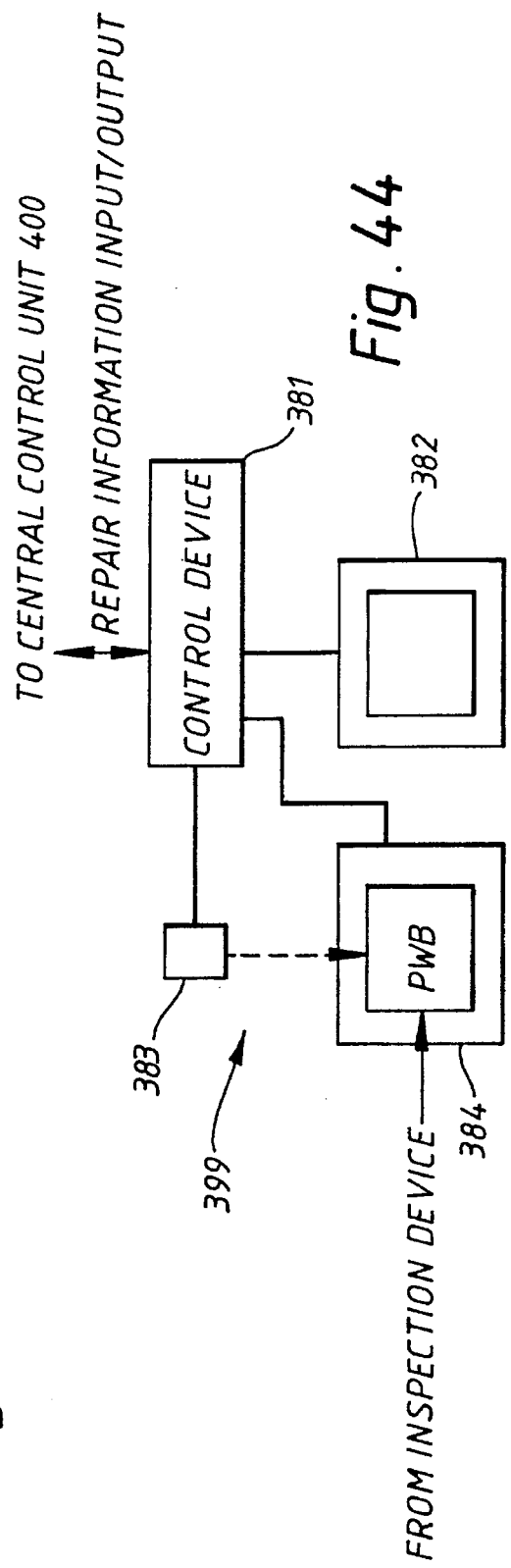

Fig.10(a)

| (Q No.) | COORDINATES | SURFACE HEIGHT |
|---|---|---|
| 1, | $X_1, Y_1,$ | $L_1$ |
| 2, | $X_2, Y_2,$ | $L_2$ |
| 3, | $X_3, Y_3,$ | $L_3$ |
| 4, | $X_4, Y_4,$ | $L_4$ |
| ---- | | |

Fig.10(b)

| (f No.) | PEAK Q No. |
|---|---|
| 1, | 1, 7, 8 |
| 2, | 1, 2, 7 |
| 3, | 2, 6, 7 |
| 4, | 2, 3, 6 |
| ---- | |

Fig.10(c)

| No. | CENTRAL COORDINATES |
|---|---|
| 26a, | $X_a, Y_a$ |
| 26b, | $X_b, Y_b,$ |
| 26c, | $X_c, Y_c$ |
| ---- | |

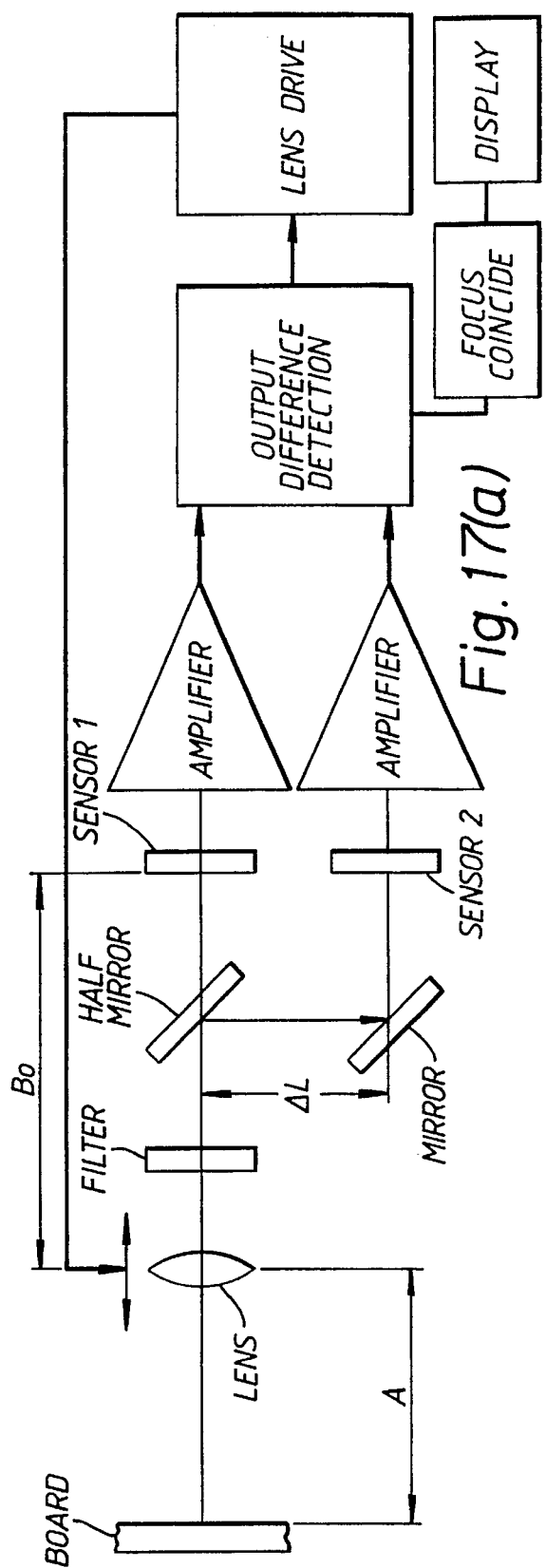
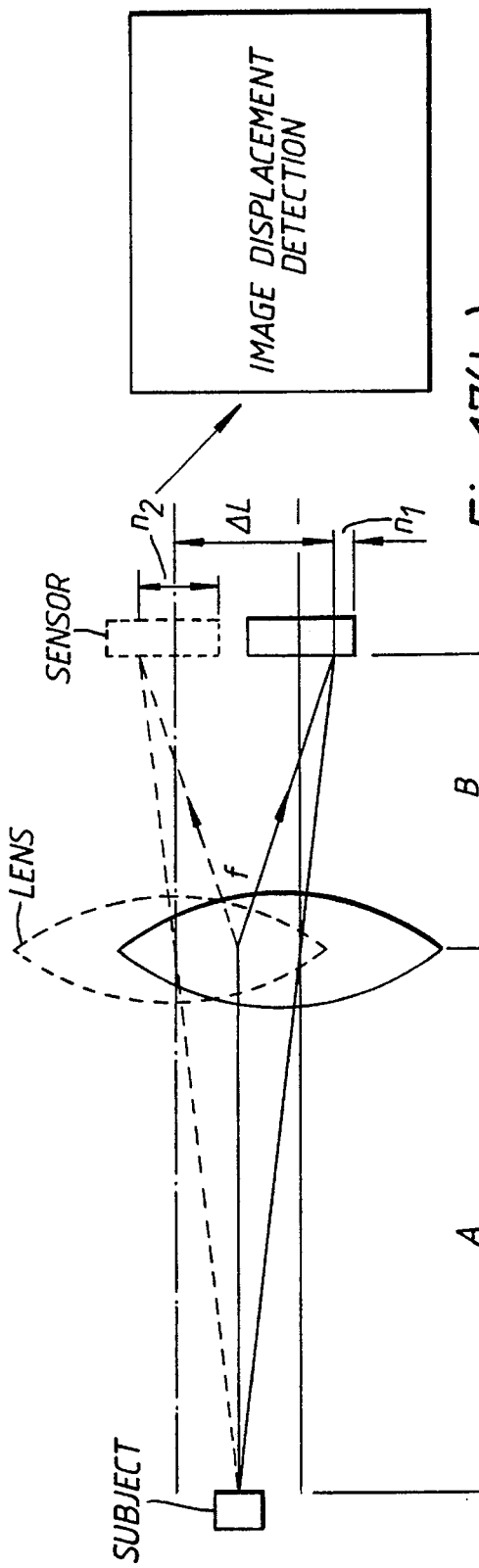
Fig. 17(a)
Fig. 17(b)

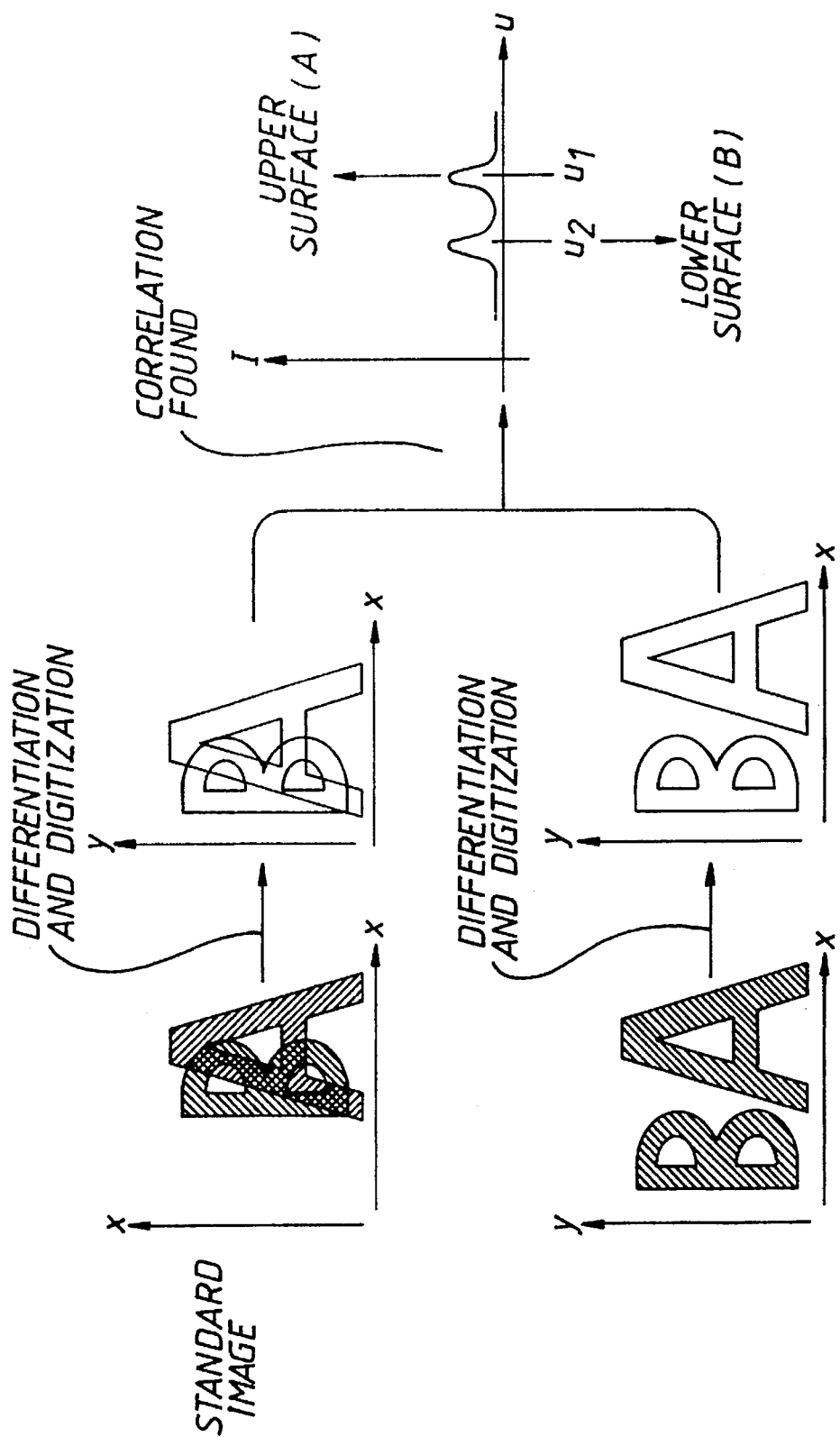

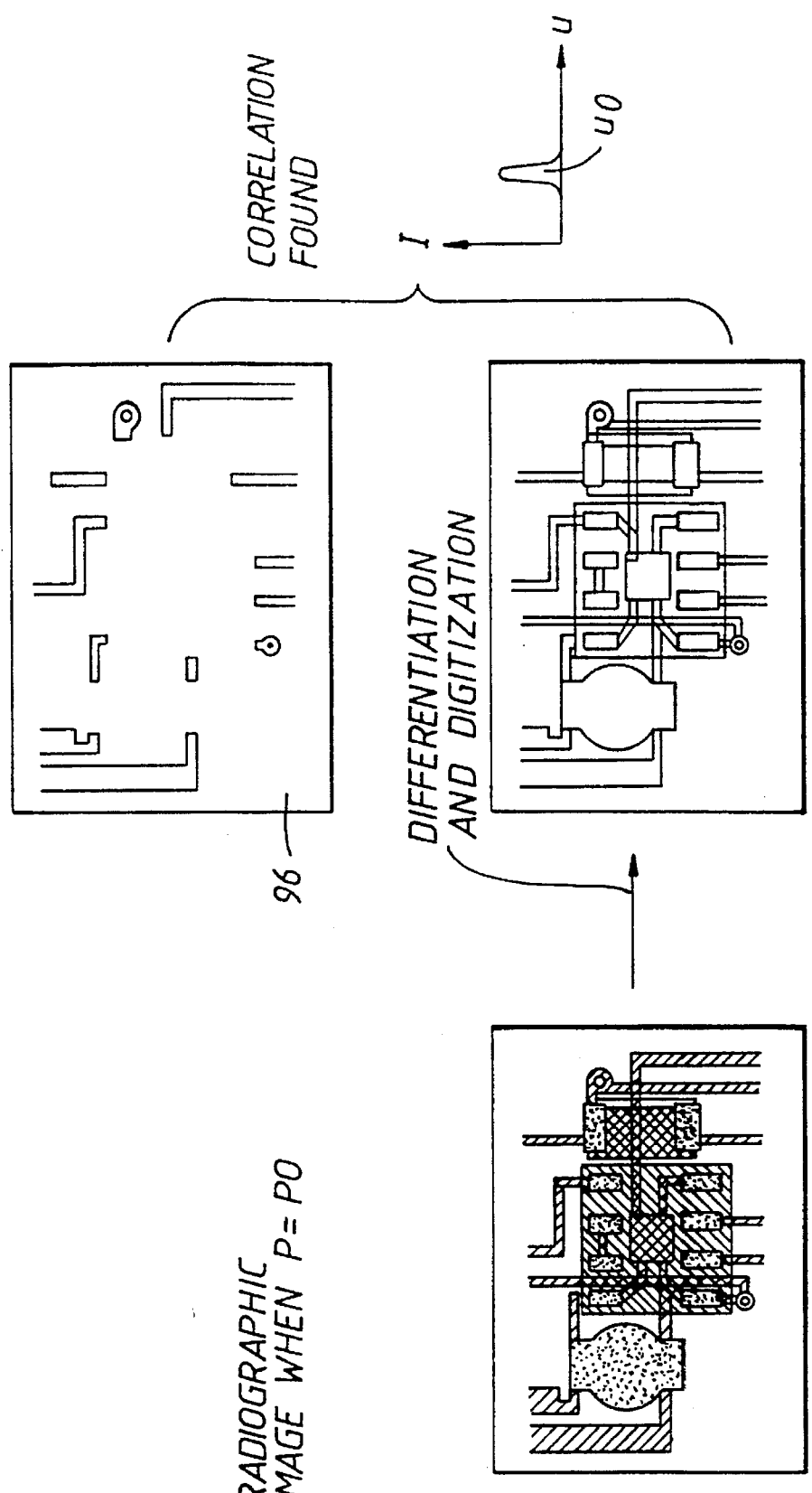

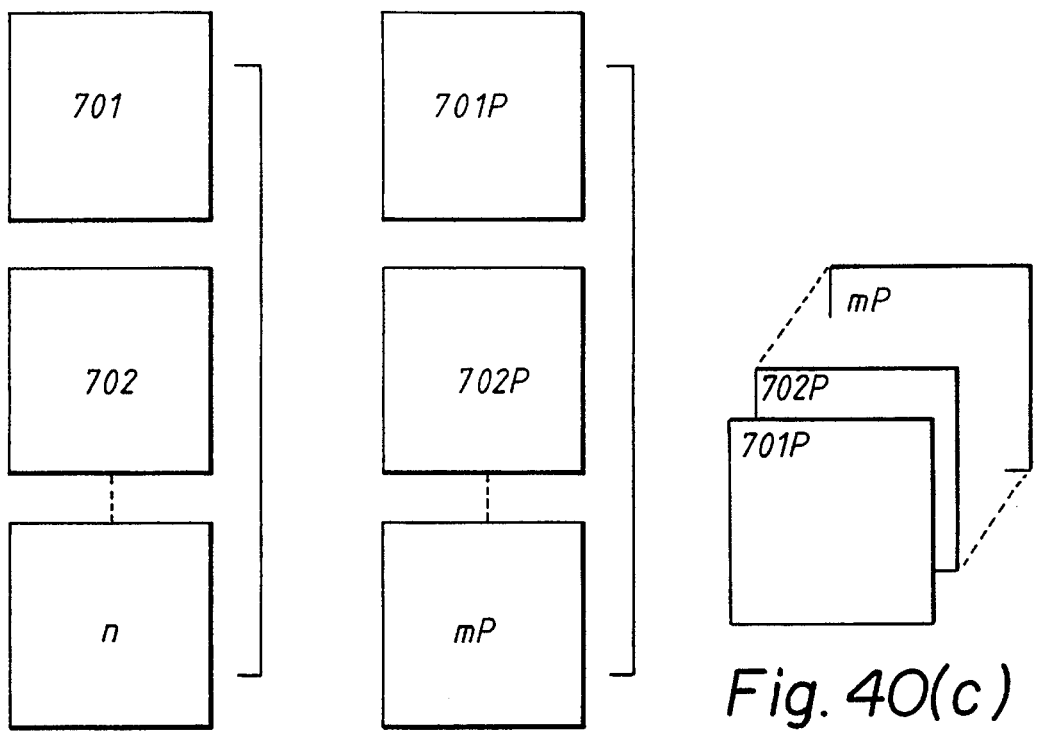
Fig. 40(a)   Fig. 40(b)
Fig. 40(c)
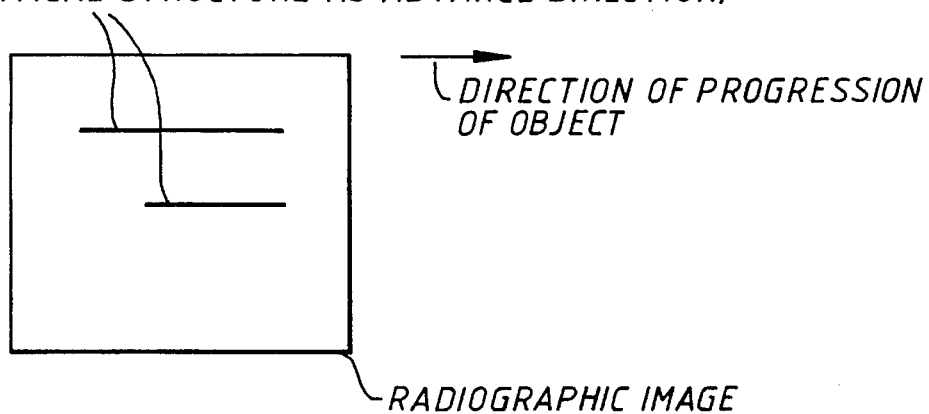
Fig. 41

LAMINOGRAPH AND INSPECTION AND REPAIR DEVICE USING THE SAME

BACKGROUND OF THE INVENTION

1. Field of the Invention

This invention relates to a laminograph and an inspection and repair device using the same. More particularly, this invention relates to a laminograph for detecting X-rays passed through a subject to obtain a tomographic image of the subject, which is used for, for example, nondestructive testing of the interior of multi-printed boards or the soldered parts of the surface mounted boards. This invention further relates to an inspection and repair device to inspect and repair the subject using the laminograph.

2. Description of the Related Art

This type of laminograph has recently attracted attention as being capable of use in the examination of the soldering to be boards of flipchip mounting or surface mounting fitted with J lead terminals, bump fitted passive chip parts and other parts whose connections cannot be examined from the upper surface. It is basically the same as the tomography device widely used in medicine which. obtains a radiographic image along one plane using X-ray film. Whereas in this kind of laminography, the plane sensor output in digitally processed to produce a tomographic image by image processing.

FIG. 52 shows a laminograph of the prior art as described in Japan Patent Disclosure (Kohyou) Hei 2-501411. In this figure, the focal point is moved in a circular scan by a focal point scanning X-ray tube 91. A rotating X-ray detector 94, which is a two-dimensional plane sensor, rotates in synchronization with the focal point and the multiple radiographic images obtained from X-rays passing through a subject 92, which have been collected during this rotation, are added by digital processing to form a single tomographic image. The tomographic image is an image which follows a single focal plane 93 decided by the rotational radius of the focal point and the rotational radius of the rotating detector 94.

FIG. 53 shows a laminograph of the prior art as described in Japan Patent Disclosure (Kokai) Hei 6-88790. In the laminograph shown in this figure, a conical X-ray beam 102 generated from an X-ray tube 101 is measured by an X-ray I.I. (X-ray Image Intensifier) 104 which is a two-dimensional X-ray plane sensor. A subject 103 is penetrated by these X-rays along the measurement plane, and it is possible to produce a tomographic image which precisely fits a single focal plane 105 by image displacement and addition-processing of the multiple radiographic images thus obtained. The focal plane can be changed if the process is repeated with the displacement altered.

In the laminographs of the prior art described above, tomographic images are prepared repeatedly by displacing the position at which the subject is set or by changing the displacement when addition-processing is performed in order to align it precisely along the desired plane, and the optimal focal position is thus obtained. However, when the thickness of the board to be examined varies or when it is curved, it is necessary to focus as described above for each board. This makes the procedures necessary for a laminograph of the prior art complex and time-consuming, which is a problem.

Non-destructive inspection methods in which the subject is irradiated and the X-rays which have passed through the subject are examined already exist. But it may be impossible to assess the faults and structures from such images from transmitted X-rays depending on the kinds or structures of the subjects, and laminography is used in such cases.

FIG. 54 shows the structure and operation of such a laminograph. In this laminograph, multiple line sensors 397 in an array receive each radiographic image in each direction, and the tomographic image is obtained by shifting these so that the desired images overlap among different direction images and by overlapping radiographic images thus shifted.

In greater detail, in the laminograph shown in FIG. 54, there is an X-ray tube 391, which is a penetrating radiation source, multiple line sensors 397 opposite this, which are arranged in equally spaced n lines and detect this radiation on their lines through their spatial resolution. Between this X-ray tube 391 and line sensors 397, there is a transport mechanism 395 which is moved in parallel and at right angles to the direction of the resolution of the line sensors 397, and a subject 393 is placed on this. It also has a signal collection part 390 which collects transmission signals from each of line sensors 397, an addition and averaging part 392 which shifts, adds and averages the radiographic images received from the different line sensors 397, while they are displaced the position of the parallel movement, and a CRT 394 for image display. In FIG. 54, 398 is an X-ray control part and 396 is a mechanism control part.

In the laminograph thus structured, a tomographic image of the required layer section of the subject 393 is obtained by shifting, adding and averaging the radiographic images which are obtained from each of line sensors 397 by sampling the transmission signals at every displacement $\Delta P$, as subject 393 moves, which shifting amount $\Delta S$ is determined according to the distance to the required layer section from the focal point of X-ray tube 391.

It is necessary to carry out the inspection using an enlarged radiographic image in order to improve the resolution in the inspection of electronic parts such as PWBs. In the case of using the laminograph this may be a partially enlarged laminogram. In case of inspecting the subject with a large area, such as a PWB, some of the parts mounted on the subject are enlarged and inspected, which makes an overall assessment difficult. It is also necessary to repair the faulty part, but it is difficult to transmit the inspection results to the repair line. Previously, a hard copy of the image or notes of handwriting have been used. For important cases, it is necessary to keep the documents of the inspection results for many years but storage is not easy.

SUMMARY OF THE INVENTION

Accordingly, one object of this invention is to provide a laminograph which is capable of focusing precisely on the desired plane of a subject.

Another object of this invention is to provide a laminograph with improved S/N ratio in the tomographic image to be obtained.

Still another object of this invention is to provide a laminograph which can efficiently control the inspection position of a subject with a comparatively large inspection area and can inspect the subject with certainty.

Another object of this invention is to provide an inspection and repair device which can efficiently control the inspection position of a subject with a comparatively large inspection area and can inspect and repair the subject with certainty.

These and other objects of this invention can be achieved by providing a laminograph, including, a radiation source for generating radiation towards a subject, a radiation surface sensor device with a two-dimensional resolution, fitted opposite to the radiation source for detecting the radiation from the radiation source which has passed through the subject, a scanning device for moving the subject to take a plurality of different positions between the radiation source and the radiation surface sensor device and for scanning the subject in each of the different positions by the radiation from the radiation source. The laminograph further includes a data collection device for collecting the plurality of outputs of the radiation surface sensor device during the scanning by the scanning device to obtain the plurality of radiographic images of the subject in the different positions, a position measurement device for measuring multiple positions of a focal plane at multiple places of the subject, a displacement measurement device for measuring multiple displacements based on the multiple positions of the focal plane measured by the position measurement device, and an image processing device for adding and averaging the plurality of radiographic images with the displacements to obtain a radiographic image of the subject focused on the focal plane as a tomographic image of the subject.

According to one aspect of this invention, there is provided a laminograph including, a radiation source for generating radiation towards a subject, a radiation surface sensor device, with a two-dimensional resolution, fitted opposite to the radiation source for detecting the radiation from the radiation source which has passed through the subject, a scanning device for moving the subject to take a plurality of different positions between the radiation source and the radiation surface sensor device and for scanning the subject in each of the different positions by the radiation from the radiation source. The laminograph further includes a data collection device for collecting the plurality of outputs of the radiation surface sensor device during the scanning by the scanning device to obtain the plurality of radiographic images of the subject in the different positions, a displacement determining device for determining multiple displacements at multiple places of the subject based on a pattern on the radiographic images, and an image processing device for adding and averaging the plurality of radiographic images with the displacements to obtain a radiographic image of the subject focused on a single focal plane as a tomographic image of the subject.

According to another aspect of this invention, there is provided a laminograph including, a radiation source for generating radiation towards a subject, a radiation surface sensor device, with a two-dimensional resolution, fitted opposite to the radiation source for detecting the radiation from the radiation source which has passed through the subject, a scanning device for moving the subject to take a plurality of different positions between the radiation source and the radiation surface sensor device and for scanning the subject in each of the different positions by the radiation from the radiation source. The laminograph further includes a data collection device for collecting the plurality of outputs of the radiation surface sensor device during the scanning by the scanning device to obtain the plurality of radiographic images of the subject in the different positions, an image pre-processing device for processing one of enhancing, weakening and deleting characteristics of the radiographic images to obtain pre-processed radiographic images, and a laminograph image restoration device for restoring a tomographic image of a desired plane from the pre-processed radiographic images and an information for a transmission direction of the radiation, whereby to improve the S/N ratio of the tomographic image.

According to still another aspect of this invention, there is provided a laminograph including, a radiation source for generating radiation towards a subject, a radiation detection device with a two-dimensional detection area positioned opposite the radiation source for detecting the radiation from the radiation source which has passed through the subject to obtain a radiographic image, and a movement device for moving the subject so as to obtain the radiographic images of the subject from many directions. The laminograph further includes a laminograph image restoration device for restoring a tomographic image of a desired plane from the radiographic images and an information for a transmission direction of the radiation, an image magnification and reduction device for changing a magnification of at least one of the radiographic image and the tomographic image and for changing a magnification of a pattern showing a shape of the subject, a composite image preparation device for preparing a composite image composed of the pattern showing the shape of the subject with a changed magnification and one of the radiographic image and the tomographic image with a changed magnification in the same scale, and a display device for displaying the composite image and at least one of the radiographic image and the tomographic image.

According to another aspect of this invention, there is provided an inspection and repair device including a laminograph. The laminograph includes a radiation source for generating radiation towards a subject, a radiation detection device with a two-dimensional detection area positioned opposite the radiation source for detecting the radiation from the radiation source which has passed through the subject to obtain a radiographic image, and a movement device for moving the subject so as to obtain the radiographic images of the subject from many directions. The laminograph further includes a laminograph image restoration device for restoring a tomographic image of a desired plane from the radiographic images and an information for a transmission direction of the radiation, an image magnification and reduction device for changing a magnification of at least one of the radiographic image and the tomographic image and for changing a magnification of a pattern showing a shape of the subject, a composite image preparation device for preparing a composite image composed of the pattern showing the shape of the subject with a changed magnification and one of the radiographic image and the tomographic image with a changed magnification in the same scale, and a display device for displaying the composite image and at least one of the radiographic image and the tomographic image. The inspection and repair device further includes a communication and control device for communicating an inspection result, the images and a repair result to the laminograph and for controlling the inspection result and the repair result, a display input device for displaying the inspection result and the images and for inputting the repair result, and a device for returning the subject repaired to a inspection process to re-inspect an part which has been repaired of the subject.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5 is a view showing a section of the board shown in FIG. 4;

FIGS. 10a–10c are views showing a point file, a face file and an inspection area file for the board shown in FIGS. 8 and 9;

FIGS. 17a and 17b are views showing the structure of the distance measuring device using the image matching method as one example of the contrast and triangulation methods;

FIG. 19 is a view given in explanation of the operations of the laminograph shown in FIG. 18;

FIG. 30 is a view given in explanation of the operations of a twelfth embodiment of a laminograph according to this invention;

FIGS. 40a–40c are views given in explanation of the display of fixed pitch added images in a fourteenth embodiment of a laminograph according to this invention;

FIG. 41 is a view showing extraction and deletion of specific images in a fifteenth embodiment of a laminograph according to this invention;

FIG. 44 is a view showing the repair device used in the laminograph shown in FIG. 43;

DETAILED DESCRIPTION OF THE PREFERRED EMBODIMENTS

Figure 1A:
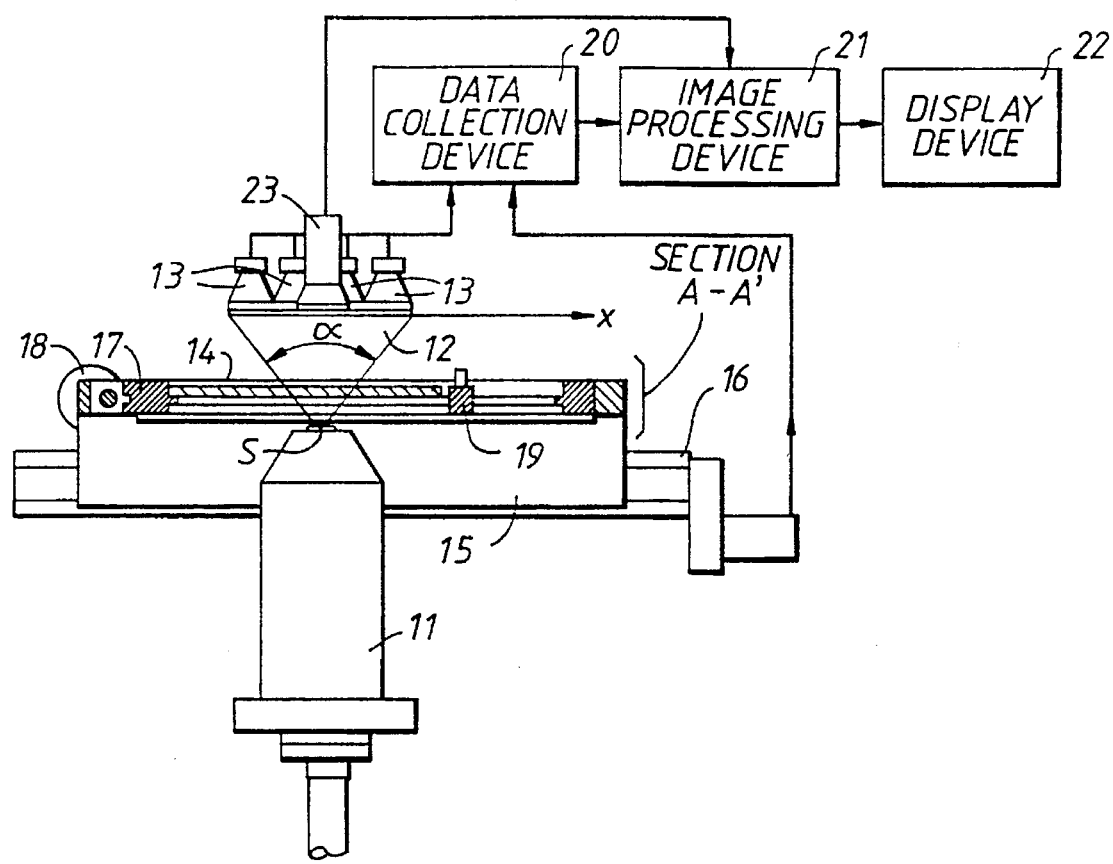
FIGS. 1a and 1b are views showing the structure of a laminograph according to a first embodiment of this invention.

Referring now to the drawings, wherein like reference numerals designate identical or corresponding parts throughout the several views, the embodiments of this invention will be described below.

FIG. 1 is a drawing showing the structure of a laminograph according to a first embodiment of this invention.

Figure 1B:
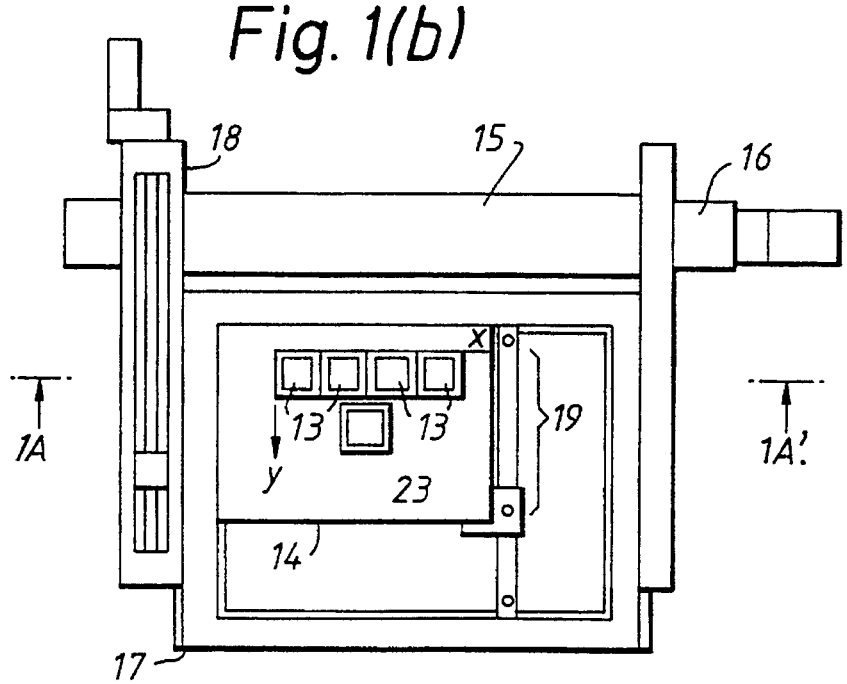

In FIG. 1, (a) is a front view and (b) is a plan view, and one part of FIG. 1(a) shows a section along line A–A' of FIG. 1(b).

The laminograph shown in FIG. 1 has an X-ray tube 11 fixed to a floor (not shown), and a board 14 which is a subject is located over an X-ray focal spot S at the top of X-ray tube 11. Multiple (4 in the case of this embodiment) X-ray detectors 13 are fitted further above board 14, and face X-ray focal spots S of X-ray tube 11. An X-ray beam 12 which is generated from X-ray tube 11 at a beam spread angle a passes through board 14 and is detected by X-ray detectors 13. Adjacent to these X-ray detectors 13, there is provided a distance measurement device 23 to detect the distance to board 14 therefrom.

Board 14 is fixed to on a y frame 17 by a board clamp 19. Y frame 17 is fixed to an x frame 15 via a y movement mechanism 18. X frame 15 is constructed so that it is capable of being moved in axial direction x by an x movement mechanism 16 fixed to the floor (not shown). Also, y frame 17 fitted via y movement mechanism 18 to x frame 15 is constructed so that it is capable of being moved in axial direction y by y movement mechanism 18. And thereby it is possible to move board 14 in axial directions x and y by x movement mechanism 16 and y movement mechanism 18, respectively. Axes x and y intersect each other and an xy plane is fixed horizontally. X-ray detector 13 is set to have measurement plane parallel to the xy plane and four X-ray detectors 13 are fitted in a row along axial direction x.

X-ray radiographic data detected by each X-ray detector 13 is supplied to a data collection device 20. An encoder pulse which is a collection signal fop each fixed movement from x movement mechanism 16 is supplied to data collection device 20. Data collection device 20 synchronized to this pulse signal collects output signals from X-ray detector 13, converts them to a digital image and supplies it to an image processing device 21. Also, distance data to surface of board 14 measured by distance measurement device 23 is supplied to image processing device 21.

Although this is omitted from FIG. 1, the laminograph has a mechanism control device which controls x movement mechanism 16 and y movement mechanism 18 and an X-ray control mechanism which controls and supplies power to X-ray tube 11.

Figure 2:
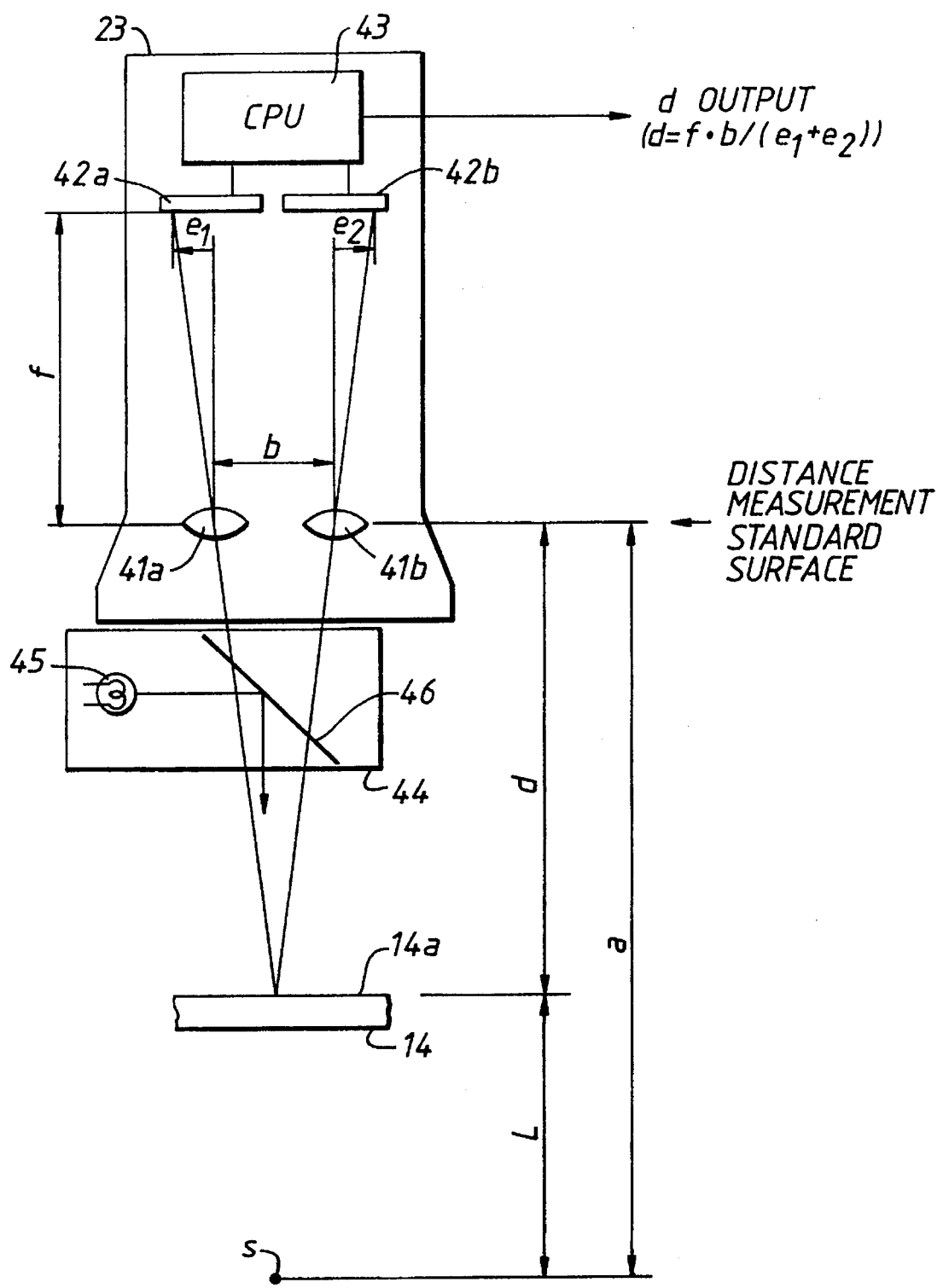
FIG. 2 is a view showing the detailed structure of the distance measuring device used in the laminograph shown in FIG. 1.

As shown in detail in FIG. 2, distance measurement device 23 has two sets of lenses 41a and 41b, CCD sensors 42a and 42b and a CPU 43, and it images the pattern on board 14. Displacements e1 and e2 are then measured, and a distance d from a distance measurement datum plane to a surface 14a of board 14 is calculated by the following equation (1) by CPU 43 and is output as a digital value. Here, b and f are distances shown in FIG. 2.

$$d = f \cdot b / (e1 + e2) \qquad (1)$$

Also, as shown in FIG. 2, if a distance between distance measurement datum plane and X-ray focal spot S of X-ray tube 11 is "a", a distance L between X-ray focal spot S and surface 14a of board 14 is calculated by the following equation (2).

$$L = a - d \qquad (2)$$

A vertically-shining lamp device 44 composed of a lamp 45 and a half-mirror 46, is attached to the front surface of distance measurement device 23. Surface 14a of board 14 is illuminated vertically by this device 44. Even when board 14 is densely mounted with parts, it is possible to illuminate the wiring patterns through the gaps of the parts.

In FIG. 1, X-ray detectors 13 are two-dimensional X-ray plane sensors. A small focal spot X-ray tube, with a focal spot size of several tens to several hundreds μm, is used as X-ray tube 11 in order to obtain an image of high resolution.

Figure 3:
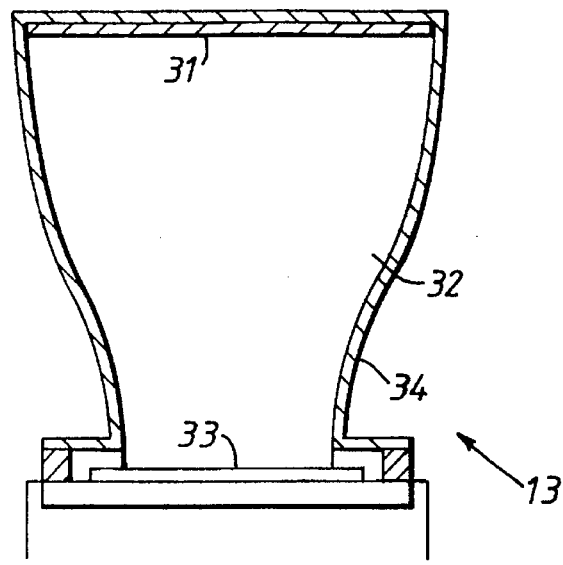
FIG. 3 is a view showing the detailed structure of the detectors used in the laminograph shown in FIG. 1.

As shown in detail in FIG. 3, X-ray detector 13 has a structure in which a scintillator 31 and a CCD two-dimensional optical sensor 33 are fitted to either end of a tapered optical fiber 32. It is possible to obtain a radiographic image of the matrix size (500×500) of CCD two-dimensional optical sensor 33 by one detector 13, and when four detectors 13 are used in a laminograph, it is possible to obtain a radiographic image of the matrix size of 2000×500. In FIG. 3, 34 is a light-shading membrane.

Next, the actions of the laminograph shown in FIG. 1 will be described with reference to FIGS. 4–7.

Figure 4:
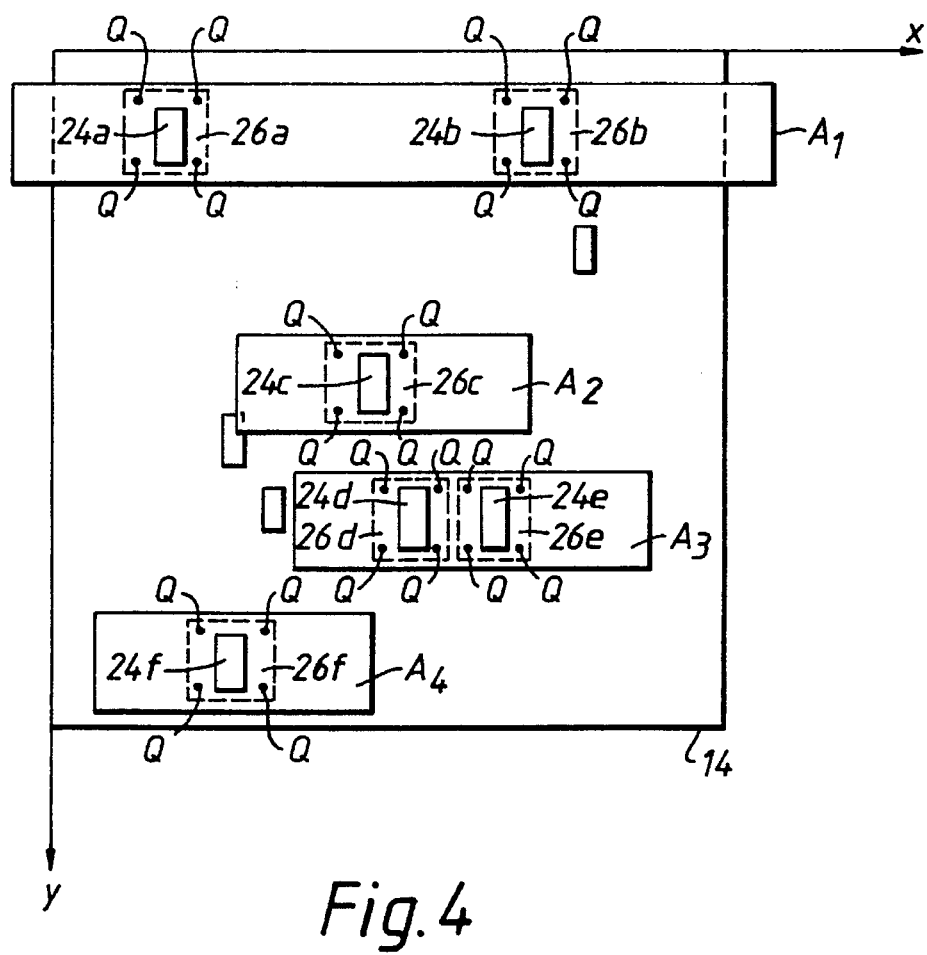
FIG. 4 is a view showing the board which is the subject used in the laminograph shown in FIG. 1.

FIG. 4 shows the detail of board 14 which is the subject. ICs 24a–24f, the soldering of which is the subject, are mounted on-board 14. Inspection areas 26a–26f are fixed around respective ICs 24a–24f, as shown by the dotted line. Scanned areas A1–A4 scanned by X-ray beam 12 are set on board 14, with ICs 24a and 24b located in scanned area A1, IC 24c located in scanned area A2, ICs 24d and 24e located in scanned area A3, and IC 24f located in scanned area A4.

In the laminograph shown in FIG. 1, board 14 is moved by x movement mechanism 16 and y movement mechanism 18, thereby the radiographic images of scanned areas A1–A4 are obtained successively, and the radiographic images, i.e. the tomographic images, of inspection areas 26a–26f, are produced sequentially by image processing device 21. The positions of these scanned areas A1–A4 and inspection areas 26a–26f are described by X–Y coordinates with their starting points at one end of board 14 and memorized in advance in a mechanism control device (not shown) for each type of board. So, it is possible to obtain a tomographic images of inspection areas simply by the operator specifying the type of the board to be inspected.

FIG. 5 show a section of board 14. In this figure, 24 is an IC, 25 are soldered parts, and surface 14a of board 14 is the focal plane. It is necessary to focus on surface 14a of the front surface in order to examine the soldered parts 25 of the front surface of board 14 of this structure, without being obstructed by parts of the front or reverse sides of board 14. When board 14 is curved the focal spot meets only a single focal plane, so it is impossible to focus simultaneously on the soldered parts in all the inspection areas 26a–26f shown in FIG. 4. Thus, in this embodiment, a tomographic image is produced by setting an individual focal plane for each inspection area, which is a feature of this invention. For this purpose, four distance measurement positions Q are set in the respective corners of each of inspection areas 26a–26f as shown in FIG. 4.

Because of this, before scanning, distance measurement device 23 is used to measure distance d between the distance measurement datum plane and surface 14a of board 14 at distance measurement position Q set in each corner of the inspection areas. On the basis of this distance d, calculations are made with Equation (2), as detailed above, to find distance L between surface 14a of board 14 and X-ray focal spot S in each inspection area, and the focal plane is set separately for each inspection area by this.

The position of distance measurement position Q is selected to be a position where a surface pattern is visible without parts, and it is stored in memory beforehand by the mechanism control device along with the inspection area positions of each type of board. Also the values of distances d are supplied from distance measurement device 23 to image processing device 21 and, for example, the values d for the four corners Q of each inspection area are averaged and the distance thus averaged is used for each inspection area.

Next the operation of the preparation of a tomographic image for one inspection area, for example 26a, by image processing device 21 are described with reference to FIGS. 6 and 7.

Figure 6:
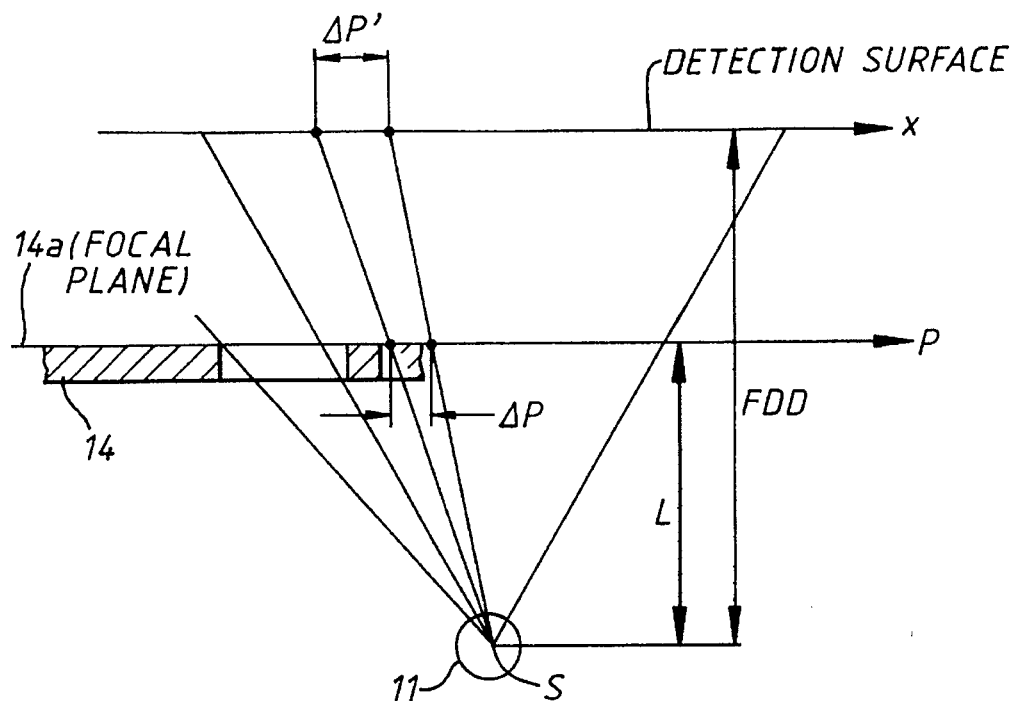
FIG. 6 is an explanatory view showing the operations of the laminograph shown in FIG. 1.

First, as shown in FIG. 6, board 14 is moved in axial direction x (with P as an extent of this movement). Radiographic image is collected each time there is a change in extent of movement ΔP and all these radiographic images are stored in the memory of image processing device 21. When radiographic images at each change in range of movement ΔP are collected, the projection points on the detection surface of detector 13 of the points on the focal plane, i.e. surface 14a of board 14, are displaced by ΔP' each time, as shown in FIG. 6. The change in movement ΔP' can be calculated by the following equation (3).

$$\Delta P' = \Delta P \times FDD/L = \Delta P \times FDD/(a-d) \quad (3)$$

In this equation (3), L is distance between surface 14a of board 14 and X-ray focal spot S of X-ray tube 11 and FDD is a distance between X-ray focal spot S and the detection surface of detector 13. According, ΔP' is a function of distance d detected by distance measurement detector 23.

Figure 7:
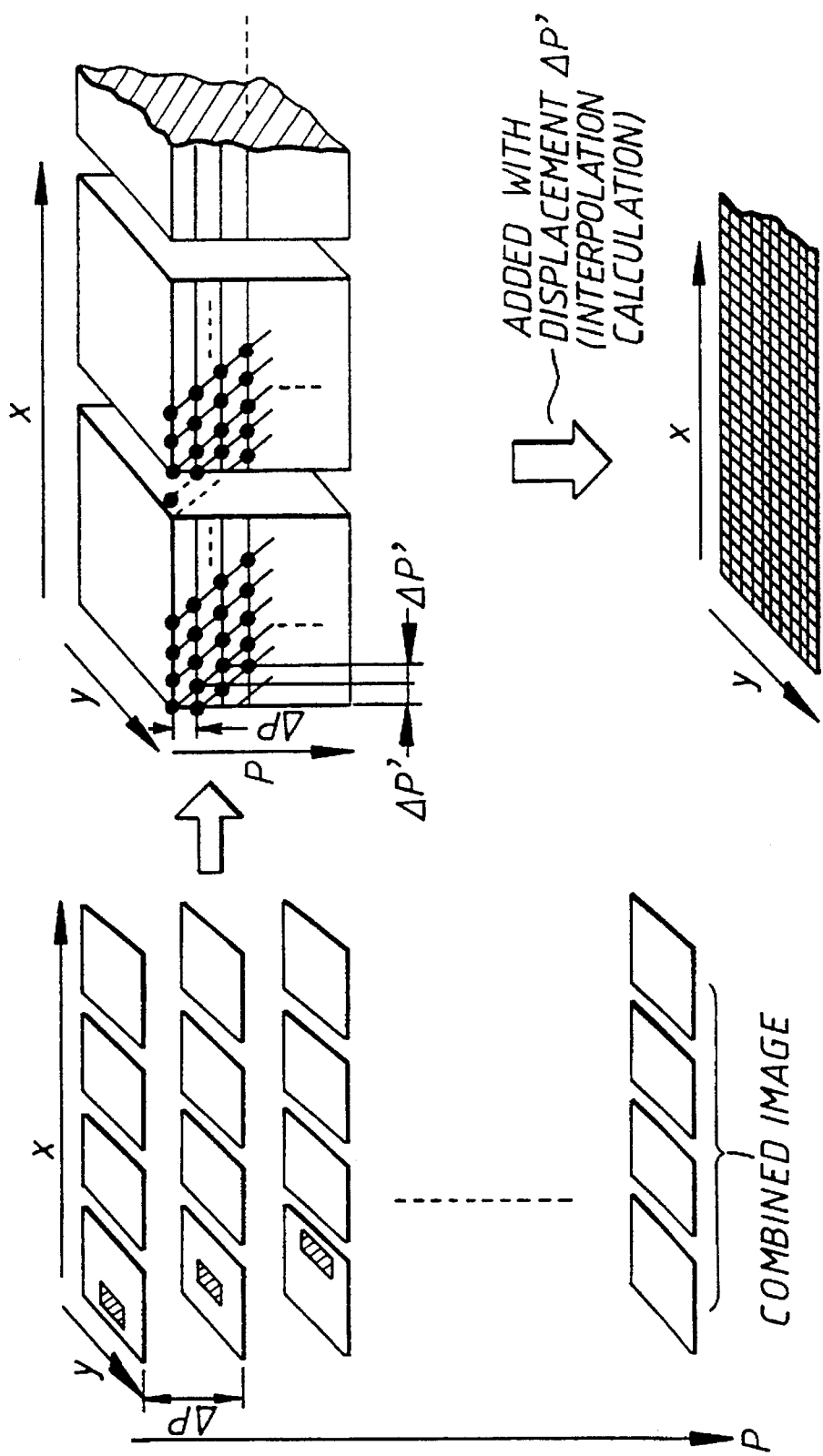
FIG. 7 is an explanatory view showing the operations of the laminograph shown in FIG. 1.

Next, as shown in FIG. 7, the multiple radiographic images obtained by X-ray detectors 13 at the same movement position P are arranged on plane xy at the same distance from each other as the distance between X-ray detectors 13 to form as one combined image. At each change in range of movement ΔP, multiple combined images are arranged in the direction of P as shown in FIG. 7. Then multiple combined images are added and averaged with the displacement ΔP' along axial direction x each other (including linear interpolation calculations). As, by doing this, the points on the focal plane all overlap each other at the same position and they are emphasized, and whereas points not on the focal plane overlap at some distance from each other and are thus vague and blurred.

Thus it is possible to obtain a radiographic image which is focused on a single focal plane parallel to the detection surface, that is, a tomographic image. The image data before adding and averaging are all accumulated in the memory and it is thus possible to prepare a tomographic image on any focal plane by changing ΔP', without collecting data again.

The focal plane position for taking a tomographic image can be set slightly higher (or lower) than upper surface 14a (or lower surface) of board 14 by applying micro-correction terms to ΔP'. It is thus possible to focus on the solder by taking the solder thickness into account. It is also possible to perform correction of errors generated systematically in distance measurement including such errors in setting the distance measurement datum plane. The focal plane position can be aligned with internal layer pattern positions used for pattern inspection as well with the solder position. In such cases, if the thickness from the surface to the internal layer is ΔL, then ΔP' should be calculated by using (L−ΔL) in place of L in equation (3).

Thus, in this embodiment of the invention, even if board 14 is curved, a tomographic image is obtained automatically in which the focal spot coincides with the inspection plane. It is possible to obtain a tomographic image focused on the inspection plane without adjustment, even when the thickness of the board is changed, the position of the inspection plane is shifted, or board clamp 19 is poorly fixed so that the inspection plane is moved.

Surface position measurement is not carried out over the entire surface but only at several points Q in each inspection area. It is thus possible to reduce the inspection time. As distance measurement positions Q are set at positions without parts, it is possible to carry out surface position measurement certainly without being affected by the parts.

As shown in FIG. 2, as there is a vertically shining light 44 which makes it possible to illuminate board 14 from vertically above, even when there is a dense mounting of parts on board 14 it is possible to measure the board surface position relatively simply and precisely.

Also as it is not necessary to move a heavy X-ray tube 11 in a scan, the overall structure of this laminograph is simple and can be miniaturized. Furthermore, as detector 13 is fixed, there is no affect by vibration induced noise.

Figure 8:
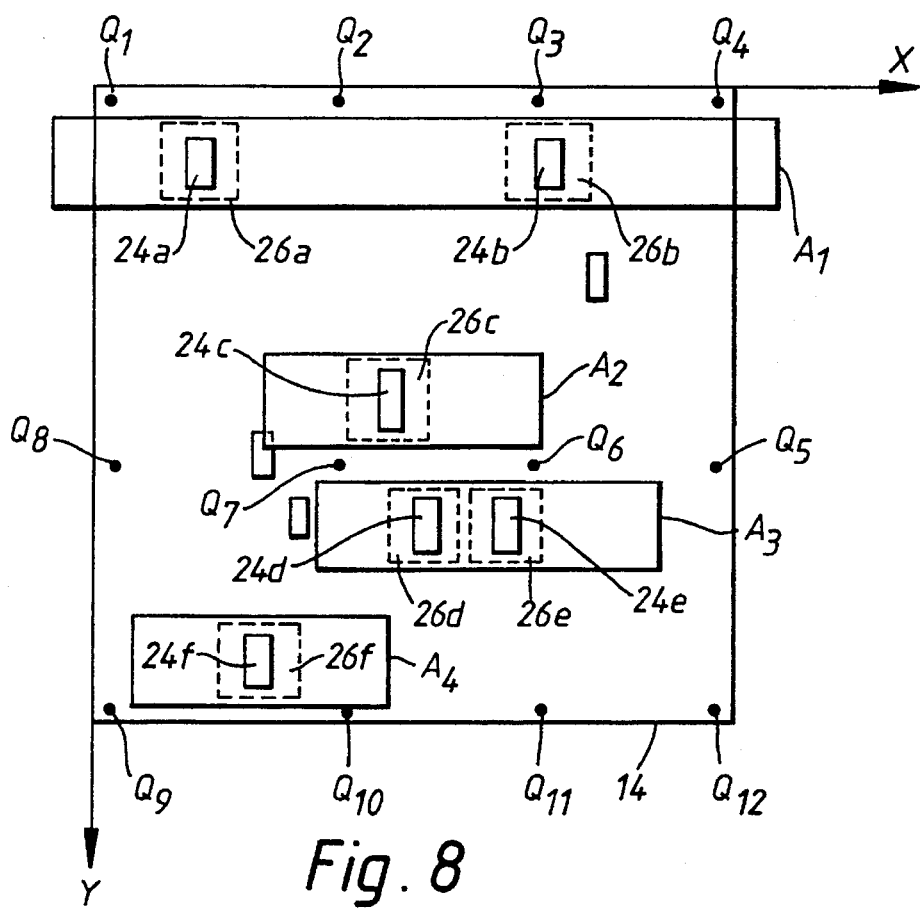
FIG. 8 is a view showing the board used to explain the operation of a second embodiment of the laminograph according to this invention.
Figure 9:
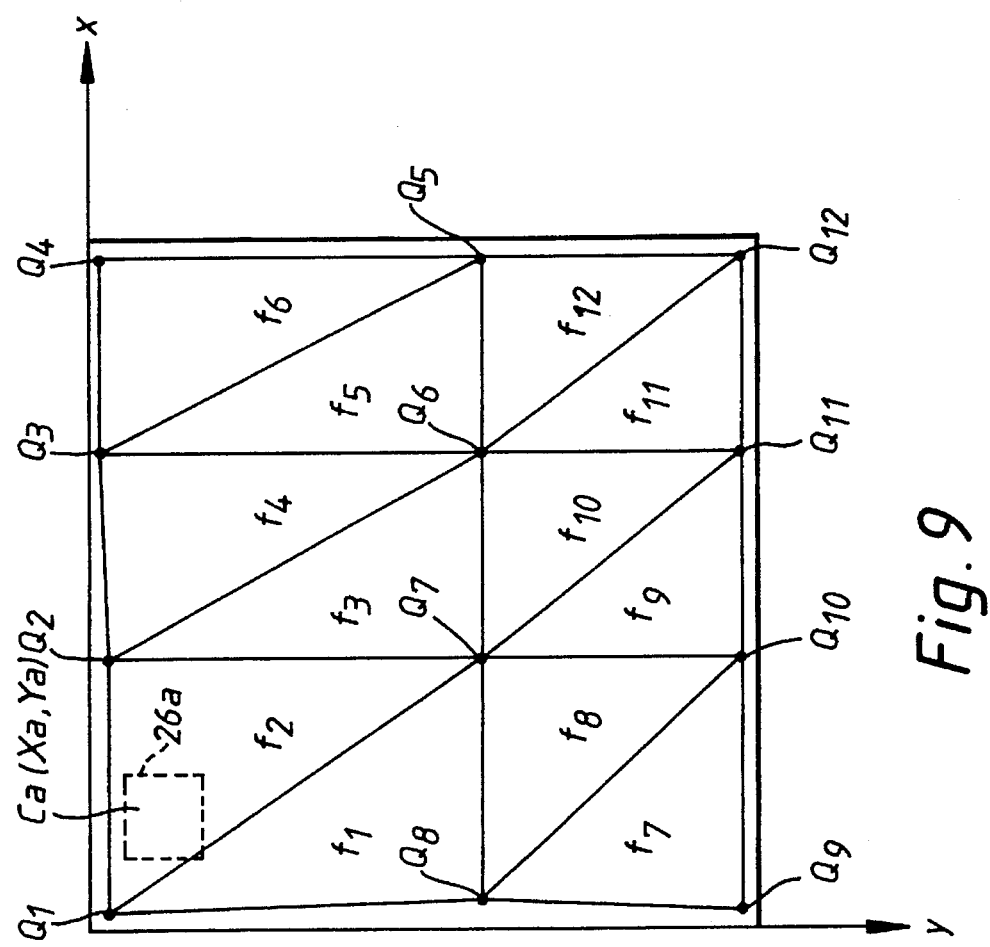
FIG. 9 is a view showing the board shown in FIG. 8 divided in the multiple triangular area faces.

FIGS. 8, 9 and 10 are figures which describe an action of a laminograph according to a second embodiment of this invention. The structure of the laminograph which comprises the second embodiment is the same as the first embodiment.

In the second embodiment, instead of distance measurement positions being found in each inspection area as shown in FIG. 4, appropriate positions are set including corners and edges where parts are not fitted, shown as Q1, Q2, . . . , Q12 in FIG. 8, and it is attempted to calculate distance L in each inspection area from the distances at distance measurement positions Q1–Q12 by interpolation.

As shown in FIG. 9, faces that are triangular areas, are produced with their vertices being three of distance measurement positions Q1–Q12 set as in FIG. 8. The plane of board 14 is divided into these faces which are referred to as f1, f2, f3 . . . f12.

As shown in FIG. 10(a), a point file is prepared in which for each of distance measurement positions Q1–Q12, coordinates X, Y and distance between surface 14a of board 14 and X-ray focal spot, i.e. height L of surface 14a, is described. As shown in FIG. 10(b), a face file is prepared in which for each of faces f1–f12 the numbers of the distance measurement positions Q located at the vertices of this face is described. As shown in FIG. 10(c), an inspection area file is prepared in which for each of inspection areas 26a–26f, central coordinates X and Y of the inspection area are described. These files are stored for each board type in the memory of image processing device 21. Column of surface height L is initially kept blank in the point file shown in FIG. 10(a).

Image processing device 21 calculates surface height L from the value for distance d at each of position Q1–Q12 when the distances d are measured, and each of values L thus calculated is described in column of surface height L. Image processing device 21 reads the central coordinates of each of the inspection areas from the inspection area file shown in FIG. 10(c). The face out of faces f1–f12 to which this center belongs is decided starting with face f1. The distance measurement positions Q at the three vertices of the decided face are read from the face file. The surface height L of the inspection area is calculated by interpolating the values for surface height L at these three points. For example, in the case of inspection area 26a which is shown towards the top left of FIG. 9, this belongs to face f2. Surface height L at central position Ca of inspection area 26a is calculated by interpolation from surface heights L1, L2 and L7 at distance measurement positions Q1, Q2 and Q7 which comprise face f1.

Linear interpolation is used for this interpolation. The attribution of each inspection area to a face and specific interpolation calculations are simple calculations and are therefore not described. It is also possible to produce the face file automatically from the point file (using an element generation technique which is used in a finite element method) instead of preparing it beforehand.

In the second embodiment described above, the number of distance measurement positions are not too many even when a large number of inspection areas on a single board are set densely, and it is possible to shorten the time required for distance measurement. Even when the parts are mounted densely on the board and the distance measurement positions cannot be set freely, this embodiment can be applied with relative ease.

Figure 11:
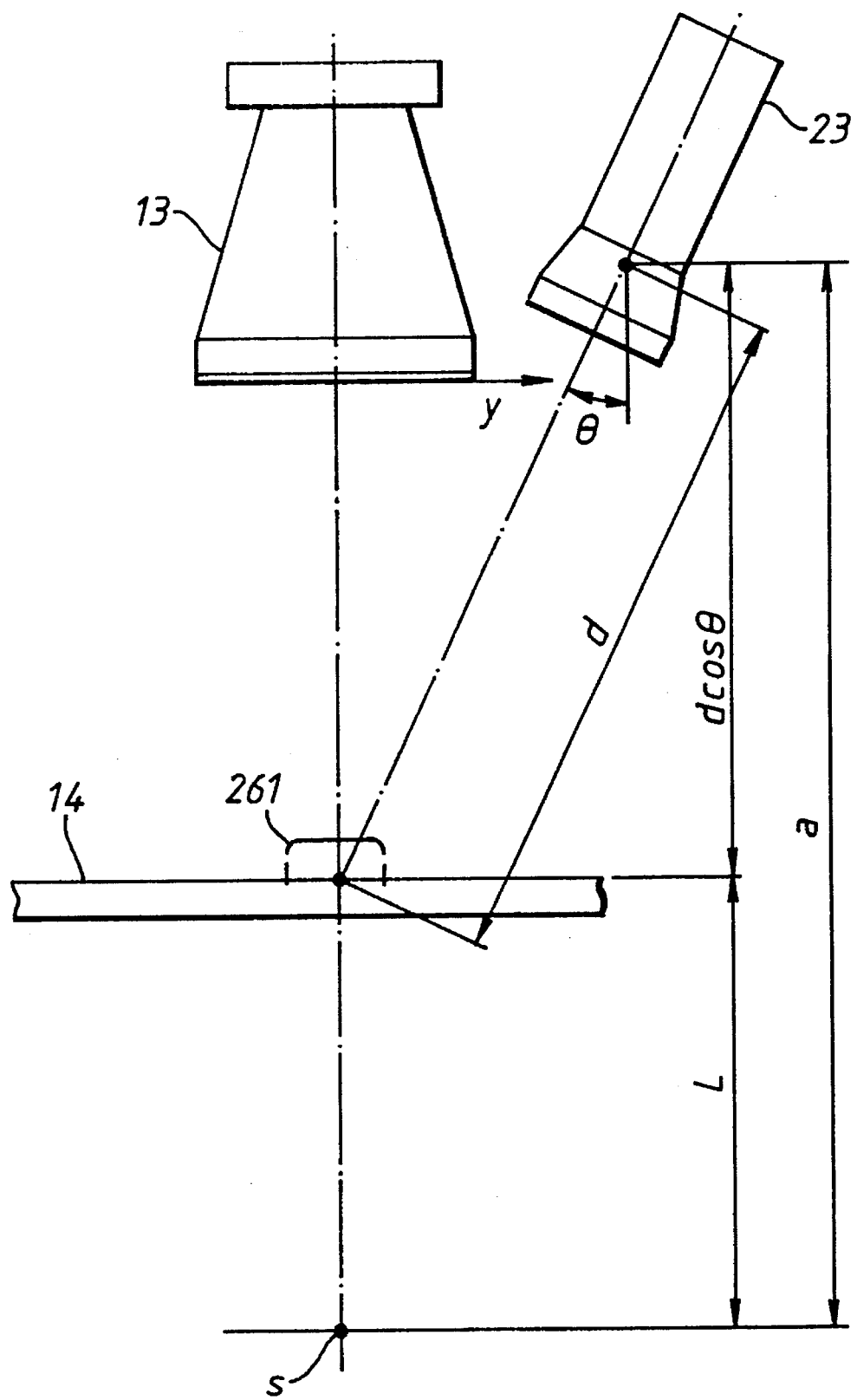
FIG. 11 is a view given in explanation of a third embodiment of a laminograph according to this invention.

FIG. 11 is a view given in explanation of a laminograph according to a third embodiment of this invention. The structure of the laminograph which comprises the third embodiment is the same as the first embodiment except the position of distance measurement device 23.

As shown in FIG. 11, in this third embodiment, distance measurement device 23 is fitted slanting towards inspection area 261 so that during scanning the surface position of inspection area 261 can be measured.

In the third embodiment, as the surface position of inspection area can be measured during scanning, in place of scanning of radiographic image collection being carried out after distance measurement has been carried out in advance, distance measurement can be carried out at distance measurement position set in or near the inspection area during scanning to calculate the surface height L of the inspection area. The other operations are the same as in the first embodiment.

In this third embodiment, it is possible to scan radiographic image collection along with the measurement of the surface height, and thus it is possible to shorten the inspection time.

Figure 12:
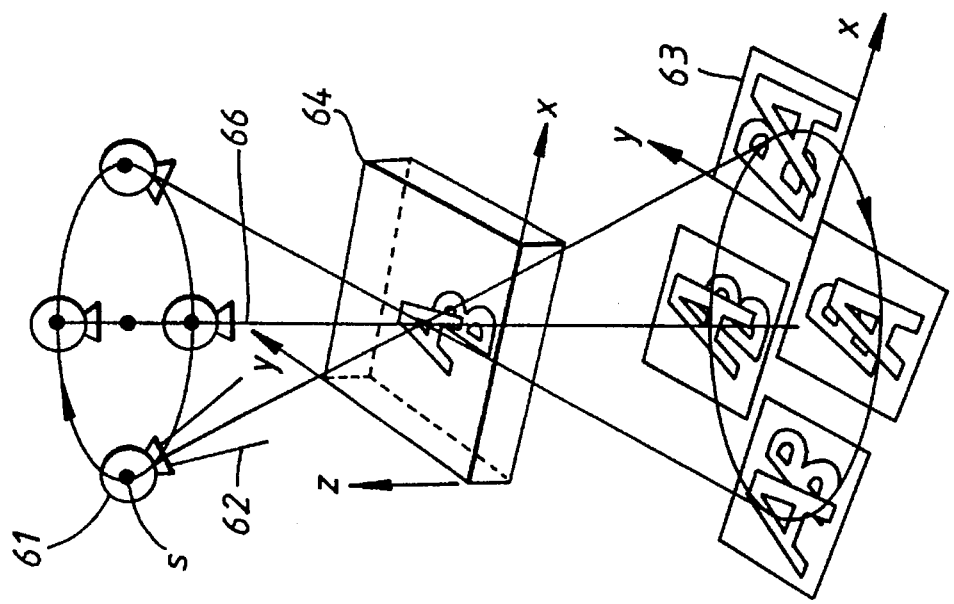
FIG. 12 is a view showing a fourth embodiment of a laminograph according to this invention.
Figure 13:
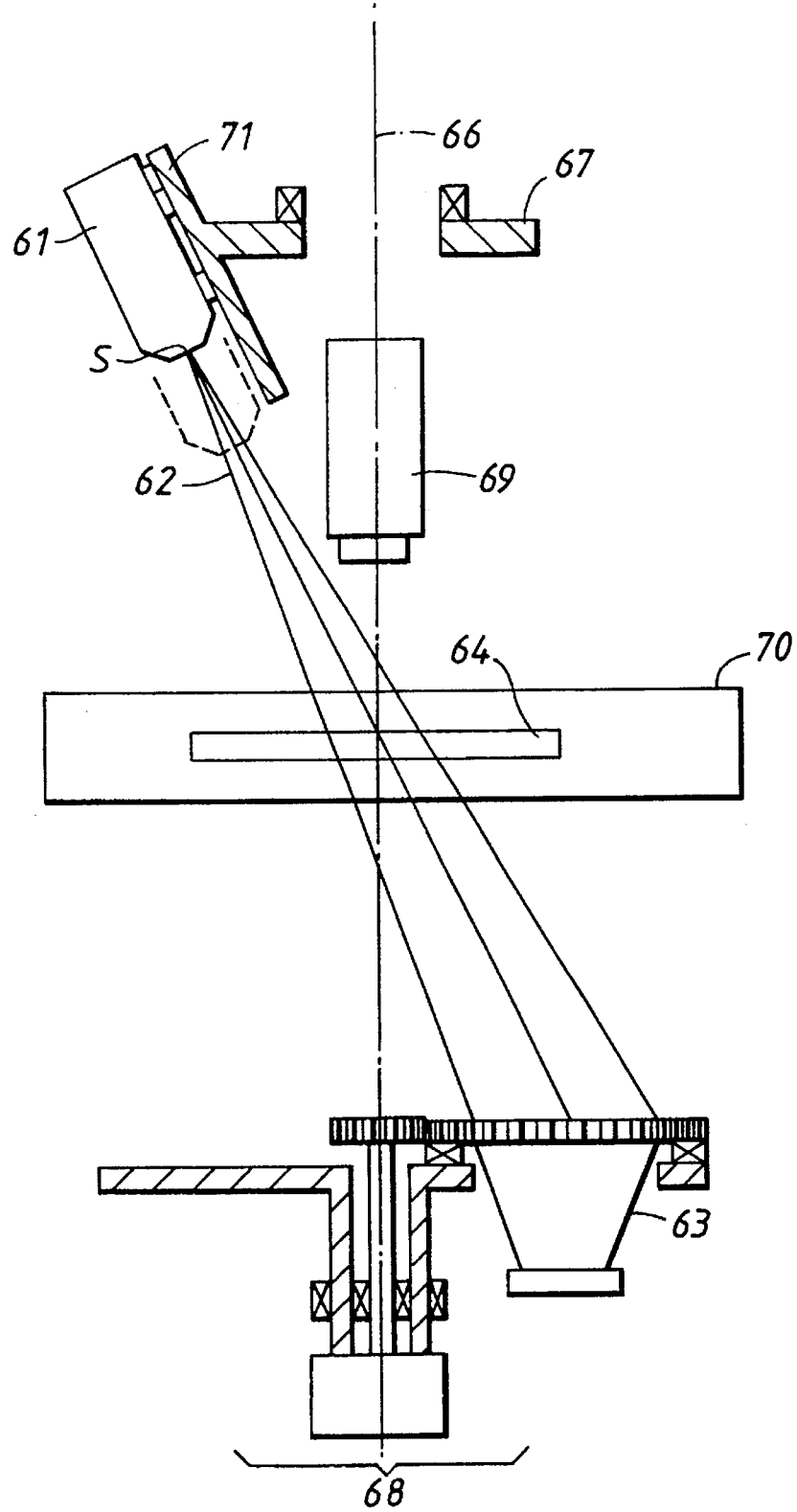
FIG. 13 is a view showing the structure of the fourth embodiment of the laminograph shown in FIG. 12.

FIGS. 12 and 13 show a fourth embodiment of a laminograph according to this invention. As shown in FIG. 12, in this fourth embodiment, an X-ray tube 61 which has an X-ray focal spot S and a detector 63 that is an X-ray plane sensor, face each other with a board 64 which is a subject between them and both of them revolve in synchronism around an axis of rotation 66. In FIG. 12, 62 is an X-ray beam output from X-ray tube 61.

FIG. 13 shows the structure of the fourth example of the laminograph shown in FIG. 12. As shown in this figure, X-ray tube 61 is rotated around axis of rotation 66 by a source rotating mechanism 67, and X-ray beam 62 generated from X-ray tube 61 passes through board 64 which is the subject, and is detected by detector 63. Detector 63 is revolved around axis of rotation 66 by a detector revolution and rotation mechanism 68 and is also rotated on the orbiting frame by mechanism 68 so that it revolves without changing its azimuth. The rotation of X-ray tube 61 and the revolution of detector 63 are linked by gears (not shown) and thus synchronized.

Board 64 which is the subject, is supported by an X, Y, Z table 70. A distance measurement device 69 is fitted on axis of rotation 66 so that it measures the surface position of board 64.

X-ray tube 61 is connected to a source rotating mechanism 67 by a source shift mechanism 71 so that it can be shifted in the direction to detector 63. This source shift mechanism 71 is used to vary the magnification of the tomographic image.

In the fourth embodiment structured as described above, board 64 which is the subject, is moved in axial direction X, Y such that a distance measuring position in or near the inspection area is set in the center, and then the distance is measured by distance measuring device 69. According to this, board 64 is moved in axial direction z to bring the surface of the board 64 to the focal position. Then, board 64 is moved in horizontal direction X, Y so that the inspection area is in the center.

In this state, X-rays are projected from X-ray tube 61 while X-ray tube 61 and detector 63 are rotated, and X-ray radiographic images of the board are collected. The radiographic images thus collected are added and averaged (in this embodiment displacement is unnecessary), and a radiographic image focused on board 64, i.e. a tomographic image, is obtained. It is also possible to focus on a plane which is displaced by $\Delta Z$ on the basis of the surface of board 64 by adding an offset $\Delta Z$ in the above-described movement in axial direction Z.

In the above description, board 64 which is the subject, is displaced in axial direction Z, and the curve of board 64 is corrected to focus on the board surface. But movement in direction Z can be omitted. In such case, "displacement" is calculated from data from distance measurement device 69, and a tomographic image is obtained by adding and averaging the radiographic images while they are displaced as in the first embodiment.

In addition to the advantages seen in the first embodiment, when movement in axial direction Z is applied, this fourth embodiment does not require displacement of the images and only adding and averaging processing is performed. It thus has the advantages that the laminograph is economical in cost and the processing speed is quick. It is also possible to vary the magnification of the tomographic image using source shift mechanism 71. In such cases, the magnification alone can be changed, without changing the position of the focal plane, by making the shift direction the direction shown in FIG. 13.

Figure 14:
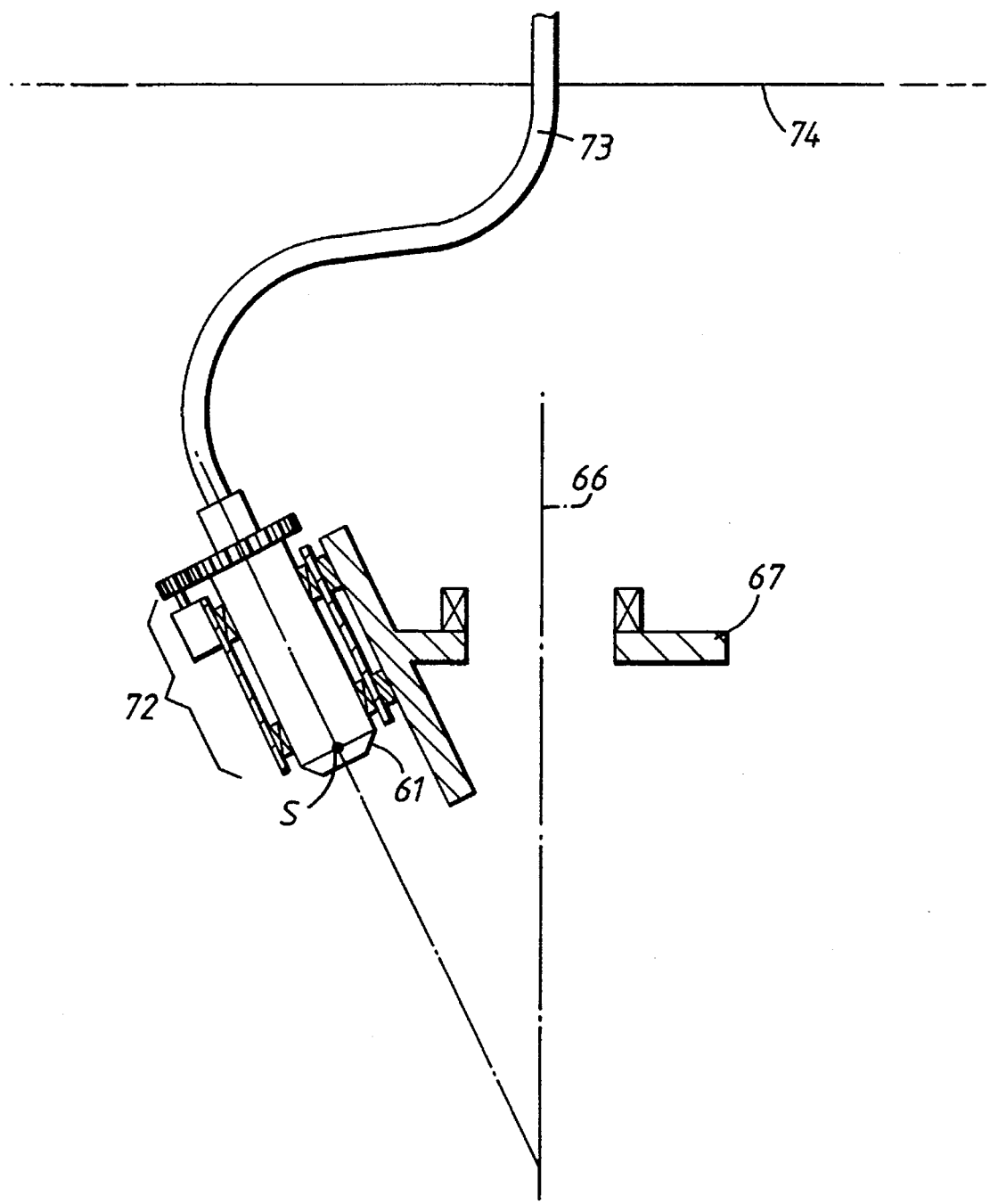
FIG. 14 is a view showing the structure of main points of a fifth embodiment of a laminograph according to this invention.

FIG. 14 shows the essential parts of a fifth embodiment of a laminograph according to this invention. This fifth embodiment is only different from the fourth embodiment as shown in FIGS. 12 and 13, in that it has a source rotating mechanism 72 which rotates X-ray tube 61 around an axis which passes through X-ray focal spot S of X-ray tube 61.

This fifth embodiment (also first to fourth embodiments) has a high voltage cable 73 to connect X-ray tube 61, as shown in FIG. 14 to the X-ray control device (not shown in this figure). When X-ray tube 61 is rotated around axis of rotation 66, X-ray tube 61 is rotated in the opposite direction in synchronization by source rotation mechanism 72. High voltage cable 73 can thus be rotated many times in one direction without becoming twisted. Also, in comparison with the fixed type, no excessive force is exerted on the thick and bend-resistant high voltage cable 73 and its life is thus extended, and thus the cable accommodation space need only be small.

Figure 15A:
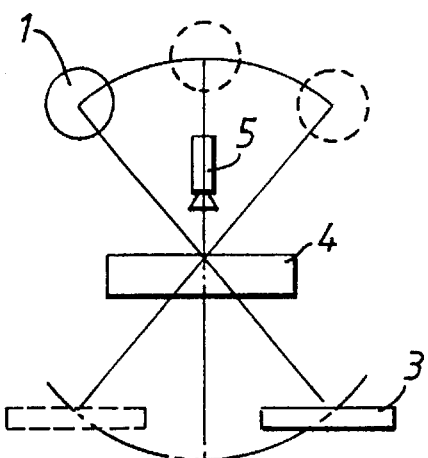
FIGS. 15a and 15b are views showing a sixth embodiment of a laminograph according to this invention
Figure 15B:
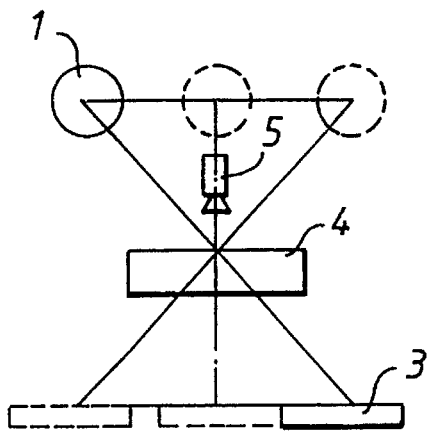

FIG. 15 shows a sixth embodiment of a laminograph according to this invention. In Figures (a) and (b), an X-ray tube 1 which is the radiation source, and a detector 3 which is the radiation plane sensor, are constructed so as to move in synchronization in a curved motion and a straight motion, respectively. In the scanning method achieved by these structures, it is possible to adjust the focus in a similar way as in the fourth embodiment. In FIG. 15, 4 is a subject and 5 is a distance measurement device.

Figure 16A:
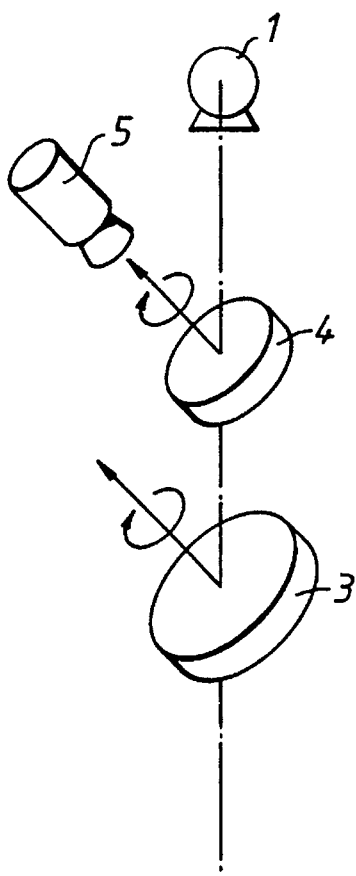
FIGS. 16a and 16b are views showing a seventh embodiment of a laminograph according to this invention.
Figure 16B:
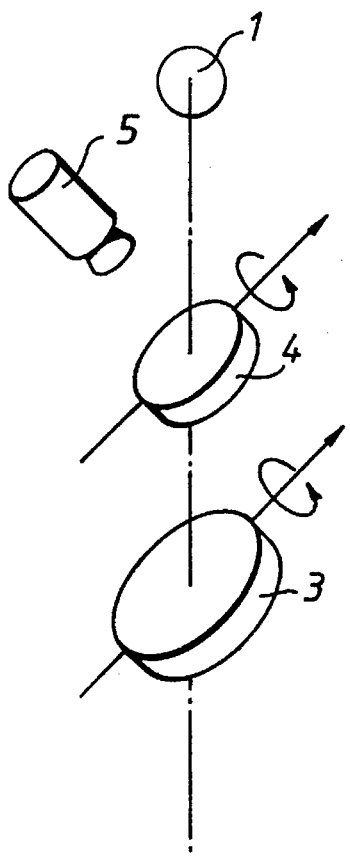

FIG. 16 shows a seventh embodiment of a laminograph according to this invention. In these Figures (a) and (b); subject 4 and sensor 3 which is the radiation plane sensor ape constructed so as to rotate in synchronization in each axis which is parallel to each other. In the scanning method performed by these structures, it is possible to adjust the focus in a similar way as in the fourth embodiment.

The distance measurement device used in the embodiments described above is that shown in FIG. 2. But this invention is not limited to these embodiments. The distance measurement method which can be used in this invention may be, for example, as shown below. (First Symposium on Image Sensing Technology in Industry, p. 279, 19–20 June 1986)

Distance measurement

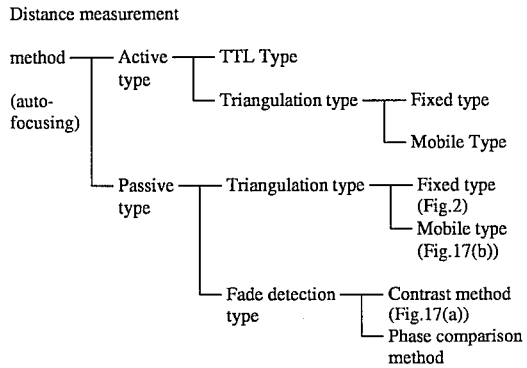

FIG. 17(a) shows a distance measurement device which uses the contrast method (Sensor Interfacing No. 2; CQ Shuppansha 1983; p. 33). The distance measurement device shown in this figure has sensors No. 1 and No. 2 whose light routes are different by a distance $\Delta L$. The contrast value is output according to the differential output of neighbouring channels by the sensors (line sensors). The lens is moved until the contrast values become equal and the distance is measured by the degree of this movement.

Thus if a focal distance is f, an image distance of sensor 1 when contrast values become equal to Bo, then the distance A from the lens to the board which is the subject is found from the following equation:

$$A = f \cdot \{Bo + (\Delta L/2)\} / \{Bo + (\Delta L/2) - f\}$$

FIG. 17(b) shows a structure of a distance measurement device which uses image matching method as one example of triangulation (Sensor Interfacing No. 2; CQ Shuppansha 1983; p. 41). The distance measurement shown in the figure measures the distance to the subject by moving the optical axis of the lens in parallel and detecting the displacement of the image projected to the sensors.

If a detection distance is A, an image distance is B, a magnification is M, a displacement of optical axis is $\Delta L$, numbers of measured pixels are n1 and n2 and a difference between them is $\Delta n$, a pixel pitch is P and a focal distance is f, then.

$$M = B/A$$

or $$M = \Delta n \cdot P / \Delta L$$

$$\Delta n = n2 - n1$$

Therefore, detection distance A to the subject is shown as in the following equation.

$$A = \Delta L \cdot B / (\Delta n \cdot P)$$

or $$A = f(1+M)/M$$

The radiation plane sensor used in the embodiments described above is that shown in FIG. 3. But this invention is not limited to these embodiments and other types may be used. For example, an X-ray I.I. may be used. In this case, the weakness is that there is distortion of the image but image correction makes it possible to use. As X-ray I.I. has a comparatively large detection surface, it is especially effective when used for large subjects.

Also as a television image pickup tube is sensitive to X-rays, it may be used as a radiation plane sensor. In such cases, distortion correction is also necessary. The detection surface of a pickup tube is small and a pickup tube is of high resolution, but the detection efficiency declines fop high energy X-rays, it is not preferable in such cases. Therefore a pickup tube is effective when used for high precision examination of a small subject through which X-rays travel with relative ease.

A combination of a fluorescent sheet and a television camera may also be used as a radiation plane sensor. In this case, a detection surface larger than that of the X-ray I.I. may be obtained. Any other radiation plane sensors with two-dimensional resolution may be used, in any form.

Inspection of soldering of surface mounted board is performed by the embodiments described above. But this invention is not limited to inspect such soldering. The laminograph according to this invention may be used, for example, for inspection of the internal patterns of multilayer boards, interior faults of electronic parts, dimension inspection and airport baggage inspection.

Figure 18:
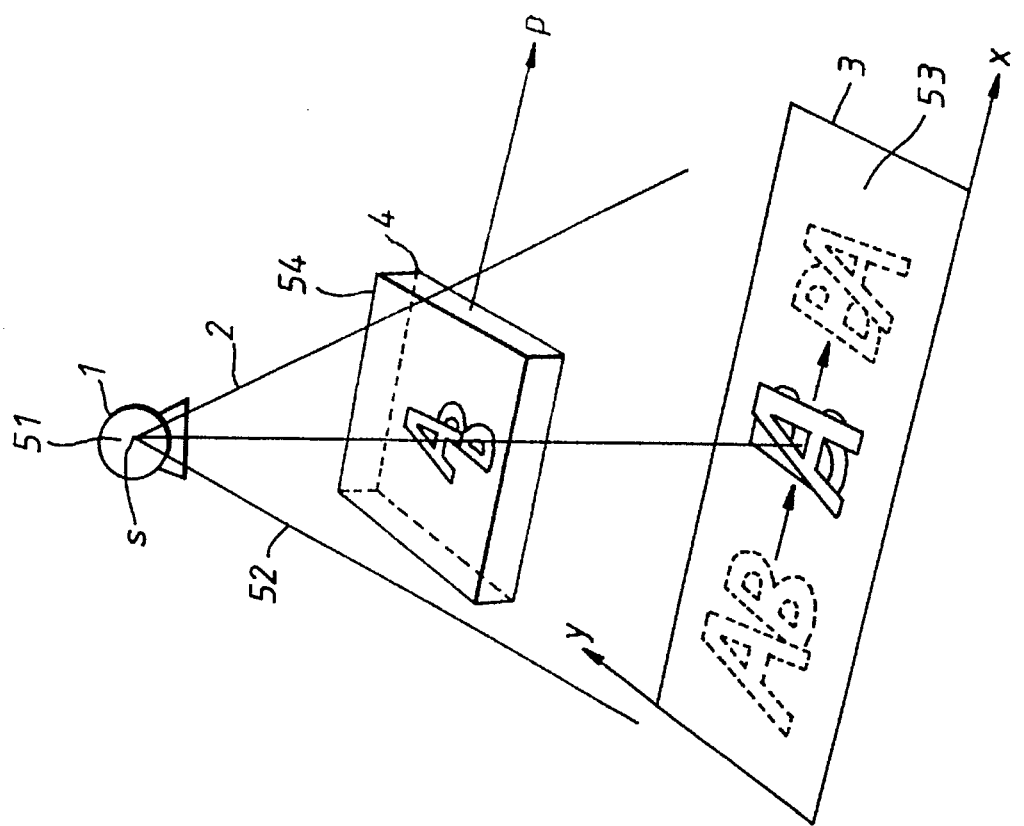
FIG. 18 is a view showing an eighth embodiment of a laminograph according to this invention.

FIG. 18 shows an eighth embodiment of a laminograph according to this invention. In embodiments of the laminograph described above, the distance to surface 14a of board 14, which is the focal plane is measured using a distance measurement device, and a focal plane is focused on at a distance based on this measured distance. By contrast, in this embodiment, focusing is made by a pattern on the radiographic image. This pattern may be, for example, a wiring pattern, soldering patter or board pattern which has been obtained beforehand as set data.

In FIG. 18, a radiation beam 52 which is emitted from a radiation focal spot S of a radiation source 51 passes through a subject 54 and is detected by radiation plane sensors 53. As also shown in this figure, a plane xy is set as the measurement plane. In the figure, the letter "A" is written on the front surface and "B" on the rear surface of subject 54. Subject 54 is moved parallel to axial direction x by a scanning means (not shown), and the radiographic image of subject 54 is obtained by radiation surface sensor 53 and data collection device (not shown) at equal scanning distances. An image processing device (not shown) differentiates and "converts to binary image" (hereinafter is written as "digitizes") the radiographic images and then displaces them along direction x to take their correlations with a standard image. A correlation value I becomes large at the position at which the patterns match.

Thus, as shown in FIG. 19, the radiographic images differentiated and digitized in the image processing device are displaced along direction x and are correlated with the standard image. Two peaks appear in correlation values I at two degrees of displacement, u1 and u2, in two cases, when there is a match with pattern "A" on the front surface of subject 54 and when there is a match with pattern "B" on the reverse surface of subject 54.

When subject 54 is a two-layer board with pattern "A" on the front surface and pattern "B" on the reverse surface, the front surface which is nearer to radiation source 51 forms a peak at a larger displacement u1 and the reverse surface which is further away forms a peak at a smaller displacement u2. Therefore, when it is wished to focus on pattern A on the front surface, specification control is performed so that the peak with the larger degree of displacement u1 is selected. The image processing device adds and average the radiographic images to the standard image by displacement u1 along direction x. By performing this process for all radiographic images, it is possible to obtain a tomographic image which is a radiographic image focused on the front surface of subject 54.

When, for example, subject 54 is a four-layer board, when correlations are taken as described above, four peaks u1, u2, u3 and u4 are formed. It is therefore possible to obtain a radiographic image focused on the desired layer by specifying which number of displacements from the largest one.

Figure 20A:
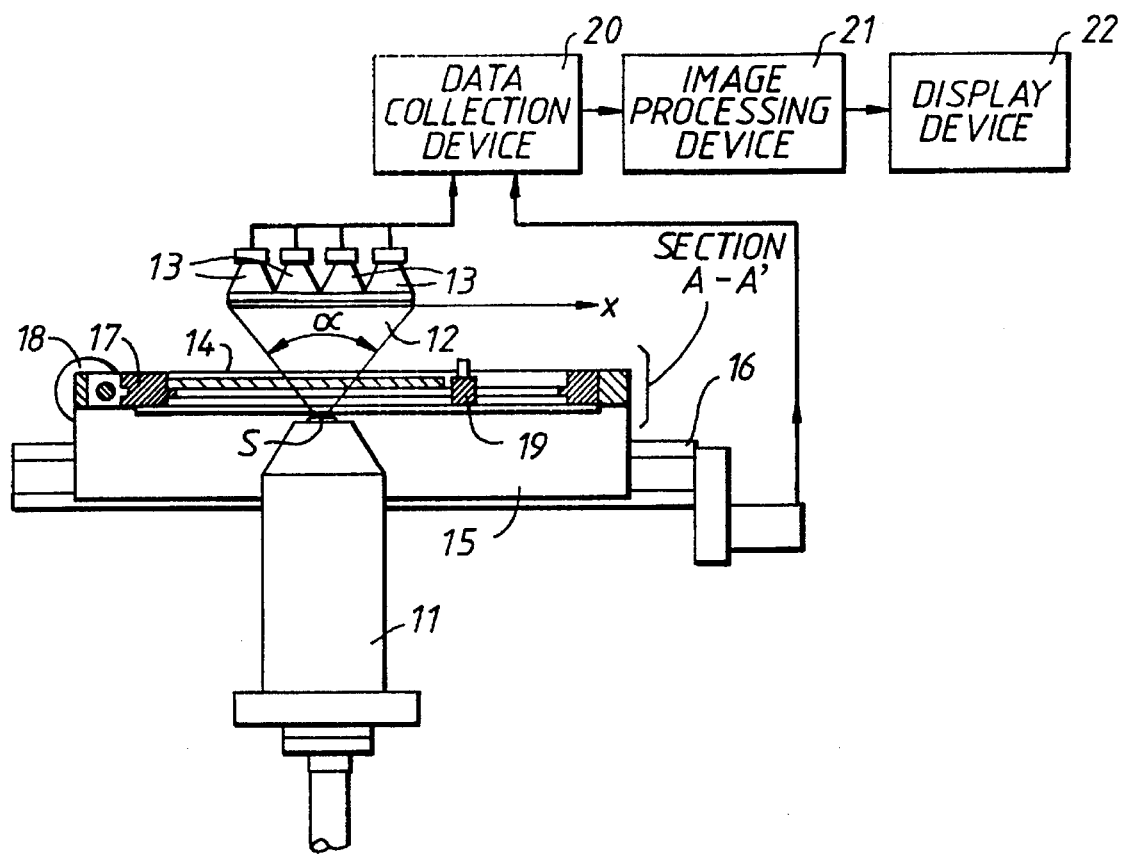
FIGS. 20a and 20b are views showing the structure of a ninth embodiment of a laminograph according to this invention.
Figure 20B:
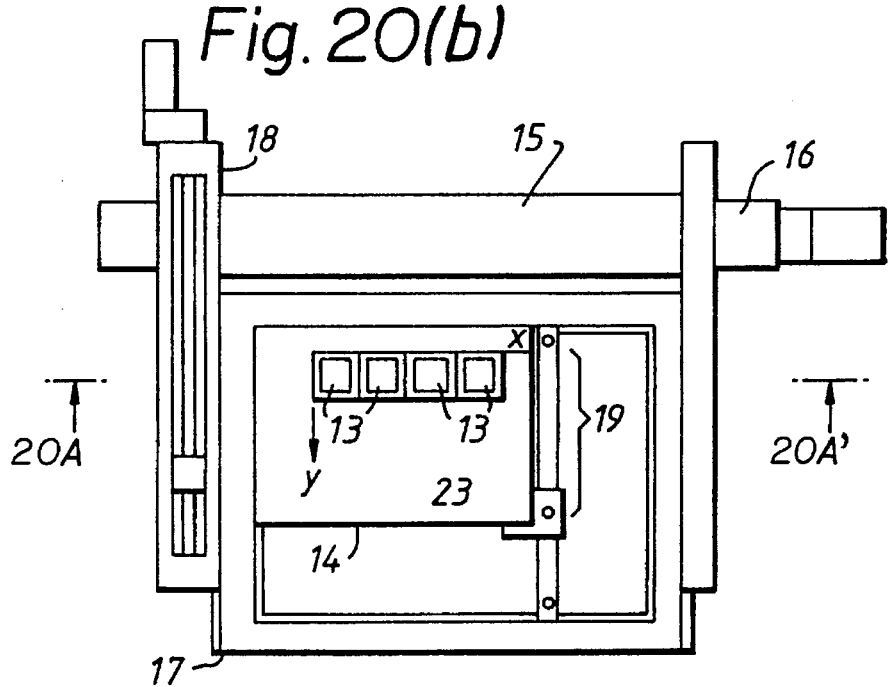

FIG. 20 is a drawing showing the structure of a laminograph according to a ninth embodiment of this invention, and (a) and (b) show, respectively, a front view and a plan view of the laminograph. One part of FIG. 20(a) shows a section along line A–A' in FIG. 20(b).

In the laminograph shown in FIG. 20, the structure is the same as that in the embodiment shown in FIG. 1, except for the absence of distance measurement device 23. Detectors 13 used in the laminograph shown in FIG. 20 is the same as that shown in FIG. 3.

Below, the operations of the ninth embodiment of the invention is described with reference to FIGS. 21–24.

Figure 21:
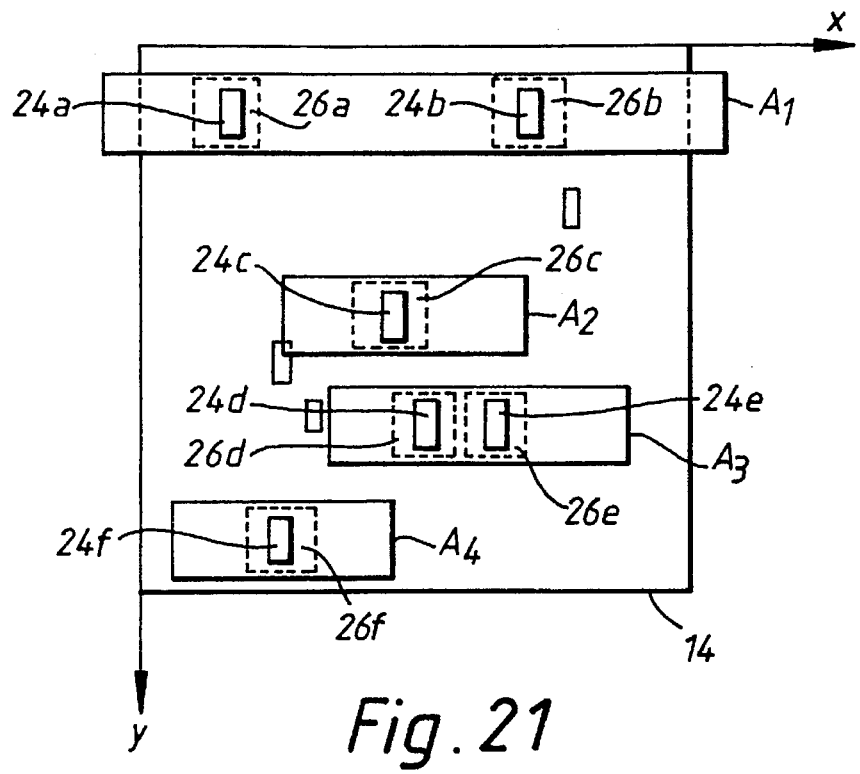
FIG. 21 is a view showing the board which is the subject used in the laminograph shown in FIG. 20.

FIG. 21 shows the same board 14 as that shown in FIG. 4, except that the distance measurement positions are not particularly specified on board 14.

Board 14 shown in FIG. 21 is moved by x movement mechanism 16 and y movement mechanism 18, the radiographic images of scanned areas A1–A4 are obtained successively by data collection device 20 and tomographic images of inspection areas 26a–26f are prepared successively by image processing device 21. The positions of these scanned areas A1–A4 and inspection areas 26a–26f are defined by coordinates X and Y which have their origins at one end of board 14. As these are stored in memory beforehand by the mechanism control device for each board type, the operator can obtain a tomographic image of an inspection area simply by specifying the type of the board to be inspected.

Board 14 shown in FIG. 21 has soldered parts 20 as shown in FIG. 5 and front surface 14a of board 14 is the focal plane. In order to inspect the soldered parts 25 at front surface 14a without any interference to the parts on the rear surface and front surface of the board, it is necessary to focus on front surface 14a of board 14. When board 14 is curved, as the focusing is only on a single focal plane it is not possible to focus simultaneously on the soldered parts of all inspection areas. Thus, in this embodiment, a focal plane is set individually for each inspection area to prepare tomographic images.

Next the operation by which a tomographic image is prepared with image processing device 21 for a single inspection area, for example, inspection area 26a is described with reference to FIG. 22–24.

Figure 22:
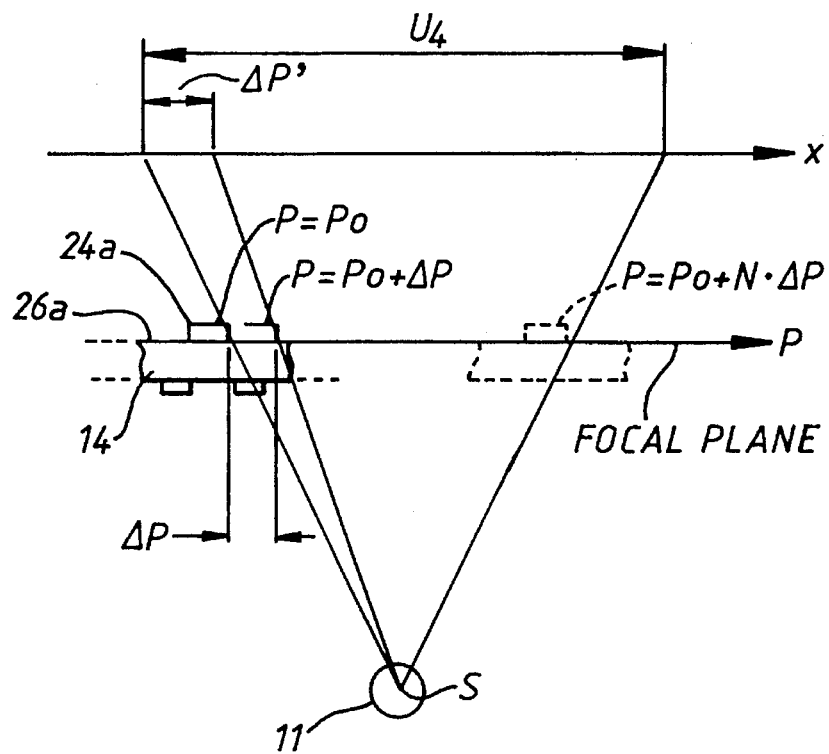
FIG. 22 is a view given in explanation of the operations of the laminograph shown in FIG. 20.

First, as shown in FIG. 22, board 14 is moved in axial direction x (with P being the distance moved), and a radiographic image is collected for each change ΔP in the distance moved and all of these radiographic images are stored in the memory of image processing device 21. Next, two radiographic images at two movement distances Po and (Po+N·ΔP), are used to find the "degree of displacement". Here, Moved distance Po and number of movements N are decided by the position of the inspection area on board 14, and two radiographic images are selected such that the positions of the inspection area are near the ends of the radiographic images.

Figure 23:
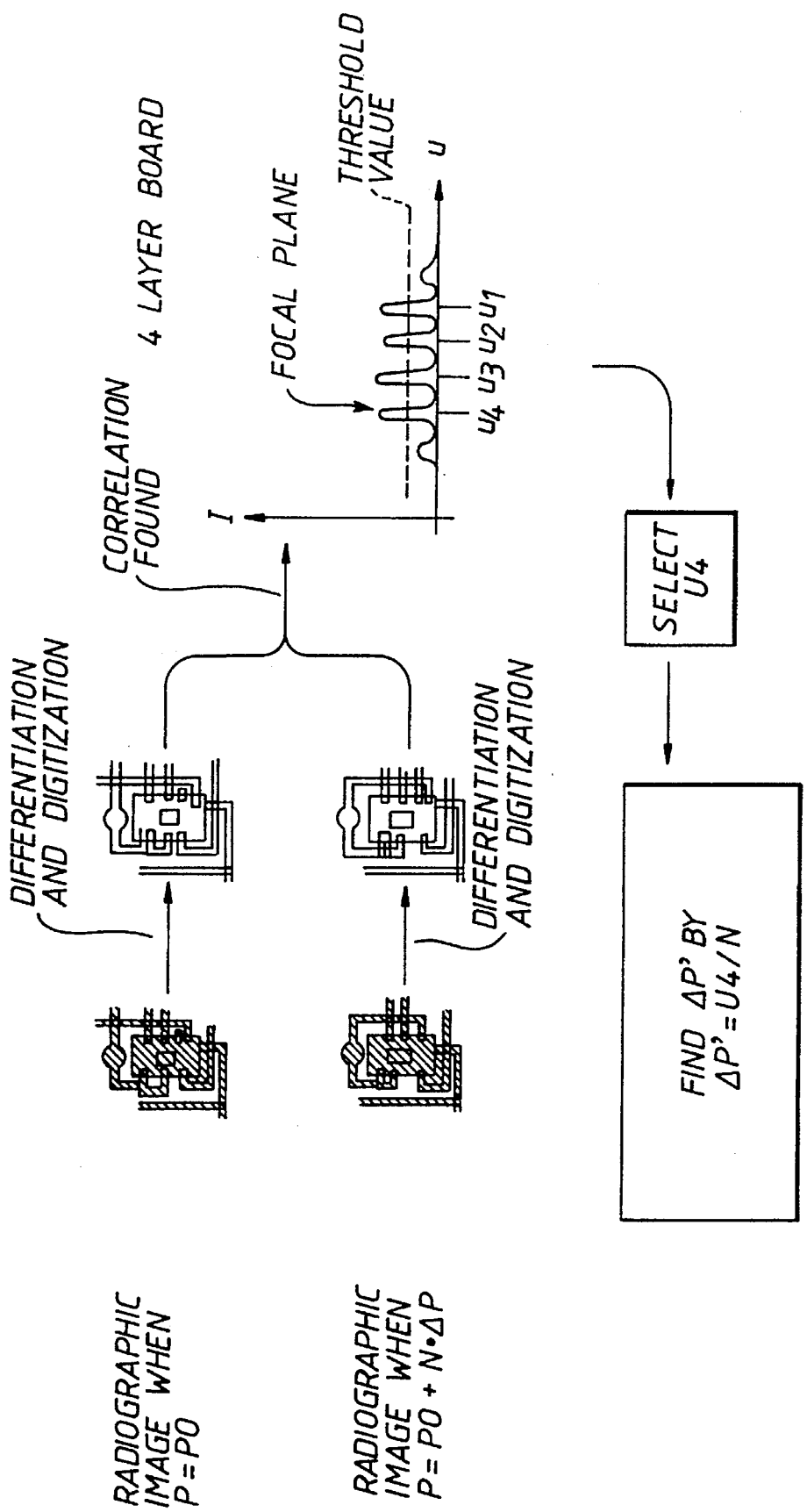
FIG. 23 is a view given in explanation of the operations of the laminograph shown in FIG. 20.
Figure 24:
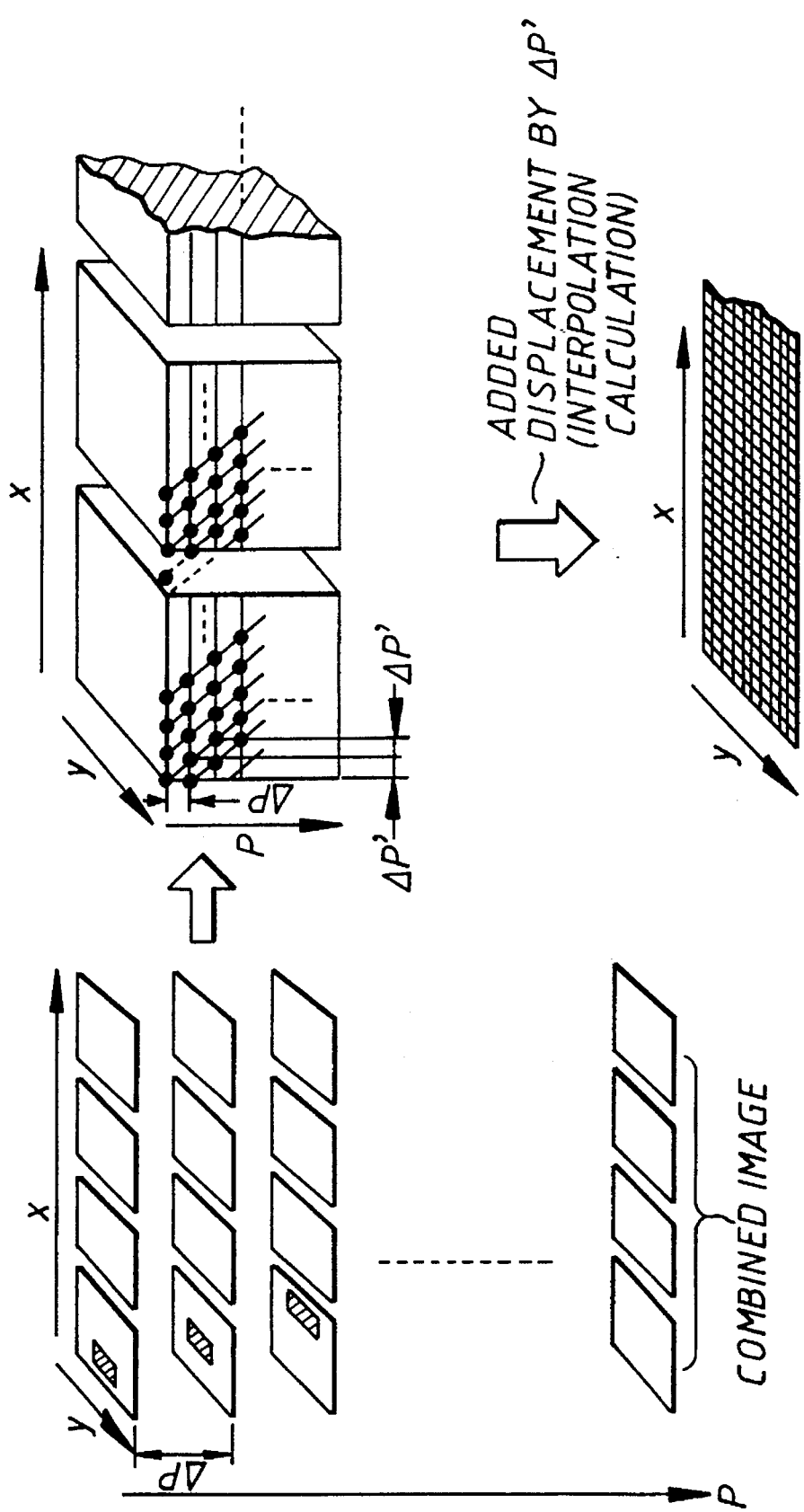
FIG. 24 is a view given in explanation of the operations of the laminograph shown in FIG. 20.

The two radiographic images thus selected, at two movement distances of Po and (Po+N·ΔP), are both subjected to differential (edge emphasis) and binary processing to obtain the outline-only images shown in FIG. 23. There are various ways of making correlations, but in the method adopted in this case, a logical calculation of corresponding pixels is performed and all resulting images are added together. The correlations of the inspection area alone were made as the image was displaced along axial direction x, and the peak of correlation value I for displacement u is detected.

In the case of a four-layer board, as shown in FIG. 23, four peaks appear corresponding to the pattern correlations of each of the layers. Displacement values u1, u2, u3 and u4 are found, which correspond to peaks in declining order from the highest value for displacement u as they come closer to X-ray tube 11. Two small peaks appear at outer sides of displacement peaks u1 and u4, and these are formed by the patterns within the electronic parts. These small peaks are cut by a threshold value and are not counted.

As described above, the peak corresponding to the smallest displacement value u4 found here corresponds to front outrage 14a of board 14.

Next, displacement ΔP' between neighbouring radiographic images, i.e. the change in movement distance ΔP', is found from displacement u4 by the following equation:

$$\Delta P' = u4/N \qquad (4)$$

If ΔP' is thus found, addition and averaging processing is next performed by image processing device 21. As shown in FIG. 24, the multiple images obtained by the detectors 13 in the same movement position P are arranged on plane x, y at the distances between detectors 13, to form a single combined image (if only one detector is used, the image obtained by the detector may be used without modification). At each change of movement ΔP, multiple combined images are arranged in the direction of P as shown in FIG. 24. Then the multiple combined images are displaced by displacement ΔP' along axial direction x and added and averaged (including linear interpolation).

Thus, the points on the inspection plane, which is the upper layer of board 14, that is focal plane, are overlaid each other at the same position and are emphasized, whereas the points not on this plane are overlaid at a distance from each other and are not noticeable. A tomographic image which is a radiographic image focused on the top layer of board 14 is thus obtained.

In the embodiment described above, it is possible to improve statistical accuracy by obtaining ΔP' such that based on multiple sets of radiographic images with different values Po and N a multiple values for ΔP' are obtained and ΔP' is then found by their average.

In the embodiment described above, by applying micro-correction terms to ΔP', it is possible to set the focal plane position slightly higher (or lower) than the top layer (or the bottom layer) of board 14. It is thus possible to take the thickness of the solder into account and to locate the focal plane well on the solder.

It is also possible to find correlations between individual radiographic images and a standard radiographic image and find the displacements. In such cases, there is no necessity for data collection pitch ΔP to be uniform; it may even be a completely unknown value.

In the above embodiment, it is possible to obtain a tomographic image focused on the inspection plane even when the board is curved. It is also possible to obtain a tomographic image focused on the inspection plane without adjustment even if the thickness of the board changes, or the attachment of the board clamp 19 is poor and the inspection plane moved. Furthermore, it is possible to obtain a tomographic image focused on the inspection plane when the mechanical positional relationships are displaced (i.e. when they are unadjusted).

In the embodiment described above, it is possible to focus on the inspection plane from the radiographic images only, and thereby to obtain a tomographic image focused on the inspection plane, without using any optical or mechanical means of measuring the position of the board plane or adjusting the board position.

FIG. 25 shows the operation of a laminograph according to a tenth embodiment of this invention. The structure of the laminograph in this tenth embodiment is the same as that of the ninth embodiment shown in FIG. 20.

In contrast to the ninth embodiment in which focusing is performed using the wiring pattern on the board, this tenth embodiment focuses using the solder pattern.

Figure 25A:
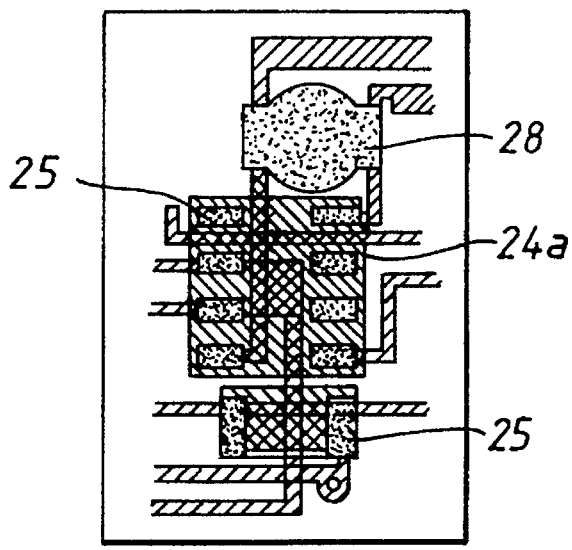
FIGS. 25a and 25b are views given in explanation of the operations of a tenth embodiment of a laminograph according to the invention.
Figure 25B:
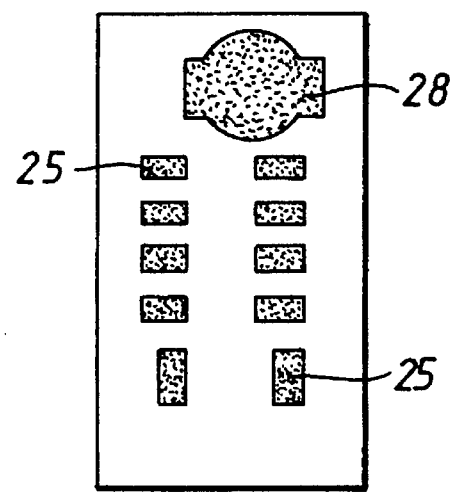

From the radiographic image shown in FIG. 25(a), it is clear that the solder parts 25 are higher in density. This embodiment uses the high-density solder parts 25 to digitize these for producing the image shown in FIG. 25(b). In FIG. 25, 28 is a capacitor and 24a is the IC being inspected.

Figure 25C:
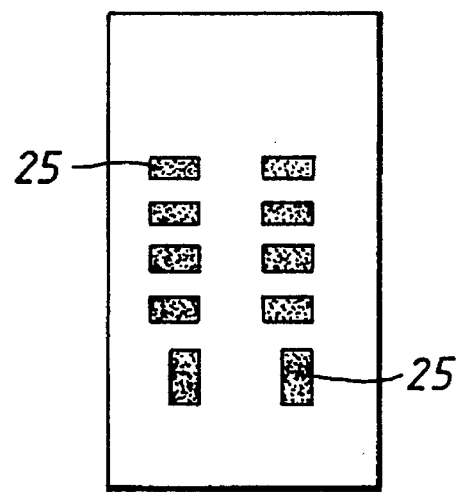

The wiring patterns are removed from the image shown in FIG. 25(b) but the parts, such as capacitor 28 etc, strongly absorbed remain. Next, each link of parts with low digitized level (black in the figure) is labelled and the area of each label is found, using the histogram function of the image processing. The image shown in FIG. 25(c) is obtained by removing the labelled part with the large area. Thus solder pattern only is obtained.

Figure 26:
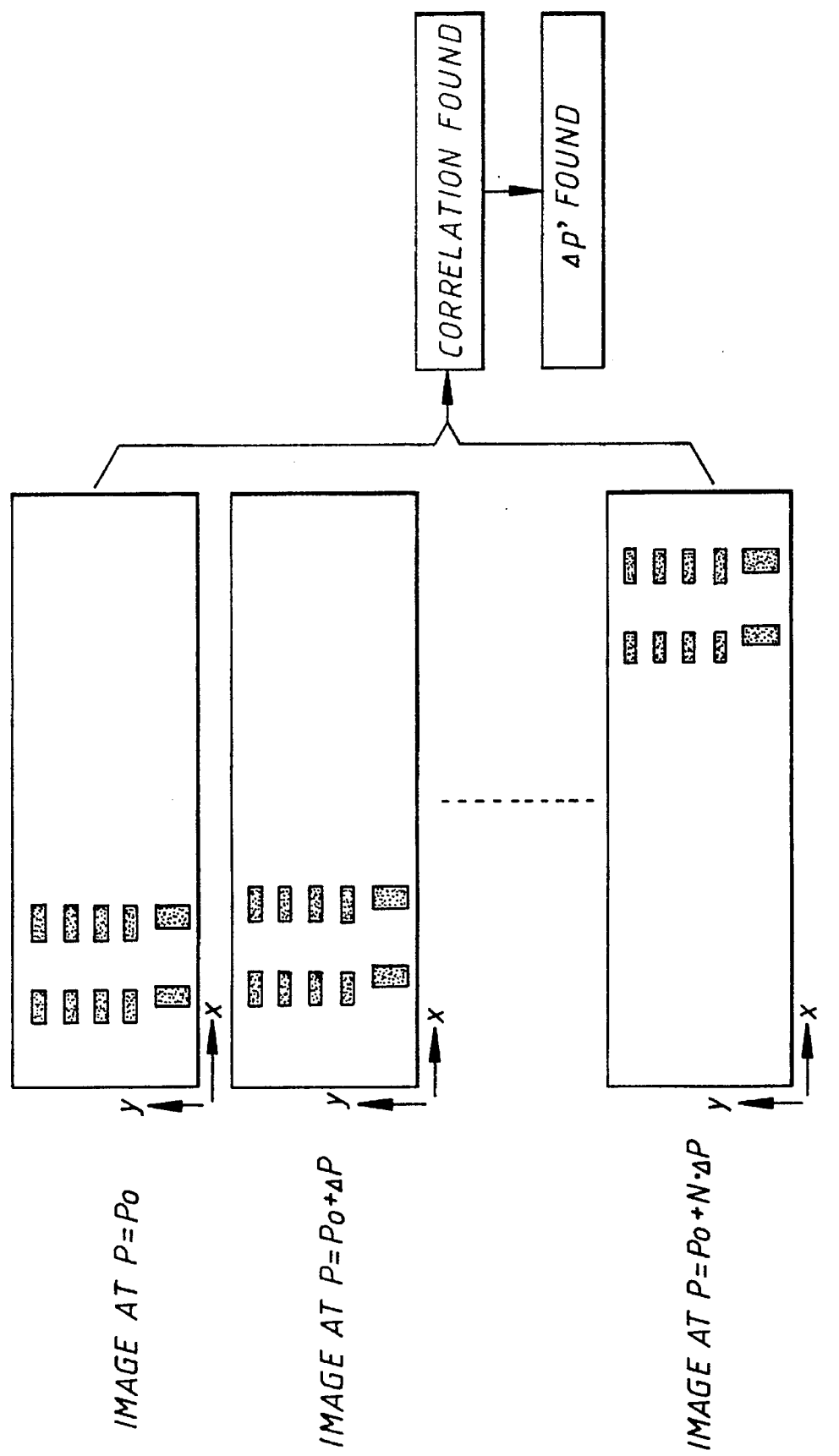
FIG. 26 is a view given in explanation of the operations of the laminograph shown in FIG. 25.

As shown in FIG. 26, correlation is taken between images thus prepared in which sweeps P=Po and P=Po+N·ΔP. Then displacement ΔP' is found in the same way as in the ninth embodiment. A tomographic image is obtained by subsequent processing in the same way as in the ninth embodiment.

In this embodiment, focusing is performed using the direct solder pattern, and focusing is possible without being influenced by the state of the circuit pattern and with few malfunctions. Also it is possible to omit differential processing and other time-consuming processes and thus to shorten the processing time.

In the tenth embodiment, as in the ninth embodiment, it is possible to improve statistical accuracy by finding ΔP' from multiple sets of radiographic images with different values of Po and N and averaging these. It is also possible to finely adjust the focal plane by applying micro-adjustment terms to ΔP'. It is further possible to find correlations between these individual radiographic images and a standard image and thus find individual displacements by the correlations thus found.

Figure 27:
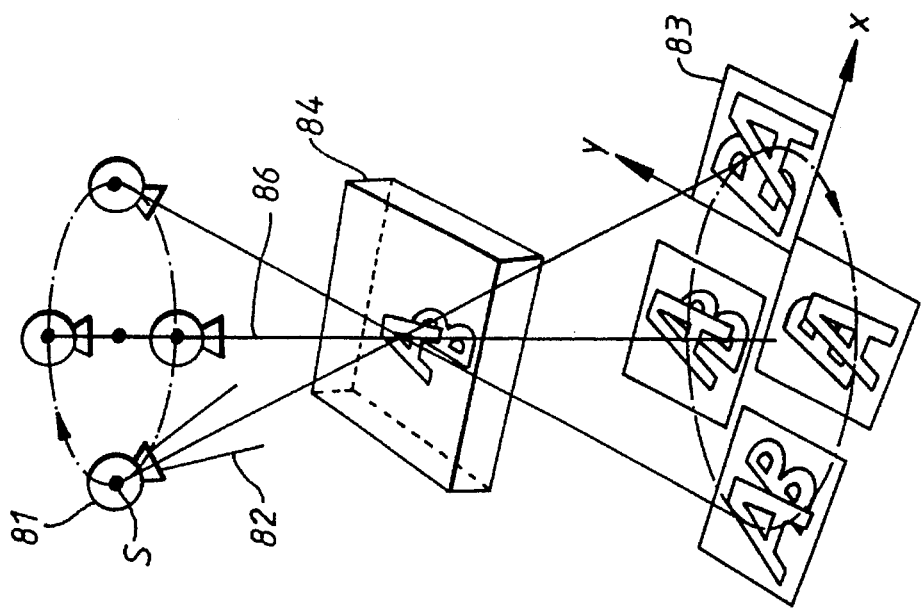
FIG. 27 is a view showing an eleventh embodiment of a laminograph according to this invention.

FIG. 27 shows an eleventh embodiment of a laminograph according to this invention. In this eleventh embodiment, an X-ray tube 81 with an X-ray focal spot S, and a detector 83 which is X-ray plane sensor, face each other with a board 84 that is the subject between them, and both of these are rotated in synchronism around an axis of rotation 86. In FIG. 27, 82 is an X-ray beam output form X-ray tube 81.

In this embodiment, detector 83 which is X-ray plane sensor, is rotated around axis of rotation 86, on a plane of rotation which is parallel with the measurement plane shown as plane xy, maintaining its azimuth constant, and radiographic images of the subject are obtained during the rotating scan.

Figure 28:
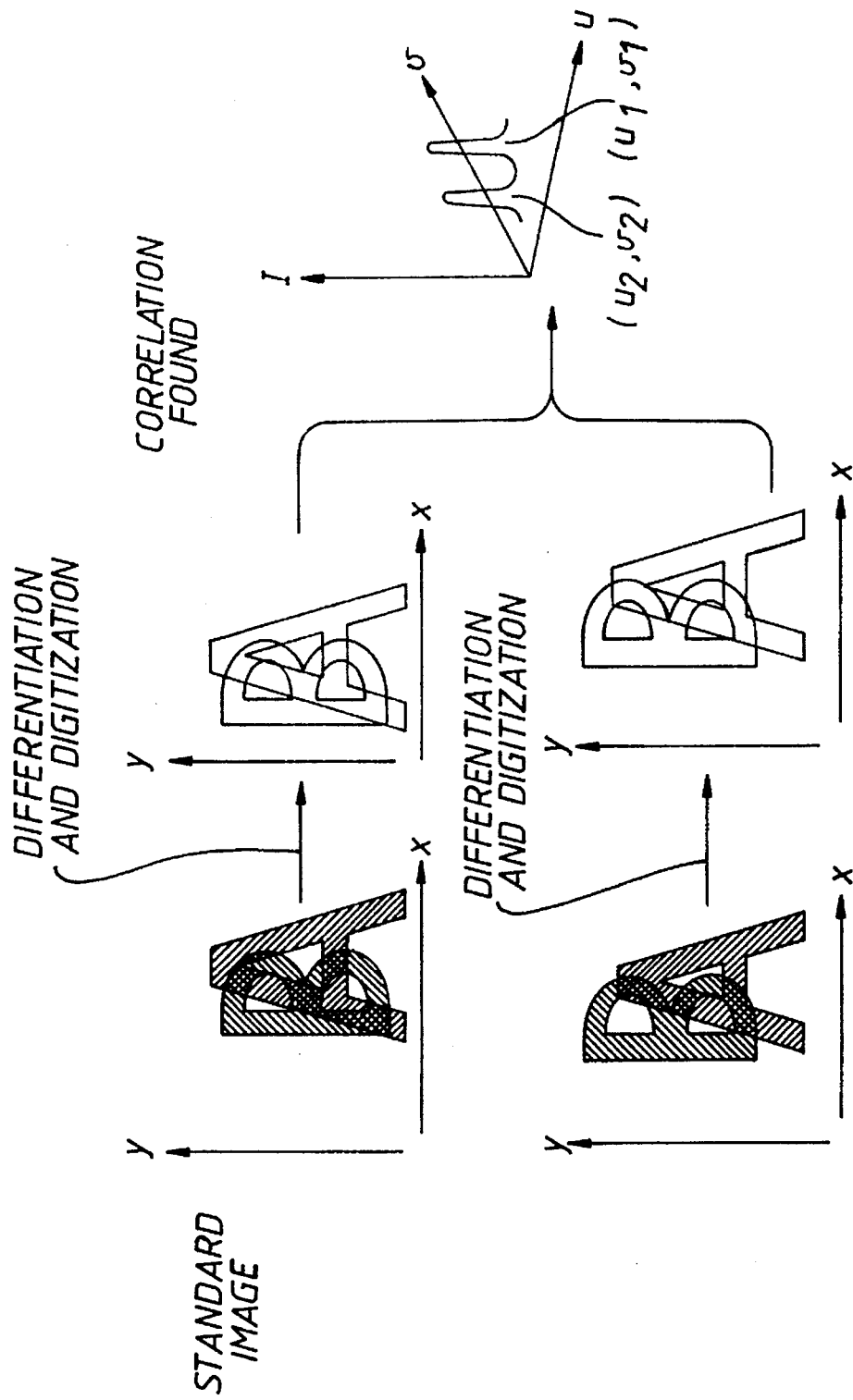
FIG. 28 is a view given in explanation of the operations of the laminograph shown in FIG. 27.

In this embodiment, as shown in FIG. 28, the image processing means differentiates and digitizes the various radiographic images. With displacing them along axial direction x, y, it finds correlations between a standard radiographic image and them. Correlation value I becomes large when the pattern match. When there are two layers of patterns in board 84, peaks of correlation values I are formed at two places, at displacement u in axial direction x and displacement v in axial direction y: (u1, v1) and (u2, v2). The peak produced when displacement $(u2+v2)^{1/2}$ is larger is due to the pattern of a layer close to X-ray tube 81 and the peak produced when this is smaller is due to the pattern of a layer further away.

In the embodiment shown in FIGS. 27 and 28, when pattern A of the upper layer of board 84 which is the subject is focused upon, the larger displacement (u1, v1) is selected. Radiographic image focused on upper layer A, that is a tomographic image, can be obtained by finding the displacement for each radiographic image in the same manner and by adding and averaging the radiographic images.

Figure 29:
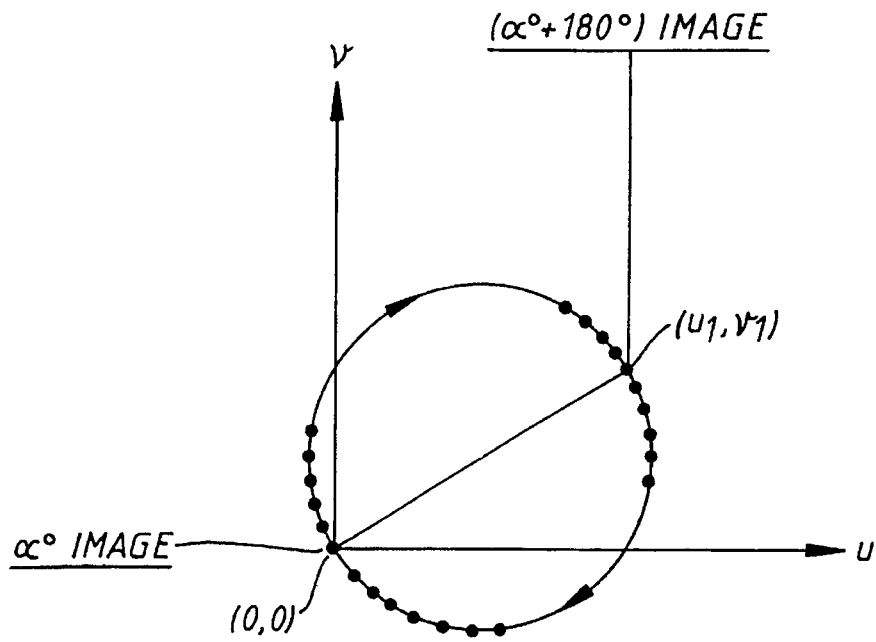
FIG. 29 is a view given in explanation of the operations of the laminograph shown in FIG. 27.

When radiographic image collection is performed for each time the rotation angle step is the same, there is no need for the above-described correlation to be found for all radiographic images. As shown in FIG. 29, an α° image is taken as standard and correlations are found between this and an (α°+180°) image which is separated from α° image by 180°, and the displacement (u1, v1) is then obtained. In subsequent processes, the displacement (u, v) can be found if a circle with the radius (0, 0)–(u1, V1) is drawn and it is assigned for each collection angle pitch, as shown in FIG. 29.

Also, as in the ninth and tenth embodiments, it is possible to improve statistical accuracy by preparing sets of correlations, and by averaging them to find the displacement. It is also possible to make fine adjustments of the focal plane by slightly changing the radius of the displacement circle concentrically.

FIG. 30 shows a twelfth embodiment of a laminograph according to this invention. The structure of the laminograph in this twelfth embodiment is the same as that of the ninth embodiment shown in FIG. 20. In the ninth embodiment, displacement is found by finding correlation between radiographic images. But in the twelfth embodiment, displacement is found by finding correlation between the radiographic image and a board pattern obtained as previously set data.

Figure 31:
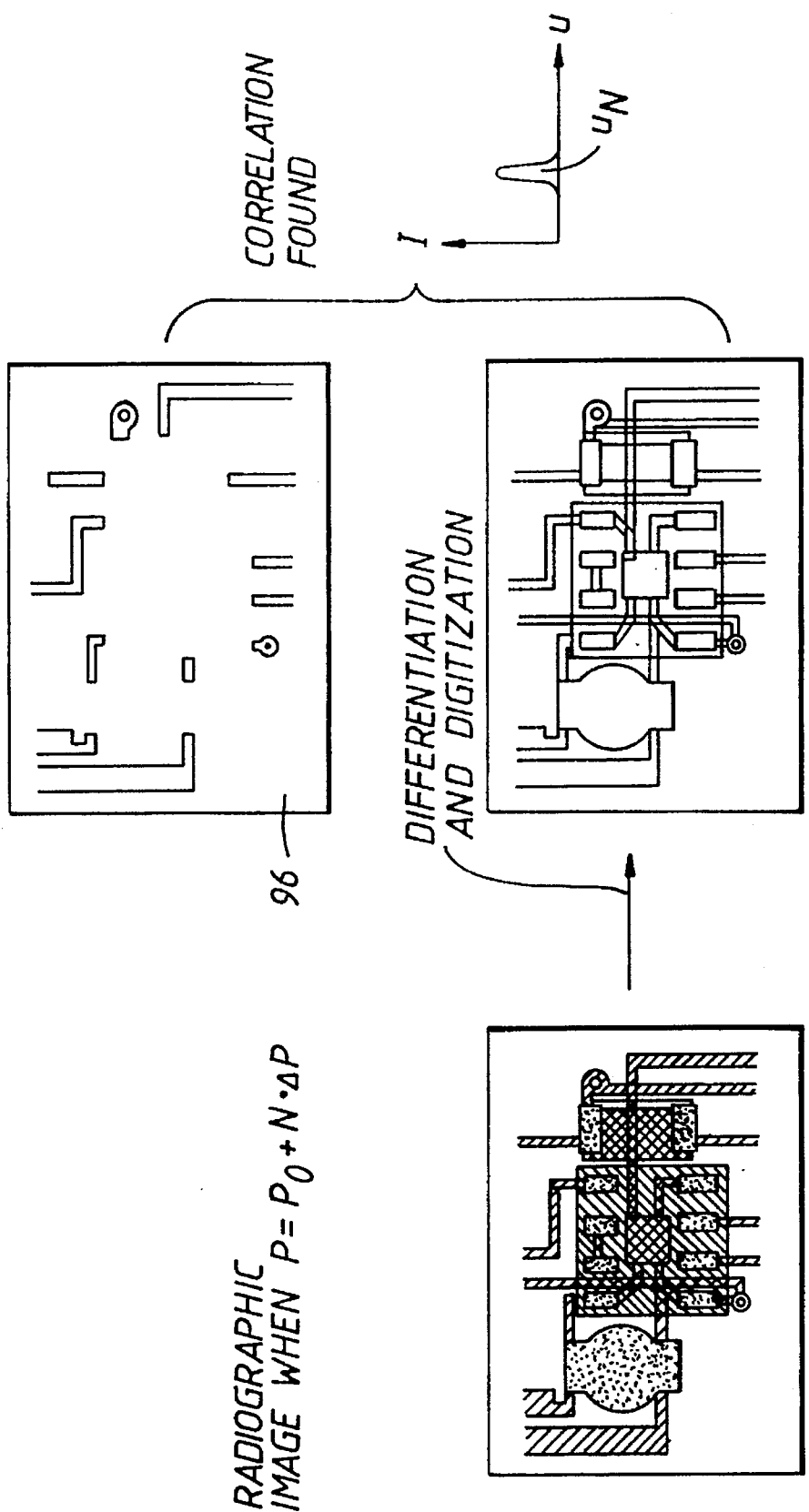
FIG. 31 is a view given in explanation of the operations of the laminograph shown in FIG. 30.

Thus, correlation is found between a surface pattern 96 of the board according to CAD data shown in FIG. 30 and a radiographic image obtained by differentiating and digitizing a radiographic image when P=Po to find displacement uN which gives a peak value with correlation value I. Also, correlation is found between surface pattern 96 of the board according to CAD data shown in FIG. 31 and a radiographic image obtained by differentiating and digitizing a radiographic image when P=Po+N·ΔP to find displacement uN which gives a peak value with correlation value I. Displacement ΔP', between neighbouring radiographic images, is found from displacements uo and uN thus found, using the following equation. It is possible to obtain a tomographic image focused on the desired board pattern by adding and averaging the radiographic images, with each displaced by ΔP'.

$$\Delta P' = (uN - uo)/N$$

In this twelfth embodiment, as a large peak due to correlations is generated in only one place, the displacement is found with accuracy. This embodiment, therefore, can easily be used for mounted boards with a complex combination of parts and patterns on upper and lower layers of the board.

In this twelfth embodiment, it is possible to obtain a tomographic image focused on the inspection plane even when the focal spot of the X-ray is displaced.

The laminographs according to the ninth through twelfth embodiments described above can, of course, be applied to the scanning type laminograph shown in FIG. 15 and FIG. 16.

Figure 32:
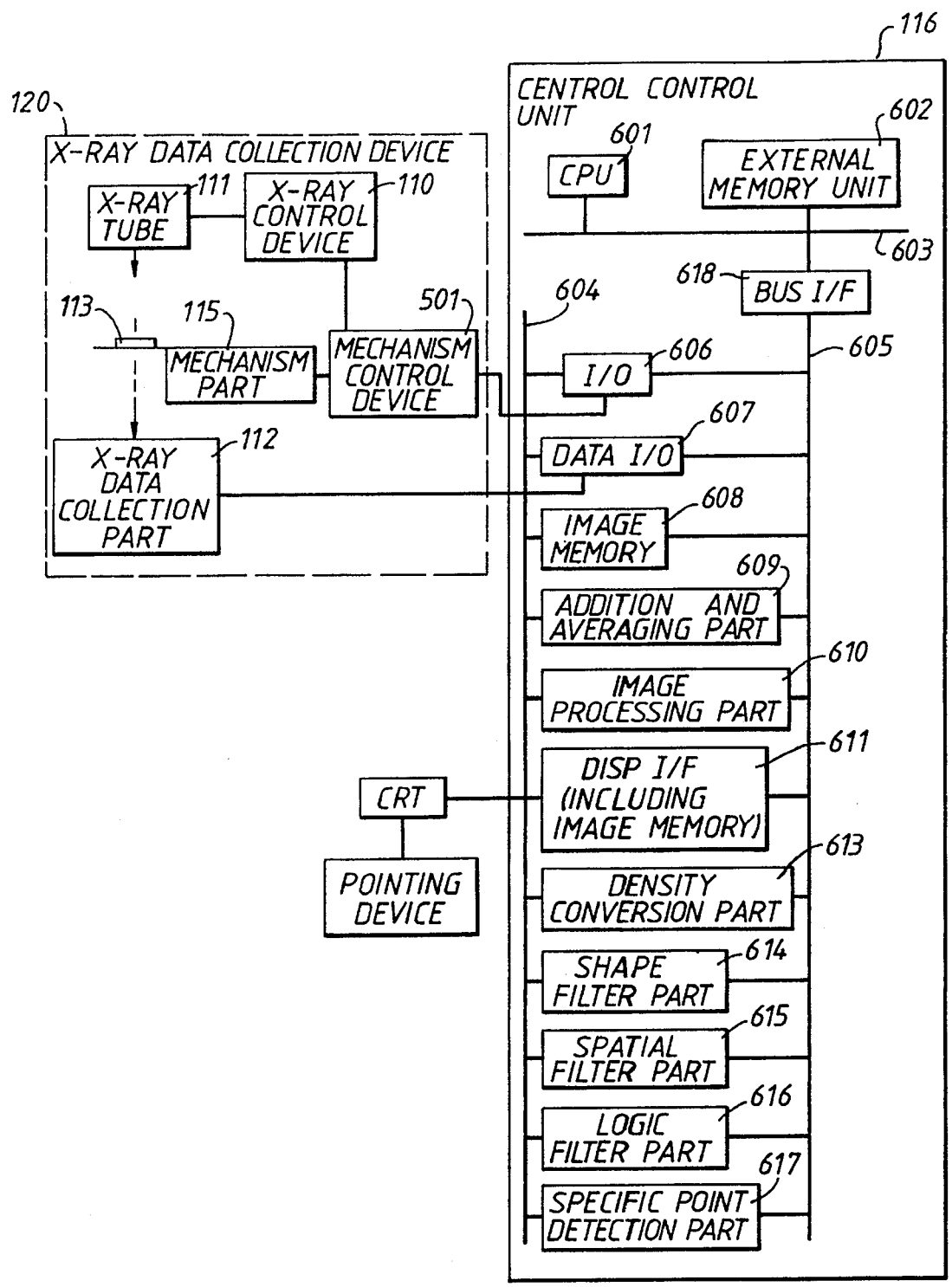
FIG. 32 is a block diagram showing the structure of a thirteenth embodiment of a laminograph according to this invention.

FIG. 32 shows a thirteenth embodiment of a laminograph according to this invention.

In each of the embodiments described above, radiographic images obtained from multiple different directions are overlaid so that they overlap only on the focal plane, and the images other than on the focal plane are blurred so that a tomographic image is obtained only on the focal plane. However, when there is any image other than on the focal plane which is more dominant in terms of density than the image which exists on the focal plane, there is the problem that the S/N ratio of the obtained tomographic image deteriorates. In order to improve the S/N ratio, that is, to mask information from except the focal plane, it is necessary to have many images with larger angle and more directions. As a result, there is a problem that data collection becomes more difficult and complex, and it takes the consumption of mote time.

In order to solve the above-described problems, in the thirteenth embodiment, the S/N ratio of the image on the focal plane is improved by performing pre-processing in the image restoration processing. Also it is possible to obtain many lamino images (tomographic images) in the depth direction and these images can be displayed in three dimensions.

The basic principle of the thirteenth embodiment of the laminograph will be explained as follows. It is possible to anticipate the density range of the image on the focal plane, and when pixels with an image density greater or lower than the anticipated density are present at the radiographic image stage, these pixels are data converted, and their effect on the added image thus moderated. It is also possible to anticipate beforehand the shape of the elements composing the image on the focal plane, and when there is an image with the shape other than that anticipated at the radiographic image stage, the image is data converted in terms of density or shape, and the effect on the added image is moderated. Also, multiple lamino-images are image-enhanced and added to display a single image, thus making it possible to have an effective overall view of the subject.

The structure of this embodiment is now described with reference to FIG. 32. The embodiment of the laminograph shown in FIG. 32 has an X-ray data collection device 120 which is composed of an X-ray tube 111 which projects X-rays towards the subject, an X-ray control device 110 which controls X-ray tube 111, an X-ray data collection part 112 including X-ray detectors fitted to face X-ray tube 111, with subject 113 between them, a mechanism part 115 which moves subject 113, and a mechanism control part 501, which controls X-ray control device 110 and mechanism part 115. The laminograph further has a central control unit 116 connected to X-ray data collection device 120, a CRT 612 connected to central control unit 116, and a pointing device 6121.

Central control unit 116 carries out image processing such as receiving X-ray data from X-ray data collection device 120 and operating laminographically to produce composite tomographic images etc. central control unit 116 has a CPU 601 which controls all operations, an external memory unit 602, an I/O interface 606, a data I/O interface 607, an image memory 608, an adding and averaging part 609, an image processing part 610, a display interface 611, a density conversion part 613, a shape filter part 614, a spatial filter part 615, a logic filter part 616, a specific point detection part 617 and buses 603, 604 and 605 which connects all of these parts.

In this embodiment, radiographic images are obtained when subject 113 is moved in the field of X-ray transmission in parallel to the detection plane of X-ray data collection part 112, and a lamino image is reconstructed based on radiographic images thus obtained.

When subject 113 moves all points of subject on a focal plane which is parallel to the direction plane, shift on the radiographic image with same shift amount determined by the position of movement. Only information for the focal plane is accumulated by adding the radiographic images after the shift (displacement) is given to each radiographic image with said displacement, and this blurs other images.

Figure 33:
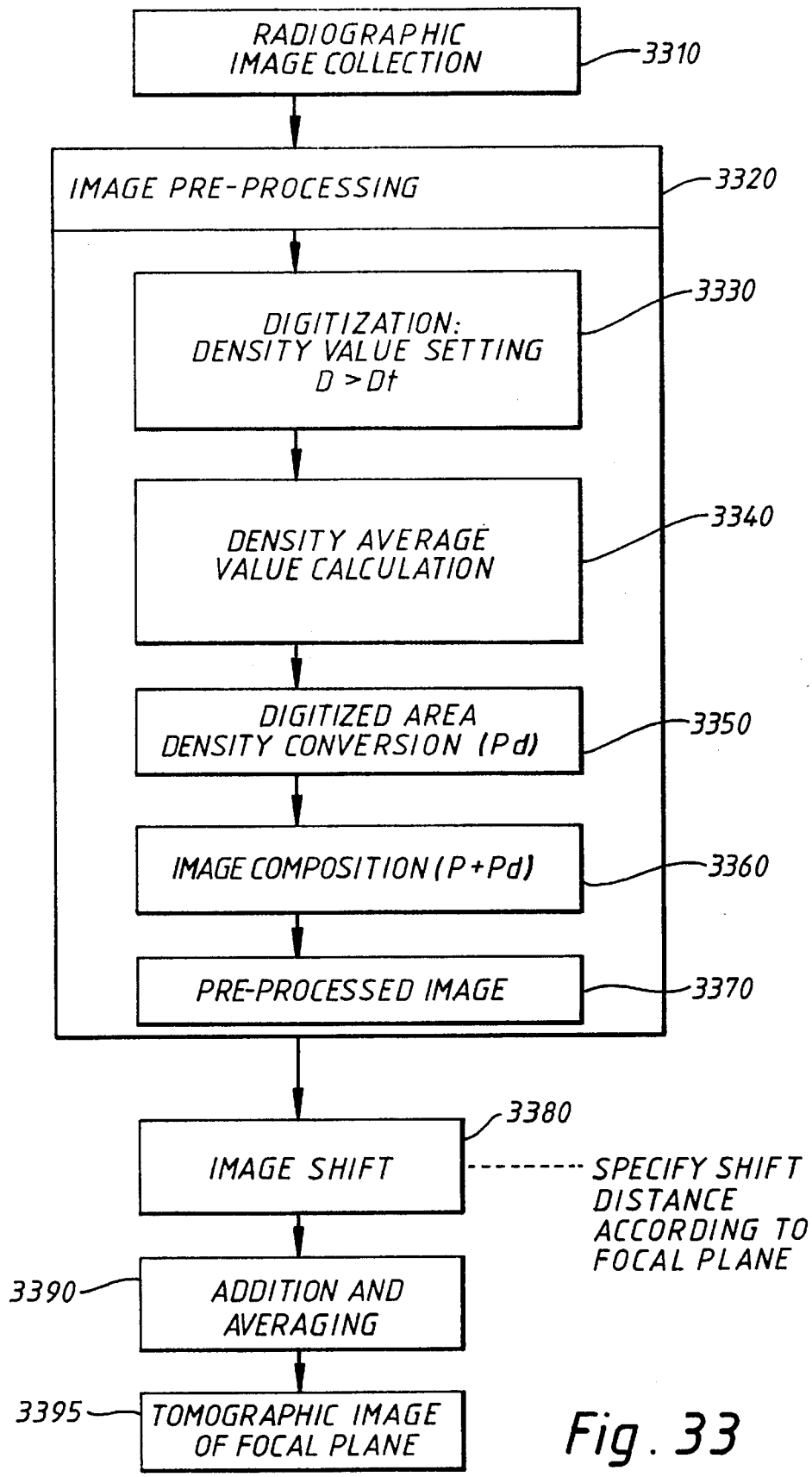
FIG. 33 is a flow chart showing the operations of the laminograph shown in FIG. 32.

Next, the operation of the laminograph shown in FIG. 32 is described with reference to the flow-chart shown in FIG. 33. In FIG. 33, a radiographic image is collected (step 3310), this radiographic image is pre-processed (step 3320) and then lamino processing is carried out (steps 3380, 3390, 3395). The pre-processing in step 3320 consists of extracting areas with higher density D than a specified threshold value Dt from the radiographic image and digitizing these (step 3330). Then, the average density value of the entire image is calculated (step 3340), the density of the extracted areas is substituted by the average value Pd (step 3350), and a pre-processed image after completion of pre-processing is obtained (step 3370) by image composition (step 3360), i.e. Pd at extracted area and original image at not extracted area. This pre-processing is suitable for a tomographic image of a subject which is preknown to have no portions with large X-ray absorption on the focal plane so as the reduce the effect of portions with large X-ray absorption on other planes.

After completion of pre-processing, image shift (step 3380) and addition and averaging processing (step 3390) are performed on the pre-processed image, and a tomographic image on the focal plane is thus obtained (step 3395). This embodiment is effective in case when a low probability of a high density image being present on the focal plane is anticipated. When no prediction can be made concerning the quality of the image on the focal plane, the image data of the extracted areas is converted to the weighted average density. In step 3330, image areas are extracted having a larger density D than density threshold value Dt. But it may be preferable to extract areas whose density is less than Dt or whose density is in a density band, depending on the character of the image on the focal plane.

The above-described pre-processing is performed to improve the S/N ratio of the image on the focal plane. There are many kinds of other pre-processing.

Figure 34:
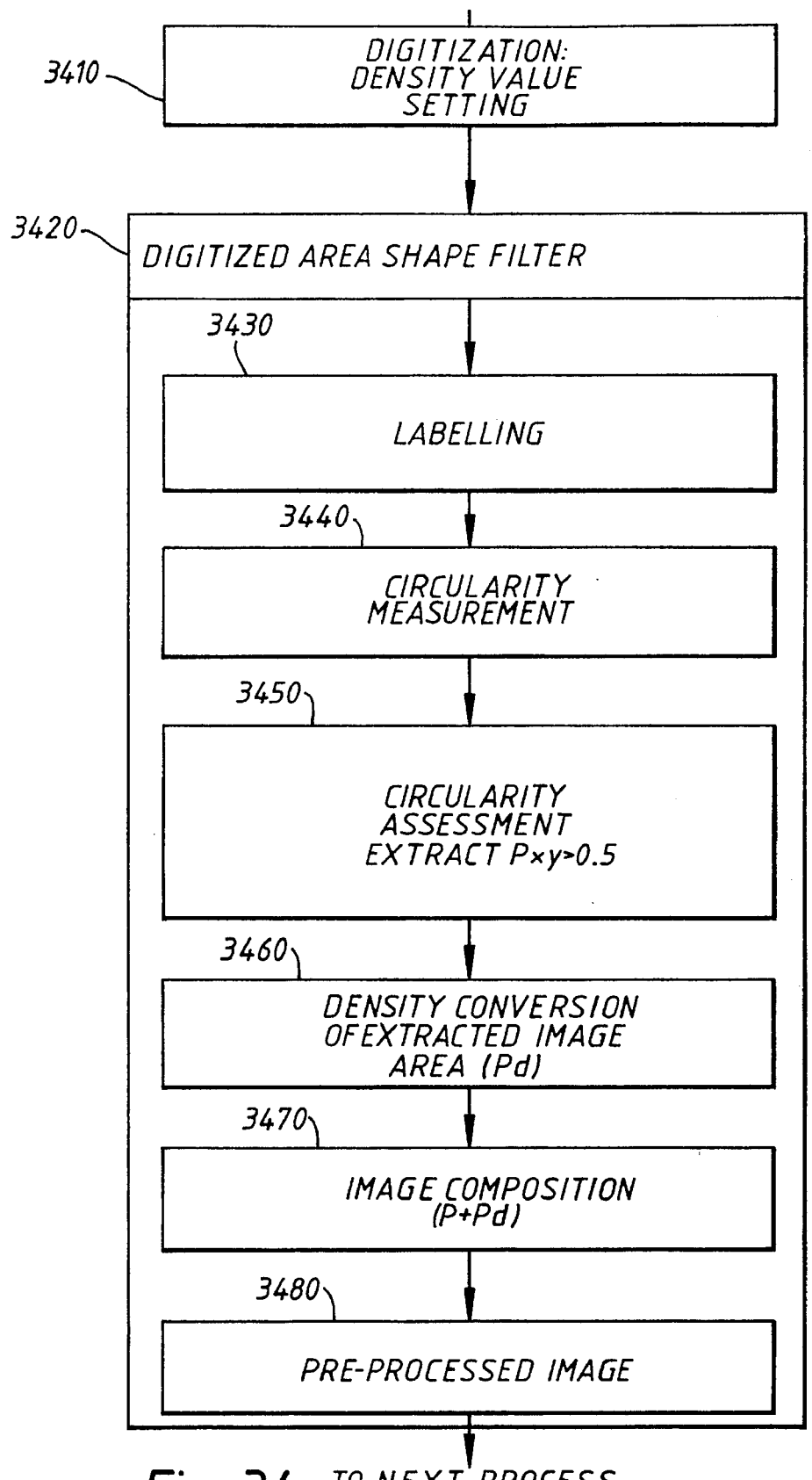
FIG. 34 is a flow chart showing the processes using a shape filter as pre-processes in the laminograph shown in FIG. 32.

FIG. 34 shows an example of pre-processing wherein a shape filter is used and the process is principally carried out by shape filter part 614 in central control unit 116.

In the process shown in FIG. 34, first, digitization (conversion to binary image) is carried out to extract the image on which shape-processing is to be performed (step 3410). Then, extracted area shape filtering is performed on this binary image (step 3420). In this process, the extracted areas are labelled (step 3430), and a subject of processing is confirmed. Next, the circularities Pxy of the extracted areas are measured (step 3440). Areas Pxy having a larger value of Pxy than the specified circularity threshold value is extracted (step 3450), and this extracted areas are density converted (step 3460) and composed (step 3470). The following processes are carried out as lamino processing on the pre-processed image thus subjected to addition processing (step 3480). For density conversion, density is converted to the average density value of the entire image of local points of the value of neighboring pixels, etc.

Figure 35A:
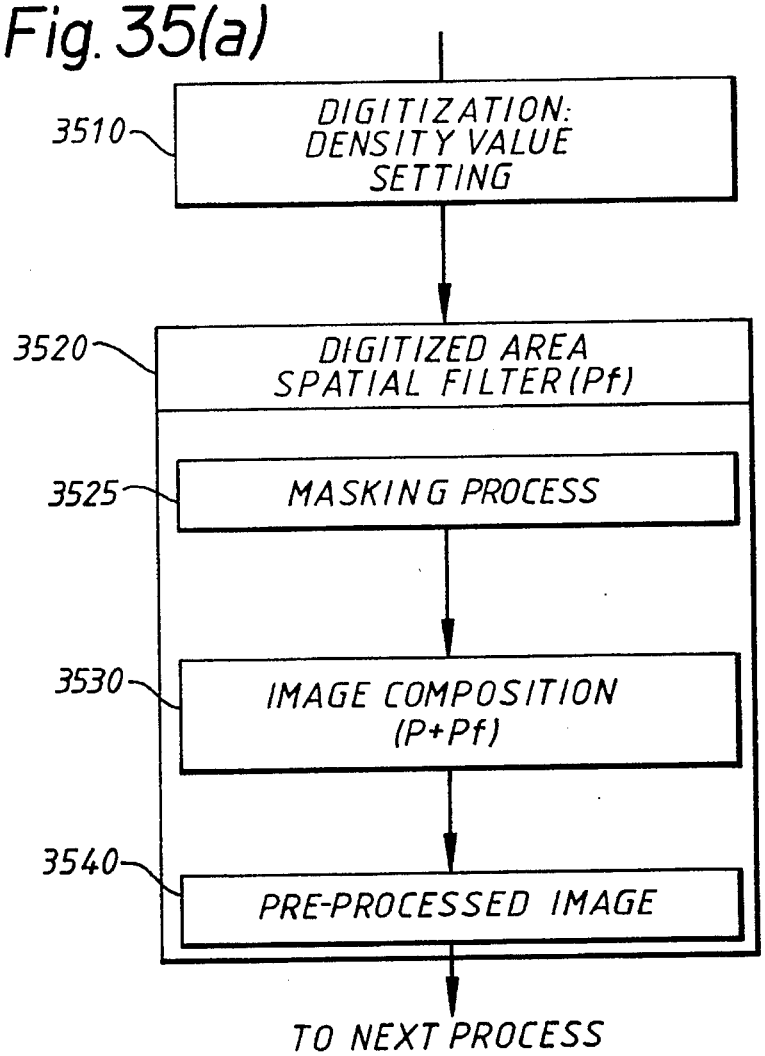
FIGS. 35a and 35b are a flow chart showing the processes using a spatial filter as pre-processes in the laminograph shown in FIG. 32.
Figure 35B:
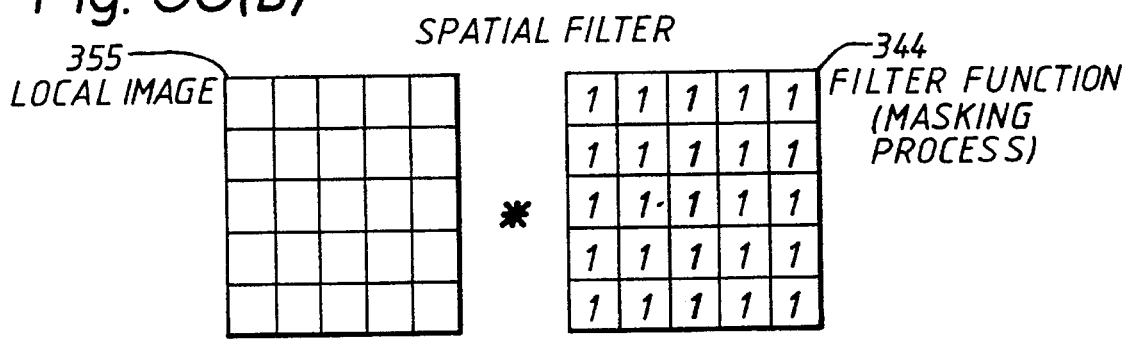

FIG. 35 shows another example of pre-processing in which a spatial filter is used and this processing is mainly performed by spatial filter 615 in central control unit 116.

In the process seen in FIG. 35(*a*), a filter function is used (step 3525) on the original images in the extracted areas by digitization (step 3510). FIG. 35(*b*) shows one example of such a filter function 344. This performs masking processing with a 5×5 matrix. After the filtered images of the extracted areas and original image of other areas have been composed, this is taken as a pre-processed image (steps 3530 and 3540). The following processes are carried out as lamino processing on the pre-processed image.

The pre-processings described above are often more effective when used in combinations. An image processing means performs processes including image density processing, image shape processing, spatial frequency processing in desired areas, logic filtering, inter-image algorithms, morphological processing etc., which can emphasize, weaken or delete the characteristics of the radiographic image.

Pre-processed images are taken as regular radiographic images, and as shown in steps 3380 and 3390 of FIG. 33 image shift and addition and averaging processing are performed and a tomographic image of the focal plane is obtained (step 3395). These processes are specified in advance and are automatically executed while incorporating radiographic images.

Next, the overall functions of the laminograph shown in FIG. 32 are described. While subject 113 is moved by mechanism part 115, X-rays radiated from X-ray tube 111 pass through subject 113 and are acquired as radiographic images by X-ray data collection part 112, and radiographic images in many directions are thus obtained during this movement. The radiographic data is fed to image memory 608 of central control unit 116 via data I/O interface 607. The processing in which extracted area is cut out and the characteristic parameters of the shape are measured, and spatial filtering and other processings are performed by image processing part 610. Radiographic images are added with shifts according to the focal plane and averaged by addition and averaging part 609 to obtain a tomographic image on the desired focal plane which is parallel to the detection plane.

Figure 36:
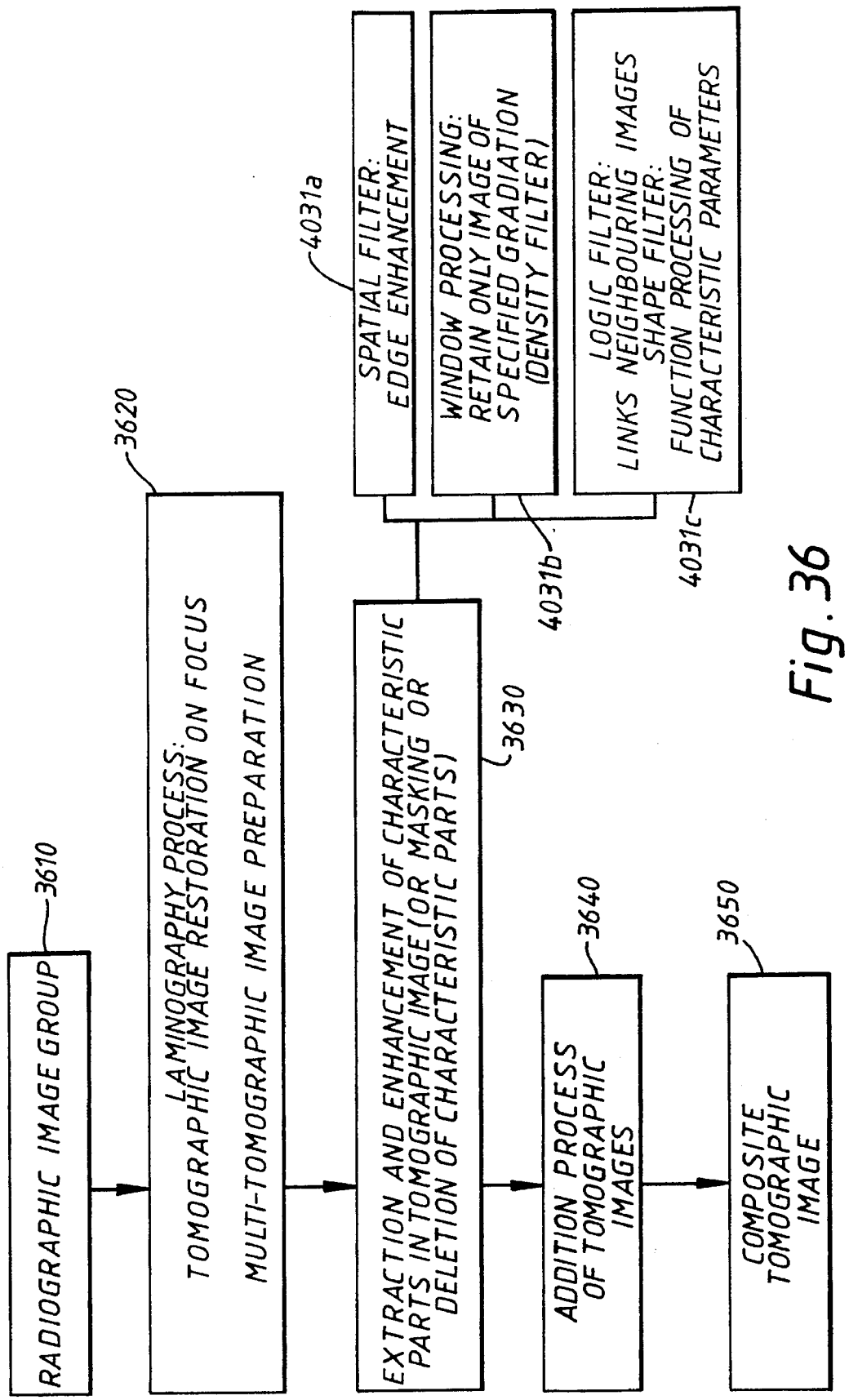
FIG. 36 is a flow chart showing the operations of the laminograph shown in FIG. 32.
Figures 37A, 37B, 37C:
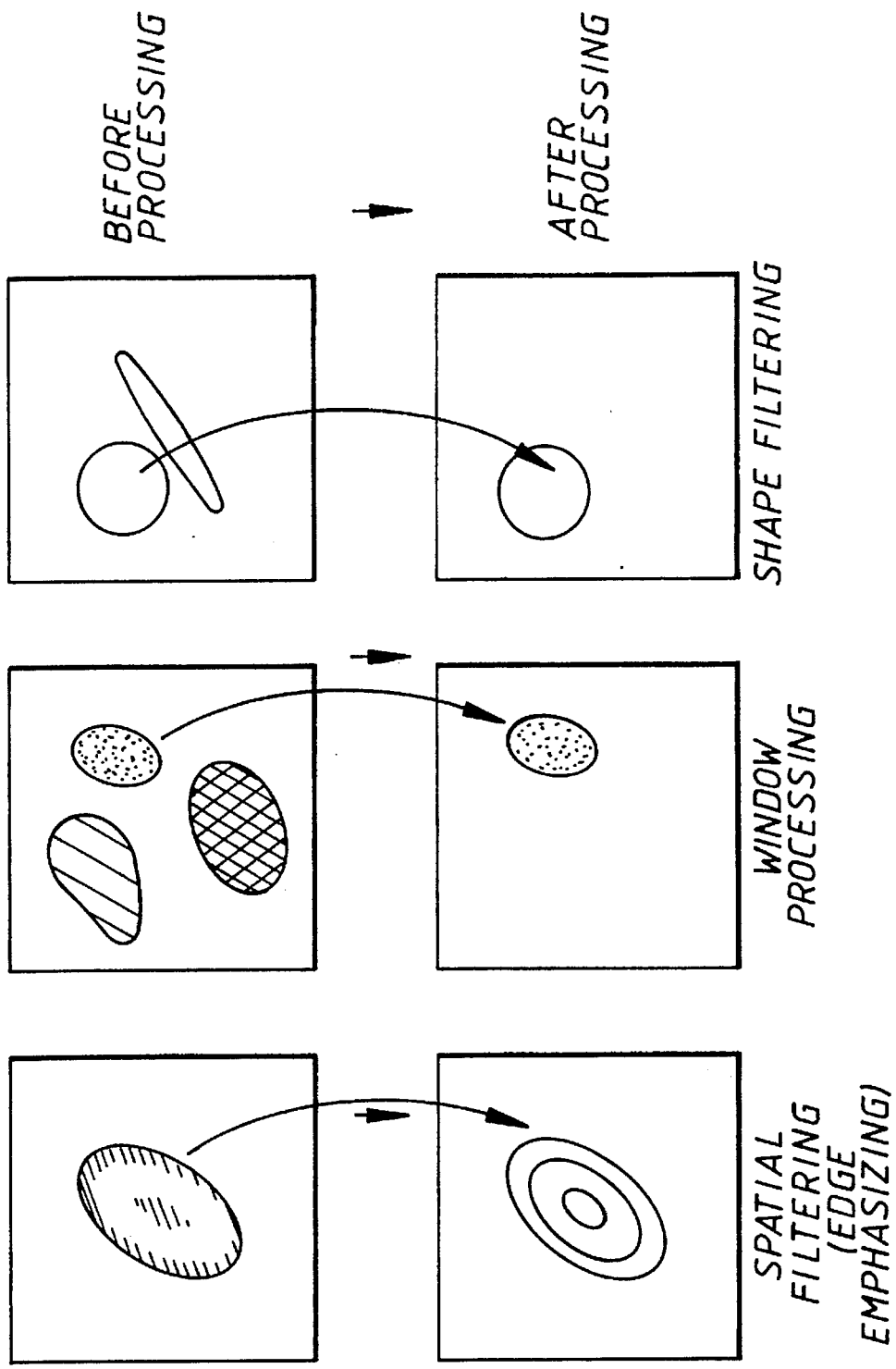
FIGS. 37a–37c are views showing the image display processing device (lamino image processing device) used in the processes shown in FIG. 36.

Next, the display of the completed lamino image is described with reference to FIGS. 36 and 37. In the processes in FIG. 36, it is possible to move the focal plane of the lamino image by changing the shift amount. Lamino images with planes of different depth are obtained from radiographic images obtained by a single scanning operation (steps 3610 and 3620). The characteristic points of the lamino images are extracted or emphasized according to the purposes for which the lamino image is being examined (step 3630). Examples of this process are shown in steps 4031*a*–*c* and FIG. 37. Edge emphasizing is carried out by spatial filtering when the shape of the image is important, (step 4031*a* and FIG. 37(*a*)). Desired density areas are extracted by window processing (density filtering) when density is important (step 4031*b* and FIG. 37(*b*)). Logic filtering and shape filtering (step 4031*c* and FIG. 37(*c*)) may be used to characterize the images for other purposes. The image processing means performs processes including image density processing, image shape processing, spatial frequency processing in desired areas, logic filtering, inter-image processing, morphological processing etc.

When processing of adding images is performed on the processing-completed images, composite lamino image is obtained, which give desired information once as a single image (steps 3640 and 3650). In order to improve visibility of the image, some weighting may be given to images along with the simple addition.

Figure 38:
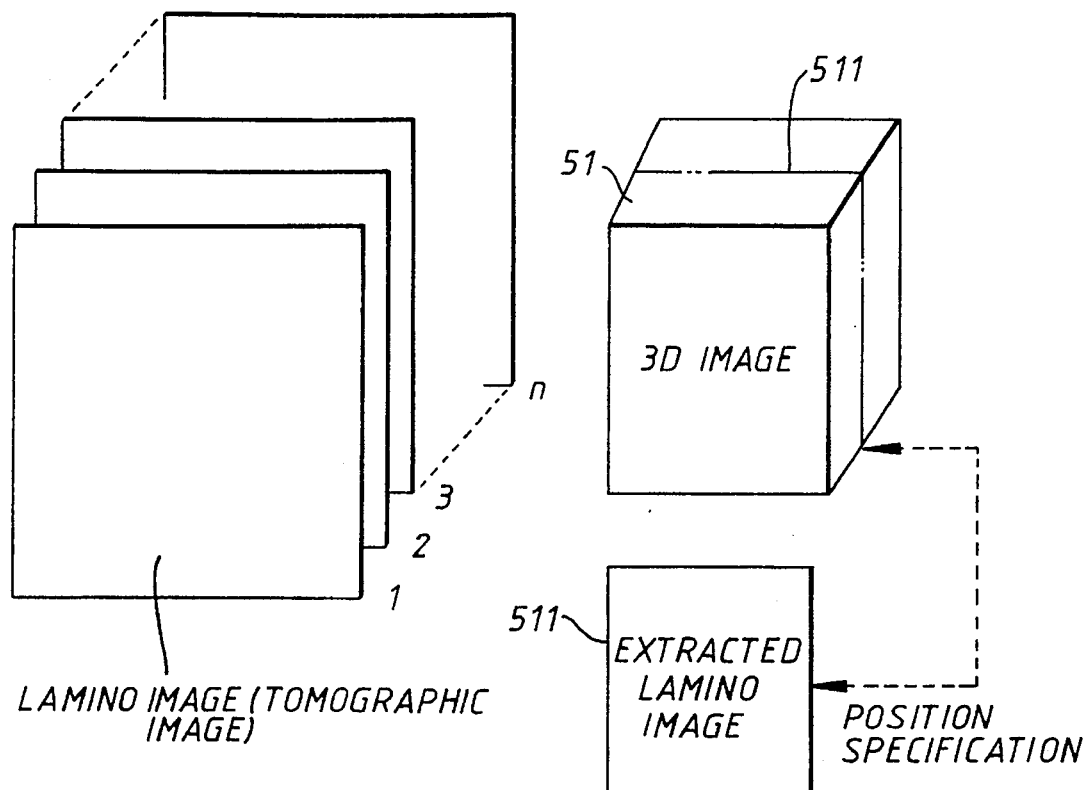
FIG. 38 is a view showing the three-dimensional display in the laminograph shown in FIG. 32.

FIG. 38 shows one example of a three-dimensional image display. Three-dimensional image is made possible by displacing and overlapping lamino images in the depthward direction. The necessary information is displayed three-dimensionally, by the above-described image enhancement of each image. It is also possible to have semi-transparent display when the image density is weighted according to depthward position. Three-dimensional display itself may be known by any of the many known methods. Besides the above-mentioned semi-transparent display, surface display by wire frame may also be used.

FIG. 38 shows a display function in which lamino images 511 at positions specified on the three-dimansional image 51 by an arrow is displayed. When the arrow is moved by operator through pointing device 6121, the original lamino image is successively called up and displayed according to the position of the arrow. The three-dimensional image 51 can be enlarged in the depthward direction and the points can be finely specified. The depthward range of the image used at this time may be selected and specified freely.

Figure 39:
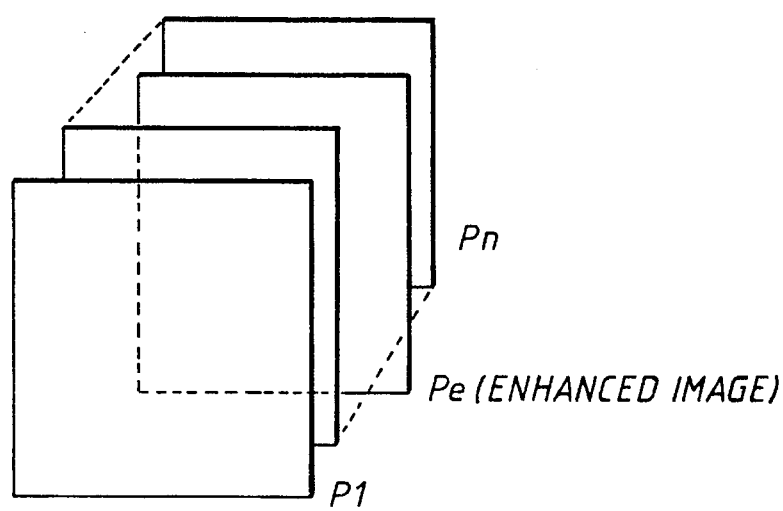
FIG. 39 is a view showing a display with a specified section enhanced in the three-dimensional display in the laminograph shown in FIG. 32.

FIG. 39 shows a case in which a specified section of a three-dimensional image 51 is enhanced and displayed. An image Pe specified by the cursor is displayed at normal gradation, the other image gradations are compressed, and they are shown in three dimensions. There are many methods of enhancement of three-dimensional image including said filtering of spatial shape etc. Also only the specified image alone may be displayed in colour.

In the embodiments described above, it is possible to obtain lamino images with excellent S/N ratio. It is also possible, as shown in FIG. 33, to improve images in an area with specific density characteristics. Also, as shown in FIGS. 34 and 35, it is possible to improve the S/N ratios of the focal plane is terms of shape and spatial frequency. A solid image display can be performed by three-dimensional image display. A specified lamino image in the three-dimensional image can be enhanced and viewed, and it is possible to inspect an interesting part while retaining an appreciation of the entire subject. It is possible to improve inspection efficiency by examining added or composed images.

FIG. 40 shows the display of fixed pitch averaged images in a fourteenth embodiment of the invention. In this figure, original lamino images (FIG. 40(*a*)) are averaged at every fixed pitch interval making averaged images shown in FIG. 40(*b*), and this is displayed in three dimensions, as shown in FIG. 40(*c*). Effectiveness can be improved, mistakes of overlooking can be avoided, by examining this compressed image of large number of lamino images.

FIG. 41 is an explanatory figure showing the detection and deletion of specific images according to a fifteenth embodiment of this invention. In this figure, when radiographic images are taken while the subject is scanned in one direction and when there is a linear pattern along the scan direction in radiographic image, it could not be shadded off by lamino processing even if it originates from off focal pattern in subject. Accordingly, if linear pattern along the direction of scanning is detected as the specified point of the radiographic image, the effect of this pattern may be minimized or removed beforehand, or a warning or an instruction to change the azimuth of subject may be issued.

Figure 42:
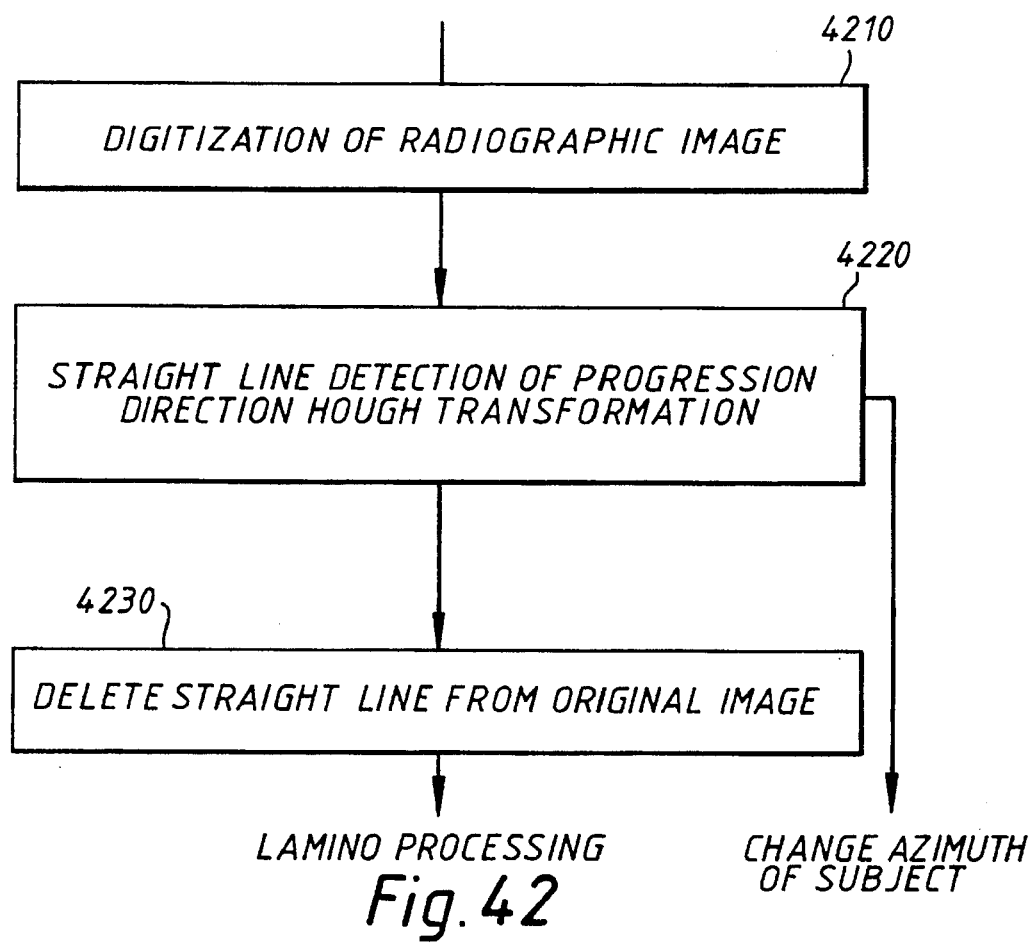
FIG. 42 is a flow chart showing the processes of extraction and deletion of specific images shown in FIG. 41.

FIG. 42 is a flow chart showing the processes of detecting and deleting the specific images shown in FIG. 41. FIG. 42 shows a case in which the azimuth of subject is changed and a case in which the specific images are deleted. That is, in FIG. 42, a radiographic image is digitized (step 4210), and a Hough transformation is used to detect the line in the scann direction (step 4220).This transformation is performed by specific point detection part 617 shown in FIG. 32. After Hough transformation, the changing of the azimuth of subject is performed, or straight lines are deleted from the original image (step 4230), and then lamino processing is performed. The above-described detection is also possible by looking at the linkages of pixels in this direction without Hough transformation. It is thus possible to prevent display of incorrect information on the lamino image.

Below another embodiment of this invention is described with reference to figures.

Figure 43:
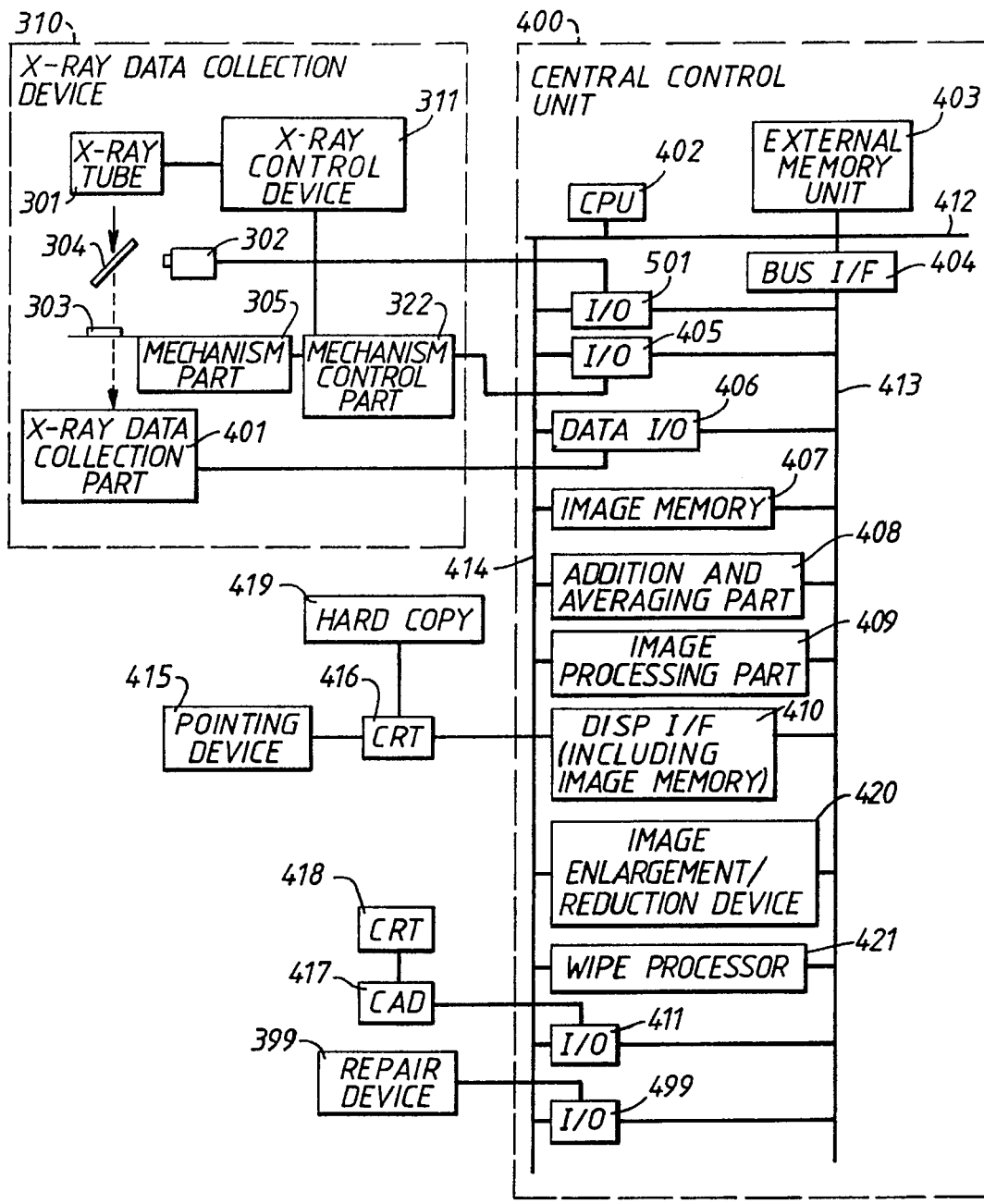
FIG. 43 is a block diagram showing the structure of another embodiment of a laminograph according to this invention.

FIG. 43 is a block diagram showing the structure of one embodiment of a laminograph according to this invention. The laminograph shown in this Figure comprises an X-ray data collection device 310 and a central control unit 400. X-ray data collection device 410 has an X-ray tube 301, an X-ray data collection part 401, which includes X-ray detection sensors, a mechanism part 305 which moves a subject 403, an X-ray control part 311 which controls X-ray tube 301, a mechanism control part 322 which controls mechanism part 305, a half-mirror 304 fitted in the X-ray route between X-ray tube 301 and X-ray data collection part 401, and a television camera 302 which photographs the images of the subject reflected in half-mirror 304.

Central control unit 400 has a CPU 402 which controls all operations, an external memory unit 403 which stores various data, a bus interface 404 connected to CPU 402 via a system bus 412. Between an image bus 414 connected to system bus 412 and an I/O bus 413 connected to bus interface 404, I/Os 501 and 405, a data I/O 406, an image memory 407, an addition and averaging part 408, an image processing part 409, a display interface 410 including an image memory, an image enlargement/reduction device 420, a wipe processing part 421, and I/Os 411 and 499. Also, a CRT display 416 is connected to display interface 410. A hard copy 419 and a pointing device 415 are also connected to CRT display 416. A CAD 417 is connected to I/O 411 and a CRT display 418 is connected to CAD 417. Also, a repair device 399 is connected to I/O 499. Also, I/O 501 is connected to television camera 302, I/O 405 is connected to mechanism control device 322 and data I/O 406 is connected to X-ray data collection part 401.

Central control unit 400 accepts X-ray data from X-ray data collection device 310, and acts as a laminograph to execute image processing, such as to prepare complex images etc, using image memory 407, adding and averaging part 408, image processing part 409 and CPU 402.

FIG. 44 shows the structure of repair device 399 used in the laminograph shown in FIG. 43. Repair device 399, which repairs soldered parts, is composed of a PWB locating device 384, a repair information display and input device 382, a laser marker 383 and a control device 381, and is connected to central control unit 400 via control device 381 and I/O 499.

In the laminograph of this structure, while subject 303 is moved by mechanism part 305 it is penetrated by X-rays irradiated from X-ray tube 301, and during this movement radiographic images from various direction are obtained by taking these X-rays as radiographic images by X-ray data collection part 401. Mechanism part 305 has a controllable mechanism capable of moving the desired position on the surface including planes of the PWB which is the subject, so that it is possible to obtain transmission data for the position specified by CAD 417. This control is performed by mechanism control device 322.

The transmission data is taken in by image memory 407 of central control unit 400 via data I/O 406. Radiographic images, given a shift amount according to the focal plane, are prepared by addition and averaging part 408 which performs image addition and obtains a tomographic image of the desired focal plane. In this method of data collection the image obtained is a plane parallel to the direction of movement of subject 303.

Data on the PWB board, which is subject 303, and the parts mounted on the PWB board are sent to image memory 407 beforehand from CAD 417, and the size is changed by the image processing part 409 to match the size of the radiographic image determined by X-ray geometry.

The lamino image thus obtained is added with fitting the CAD pattern events to prepare a composed image. This image can be displayed on CRT 416 via display interface 410. The same image is sent to repair device 399 and can be viewed by the repair line.

Figure 45A:
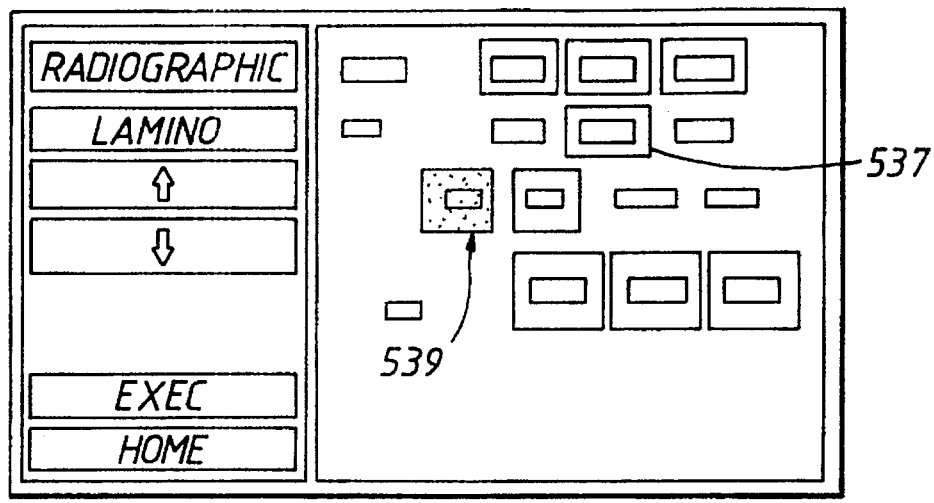
FIGS. 45a–45c are views showing the form of the image displayed on the display.
Figure 45B:
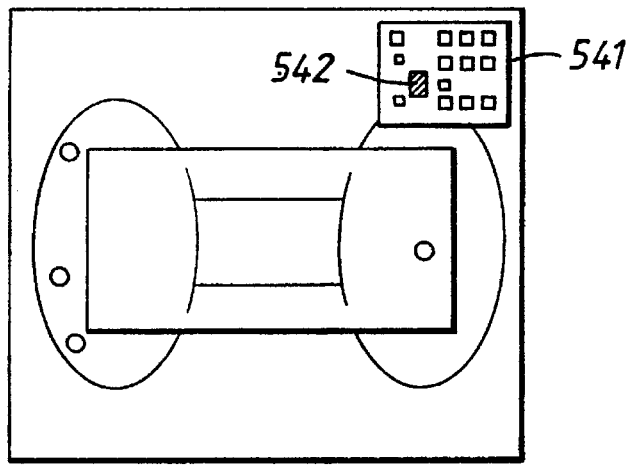
Figure 45C:
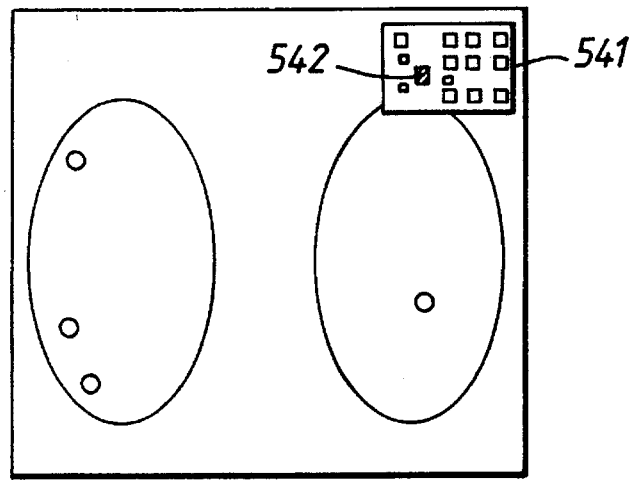

FIG. 45 shows the form of images displayed on the display. FIG. 45(a) shows a display composed from CAD patterns and a local lamino image, FIG. 45(b) shows the radiographic image and FIG. 45(c) shows the lamino image. It is possible to display the desired image by specifying an icon on the CRT display with cursor 539. It is possible to show which position of the whole subject has been specified by displaying in a part of the image as a wipe image 541. The specified position 542 is characterized by changing colour.

Figure 46A:
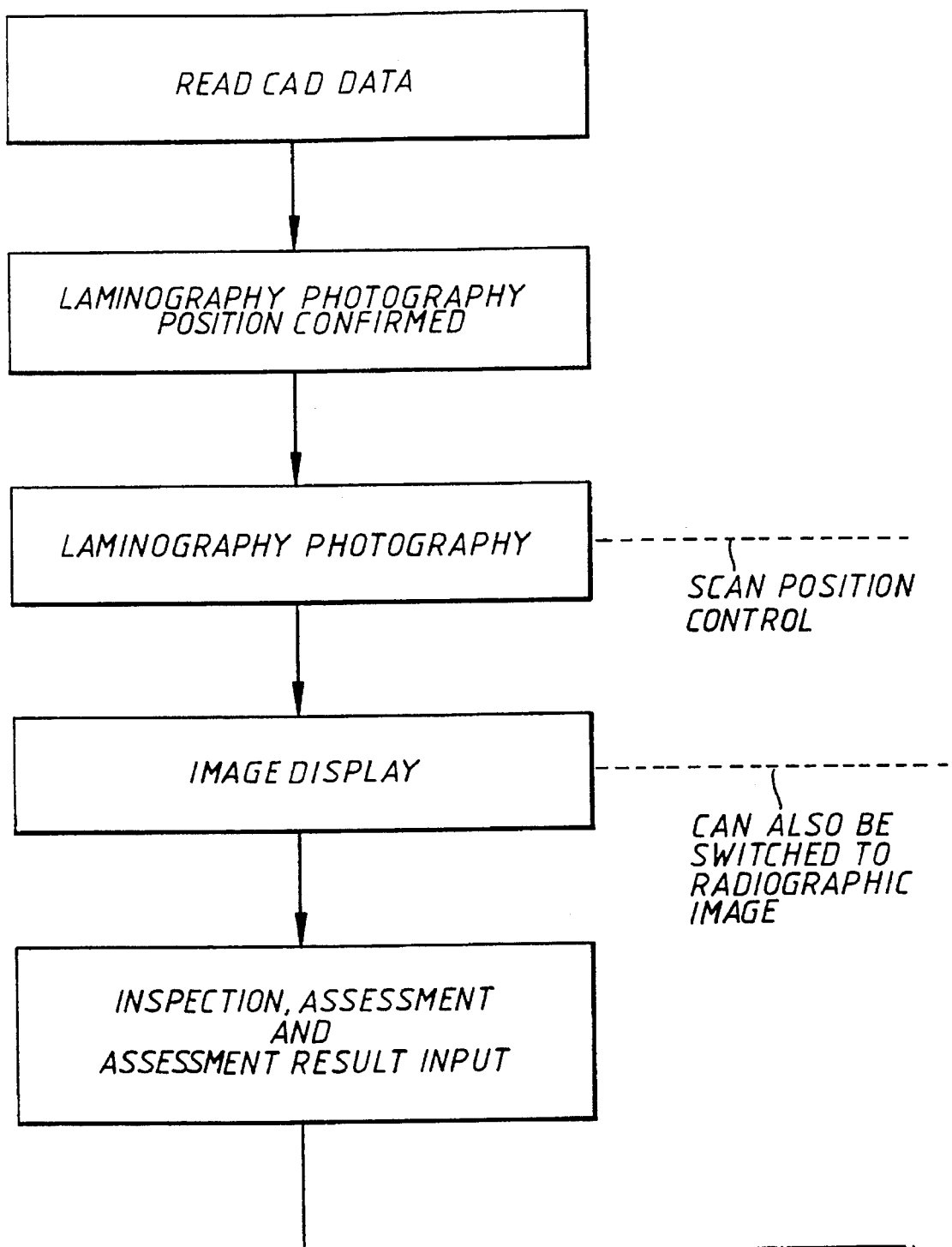
FIG. 46 is a flow chart showing the operations of the laminograph shown in FIG. 43.
Figure 46B:
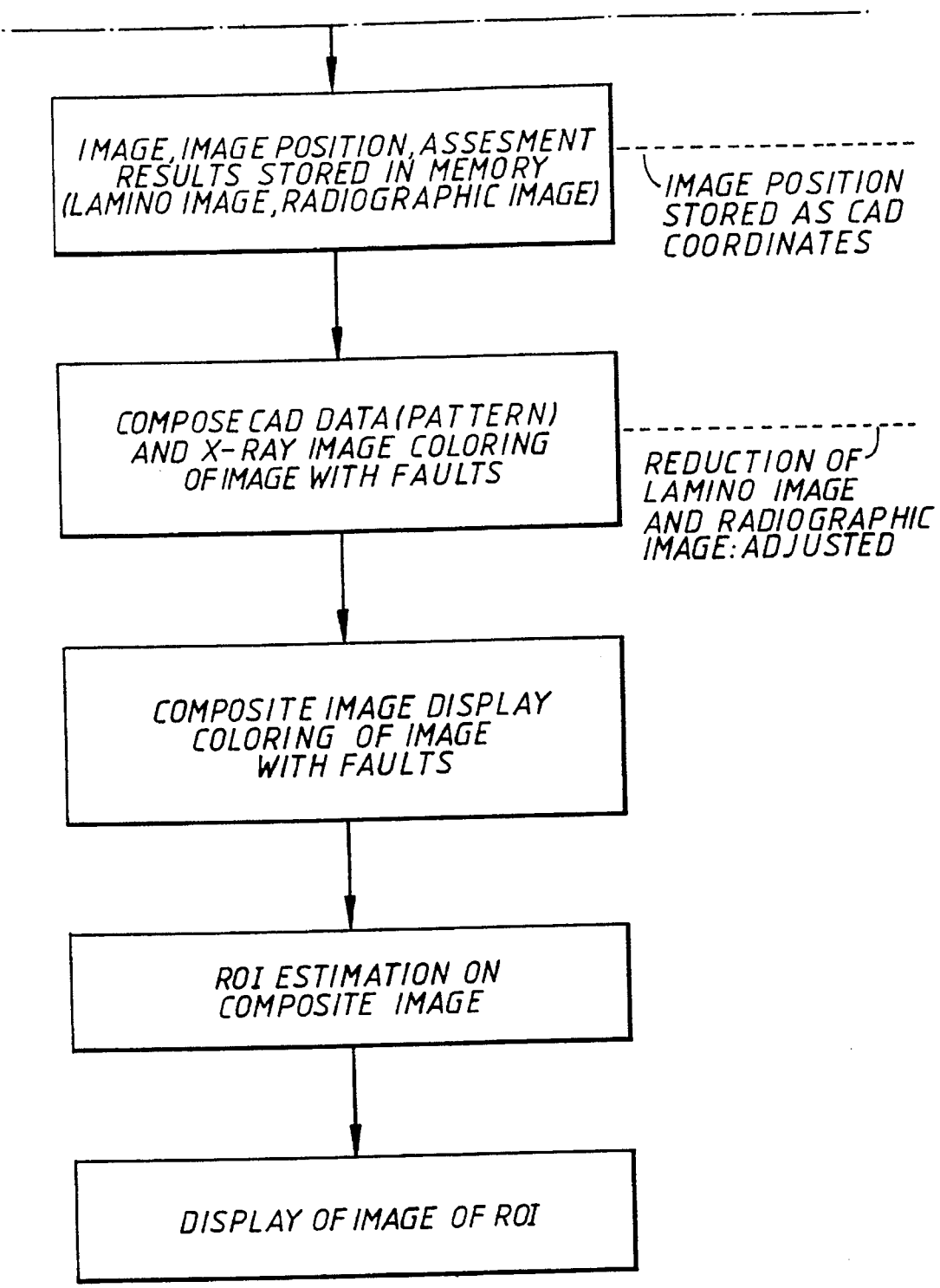

The flow of operation is shown in the flow chart shown in FIG. 46. In FIG. 46, ROI is the region of interest.

Figures 47A, 47B:
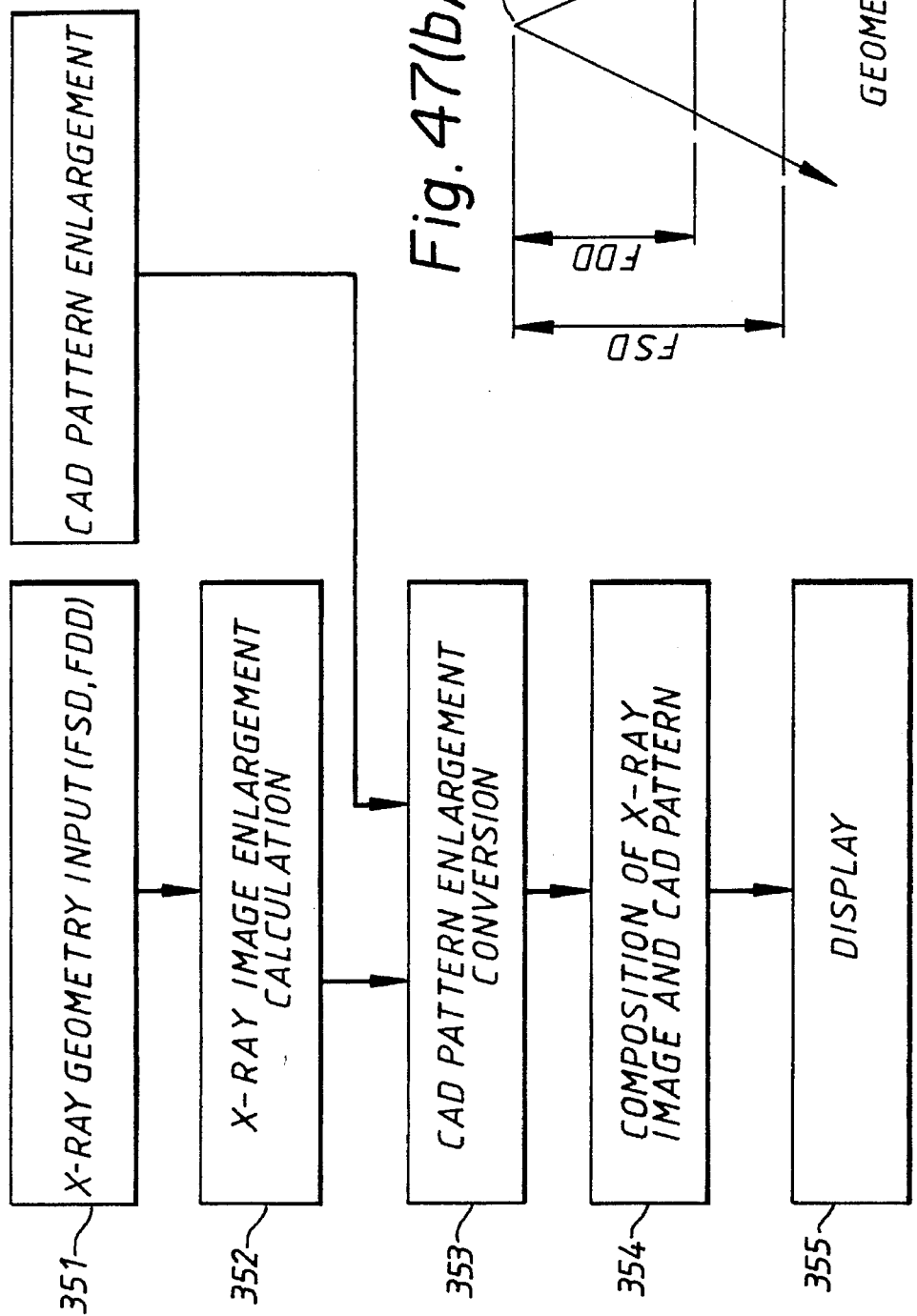
FIG. 47a and 47b are a flow chart showing the method of matching the reduced scale of CAD pattern and the radiographic image.

FIG. 47(a) is a flow chart showing the method of matching the reduced scales of the radiographic image and the CAD pattern. In this figure, first the X-ray geometry is input (step 351) and X-ray image magnification is calculated (step 352). Methods of finding X-ray image magnification include a method in which it is found from X-ray focal point, object position and sensor position (FSD, FDD), a method in which it is found from the radiographic image of an object of previously known dimensions on the PWB, and a method in which the position of the object from the X-ray focal spot is measured by X-rays or optically. FIG. 47(b) shows the X-ray geometry.

After the X-ray image magnification is calculated, the CAD pattern magnification is changed (step 353). In this case, the X-ray magnification may be changed instead. Next, the X-ray image and CAD picture are composed (step 354) and displayed (step 355).

Figure 48:
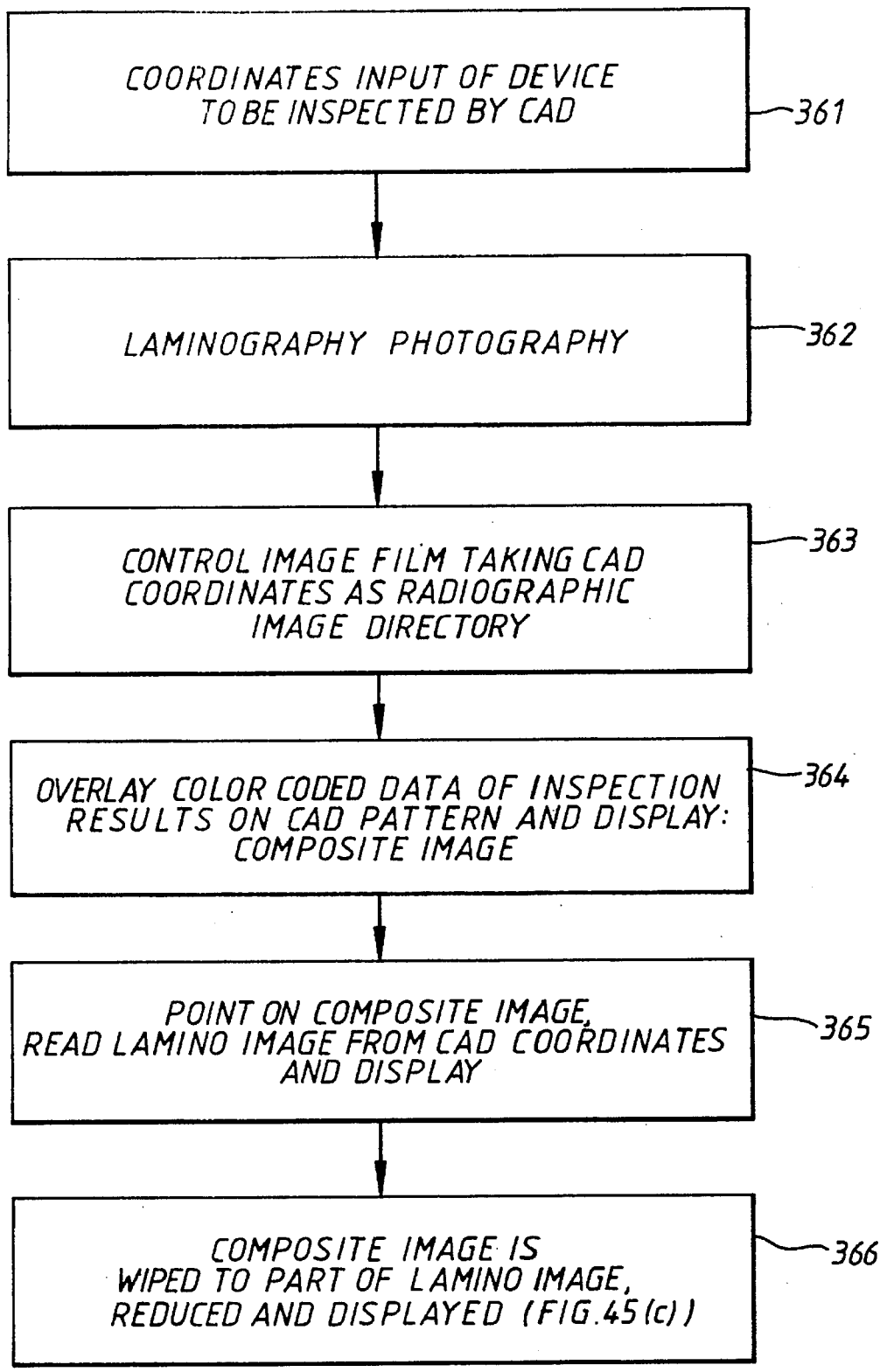
FIG. 48 is a flow chart showing the image display sequence.

FIG. 48 is a flow chart showing the image display sequence. The CAD data includes coordinate data of the mounted parts to be inspected. In FIG. 48, the position on the PWB where it is necessary for a laminograph to be obtained is identified from this information of the CAD data, and a lamino image is then obtained (steps 361 and 362). The coordinates in the CAD data of the lamino image are image managed as a directory (step 363). The radiographic images may be managed similarly. Images displayed on the CRT for visual assessment or the results of automatic assessment of the images, may be made into a composite image which is colour coded according to the type of fault (step 364). When radiographic image is called up, when a position on the composite image is pointed to, as the graphic coordinates has been made as the directory it can be read from the file (step 365). The composite image is wiped to a part of the lamino image and is displayed in reduced form as shown in FIG. 45(*c*) (step 366).

Fault assessment can be performed automatically by image processing the radiographic image and lamino image obtained. Generally, transmission of X-ray through solder faults is greater than through sound parts and it is possible to use this characteristic.

Figure 49:
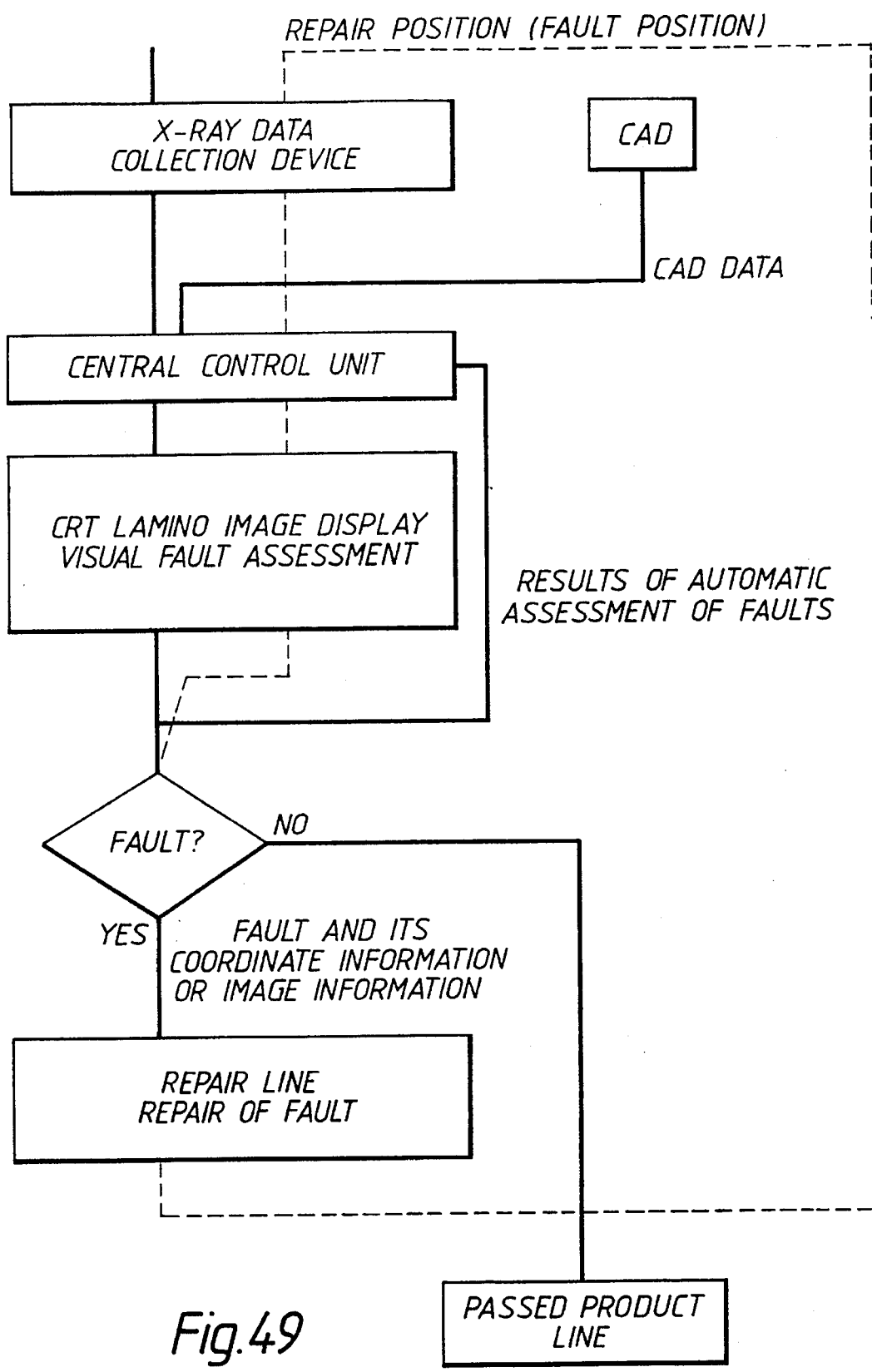
FIG. 49 is a view given in explanation of the correlation with the repair line.
Figure 50:
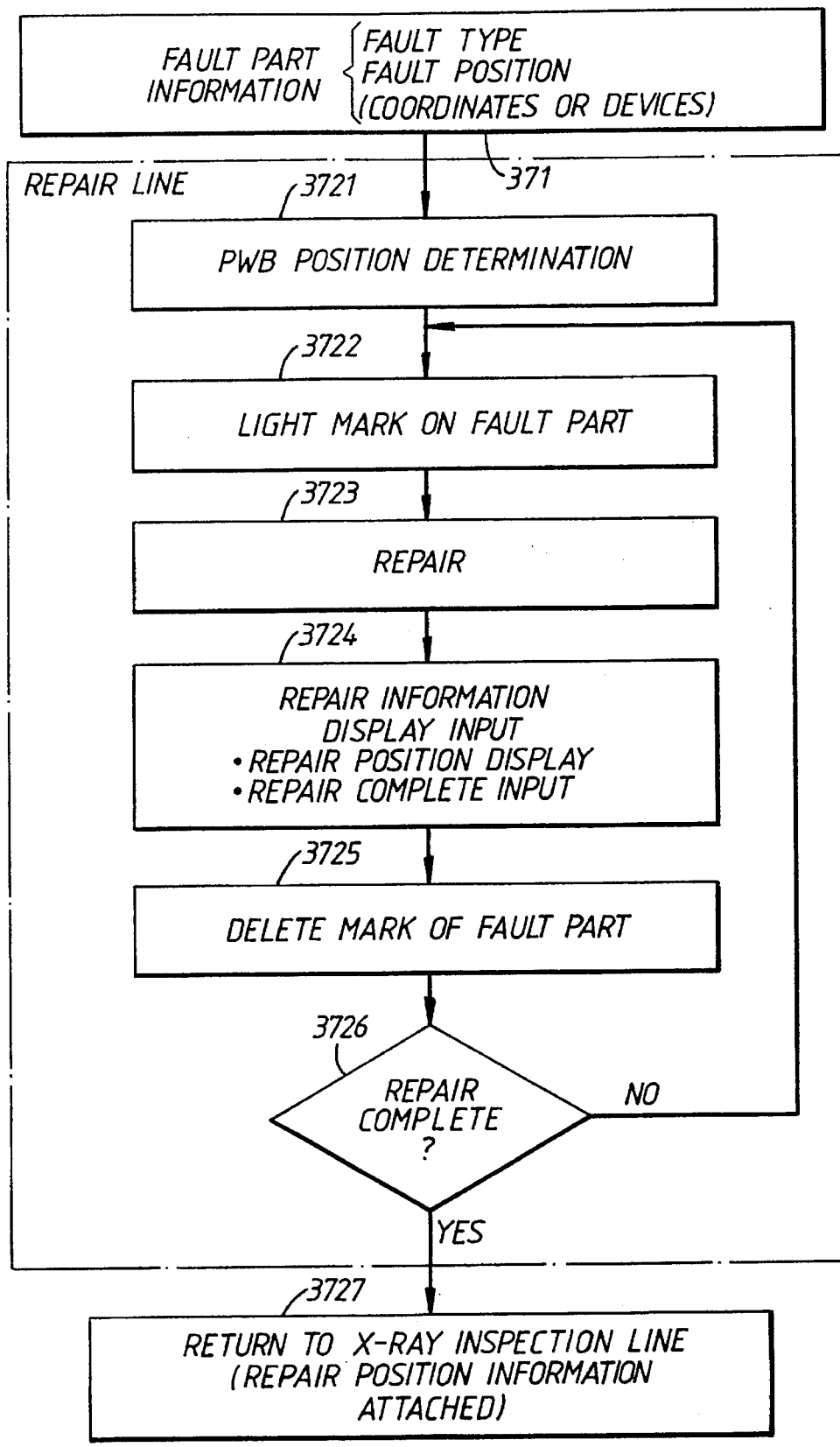
FIG. 50 is a flow chart showing the processes for displaying a fault position.

FIG. 49 describes the correlations with the repair line. A PWB which has been decided to have a fault is sent to the repair line, where it is repaired on the basis of the fault information shown in FIG. 50. In FIG. 50, fault part information 371 which contains information on the types and locations of the faults, is sent from central control unit 400 to control device 381 or the repair line. In the repair line, the PWB is located by locating device 384 of repair device 399 shown in FIG. 44 (steps 3721), and the position of the fault is displayed optically on the PWB (step 3722). Colour coding can also be carried out according to the type of fault. FIG. 44 shows a case in which laser marker 383 is used, that is laser light from a laser gun, diverted by a mirror, is used for indication.

The composite image can be displayed on the CRT. It is possible to identify the repair position without the use of a fault marker. As in the case of the inspection line, the radiographic image can be displayed according to position specification. When the repair is finished, input is made for the finished position from the CRT (panel switch) (step 3724). Of course a combination of CRT and pointing device 415 can be used for input instead of the panel switch. When a marker is used, the indication of the point at which the repair is finished is cancelled at this time (step 3725). The coordinates of the position at which the repair has been finished are handled in the same way as the CAD coordinate data of the mounted part to be inspected, via control device 381 and are used as the coordinates for re-inspection of the PWB returned from the repair line.

At the repair line, automatic repairs of the fault can be carried out by a laser heating device or an electric soldering iron, according to the type of solder void or solder deficit. At this time, repair device 399 is controlled on the basis of the type of fault and position coordinates.

Figure 51:
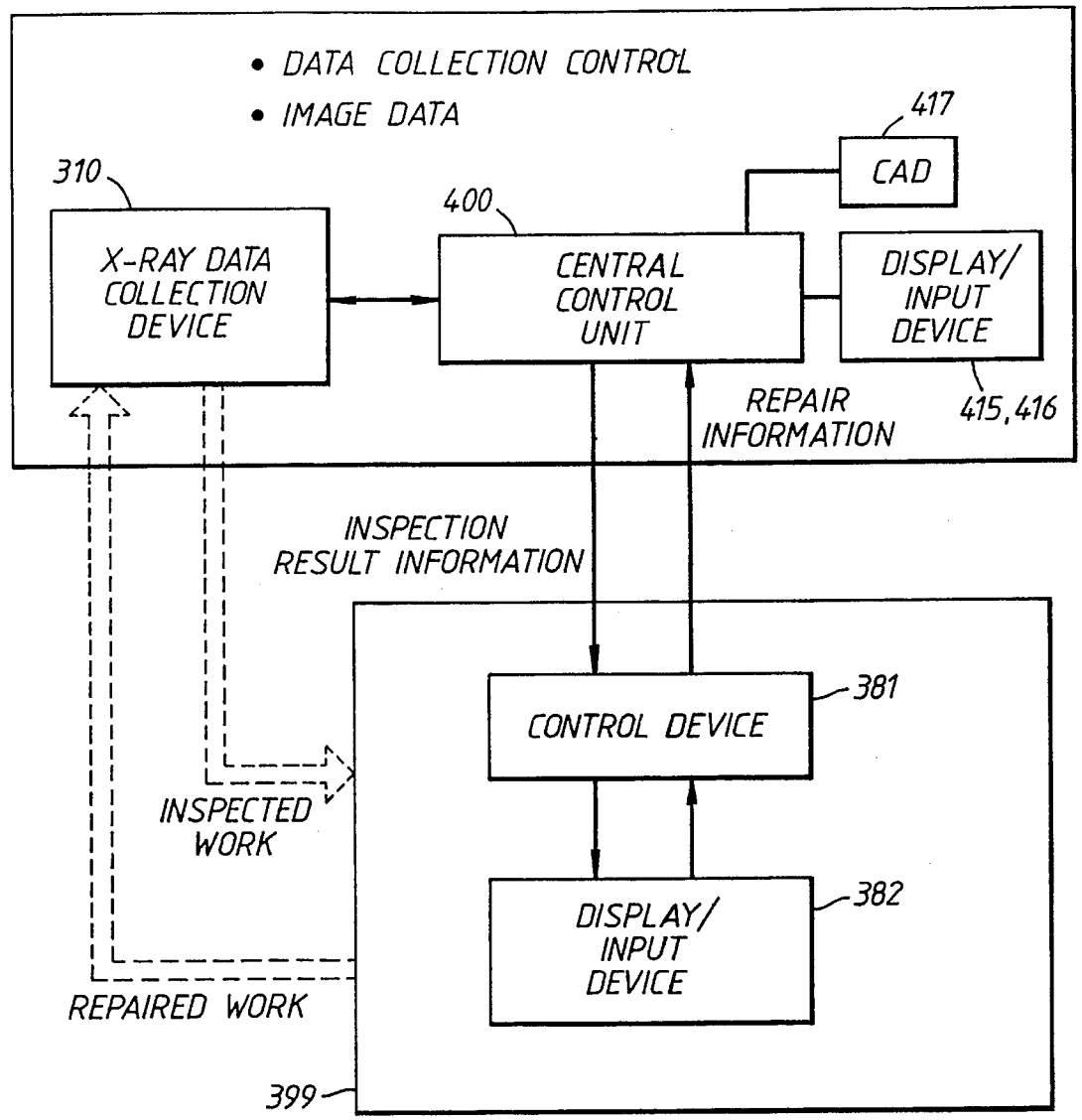
FIG. 51 is a flow chart showing the flow of the X-ray inspection and repair processes.
Figure 53:
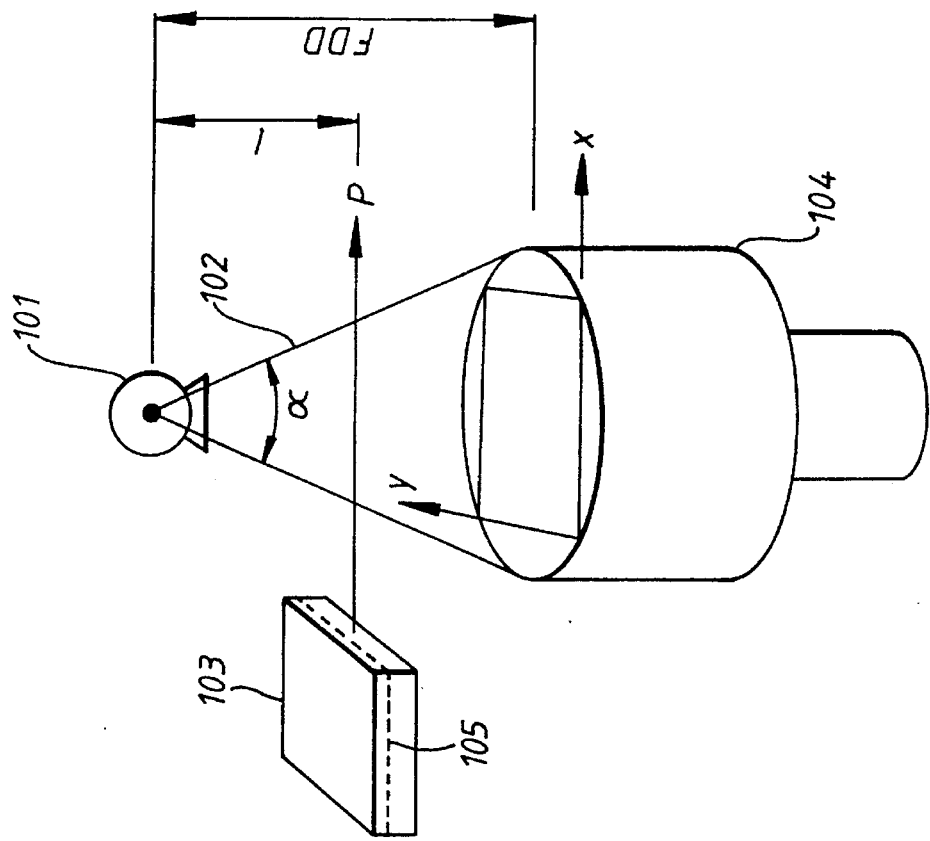
FIG. 53 is a view showing another laminograph of the prior art.
Figure 52:
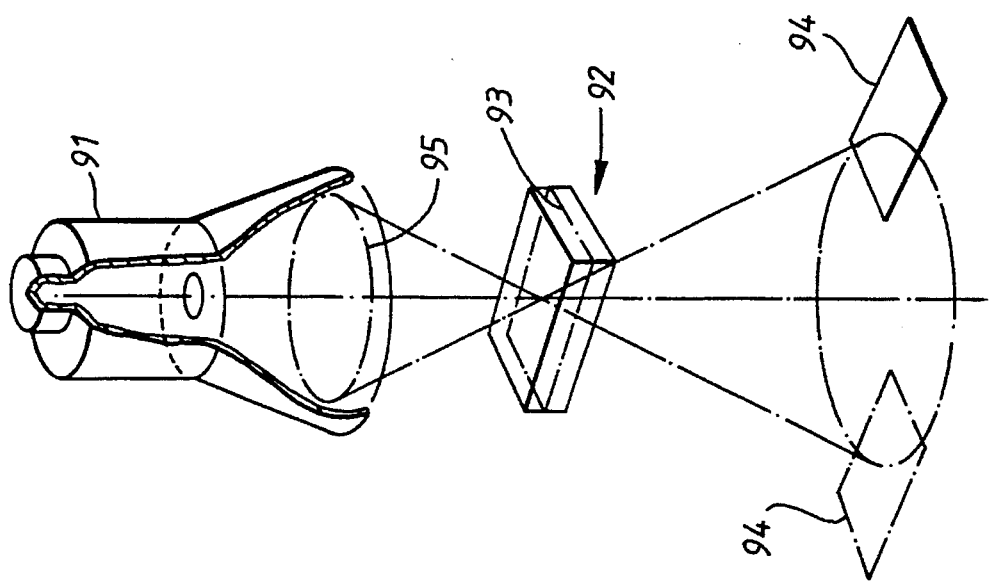
FIG. 52 is a view showing a laminograph of the prior art.
Figure 54A:
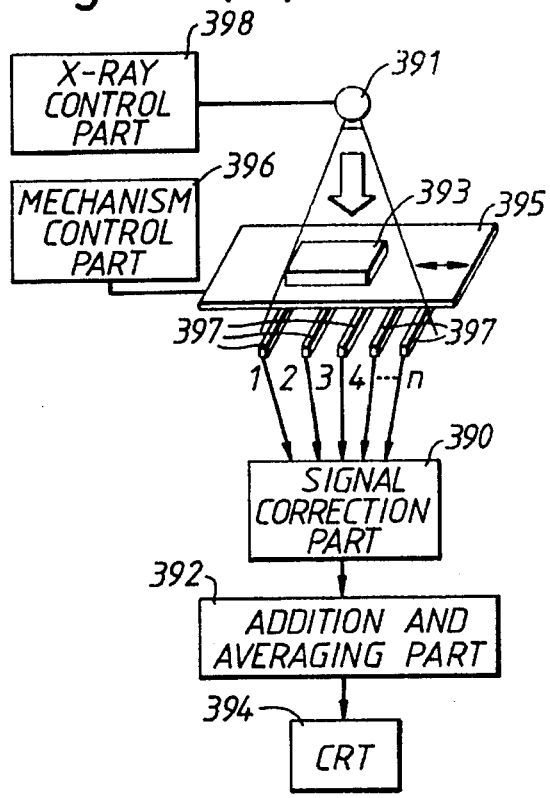
FIGS. 54a–54c are views showing the structure and functions of still another laminograph of the prior art.
Figure 54B:
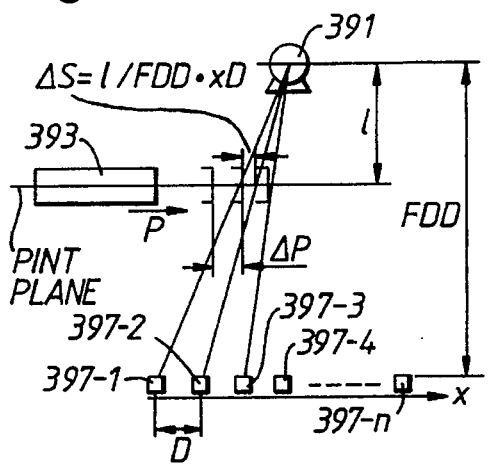
Figure 54C:
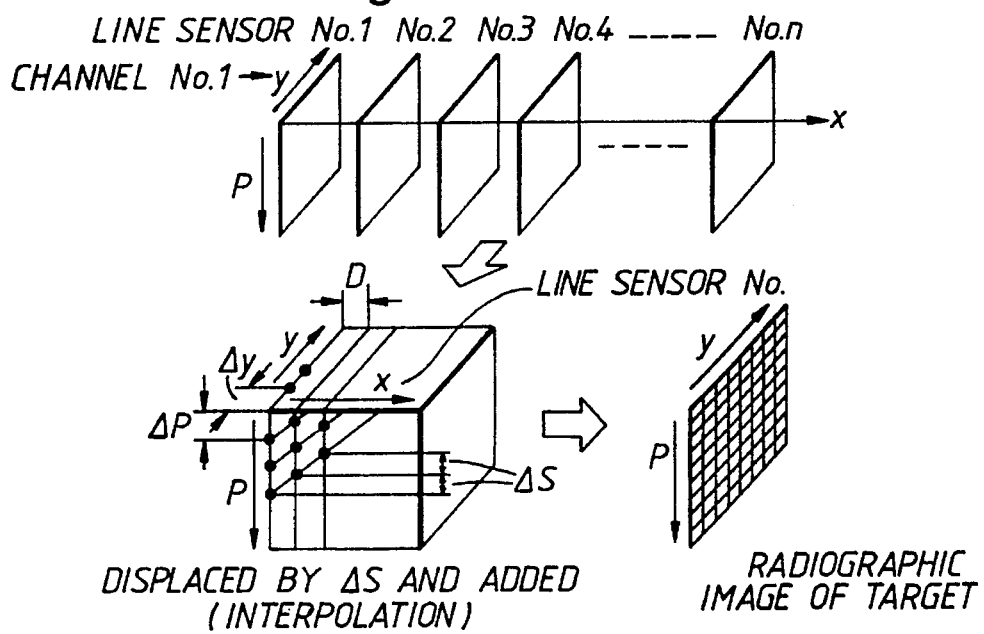

When the repairs to the PWB at the repair line are completed, the PWB is returned to the X-ray inspection line (steps 3726 and 3727) and re-inspected. At this time, information of the fault location (the repair location) is sent from control device 381 to central control unit 400, and used as the information identifying the position for re-inspection. Fault information is stored in central control unit 400, and this makes it possible to perform a similar inspection on this information using the control number etc of the board, when a PWB is returned from the repair line after repairs are completed. This loop is repeated until there ape no further faults. FIG. 51 shows the X-ray inspection and repair processes.

When inspection and repairs are automated, the above-described automatic fault assessment is performed by central control unit 400 and control of repair position and repair device 399 is performed by control device 381. Inspection and repair are repeated in a loop, but if the inspection results continue to be poor even when the inspection/repair loop is repeated, the number of loops for the same PWB is managed by the control device, an "irreparable" result is output and the PWB is sent to reserved stock.

These inspection information and repair information are stored in external memory unit 403 of central control unit 400 and they can be read out and be considered at any time. It is also possible to output records of images and/or information. The external memory unit may be attached to the control device of the repair line.

Also, as shown in FIG. 43, television camera 302 is fitted to the X-ray data collection device 310 so as to photograph the appearance of the PWB via half mirror 304, and it is possible to compose this appearance image with an X-ray image or CAD information.

The following effects are achieved by the embodiment described above.

(1) Transmission inspection of the PWB and obtaining a laminograph of the PWB are performed using CAD data, and so the inspection position can be identified more rapidly and efficiently.

(2) Inspection information of the whole PWB can be found on a composite image of CAD pattern and radiographic images. It is also possible to store this information.

(3) It is possible to specify and display necessary radiographic images from the composite image. It is also possible to identify which image is being displayed by wiping and inserting the composite image to a part of the radiographic image. The coordinates of the radiographic image can be displayed at the same time. The CAD coordinates can be used as an image directory.

(4) It is possible to have a display which identifies the type of fault.

(5) The fault position and fault type of the PWB can be displayed on the PWB at the repair line.

(6) The position and nature of the repair can be confirmed at the repair line from image information on the CRT, and operation can be carried out along with the confirmation. It has also an input means which manages the ending of repairs.

(7) After repairs, the PWB is returned to the inspection line, and only the repaired part of the PWB can be re-inspected.

(8) The position of the soldering device is controlled on the basis of the information of the inspection results, and solder repairs can thus be performed automatically.

(9) The composite image can be wiped on the radiographic image for display. It is possible to display the radiographic image by distinguishing the location of the radiographic image currently displayed in the composite image.

Also, as shown by 537 in FIG. 45(*a*), it is possible to distinguish the fact that a PWB has passed after repair, on the area where a repaired PWB has been re-inspected and the fault had been removed and to display this on the composite image. The automatic inspection results or visual assessment results are input by pointing device 415. It is thus possible to confirm the repair results and improve the reliability of the repair line.

Also, an automatic inspection and repair device can be designed to automatically perform an X-ray inspection/repair X-ray inspection . . . loop. This is achieved by forming the loop shown as broken line in FIG. 49 and thus automating the fault assessment of radiographic images and solder repairs.

As described above, according to this invention, the position of the focal plane in the subject is measured and the displacement distance is calculated on the basis of the position of the focal plane thus measured, and so it is possible to obtain with precision and certainty a tomographic image of the desired plane.

According to this invention, as the displacement distance is determined by a pattern on the radiographic image, it is possible to focus on the desired plane solely by processing the radiographic image obtained by irradiating the subject, and it is thus possible to obtain with precision and certainty a tomographic image of the desired plane.

Also, according to this invention, as laminography processes of the radiographic image are performed after enhancing, weakening or deleting characteristics of the radiographic image, it is possible to improve the S/N ratio of the lamino image, to obtain lamino images with the desired image information enhanced, and to examine lamino image groups as a small number of added images.

As described above, according to this invention, it is possible to efficiently control the inspection position of a subject with a large inspection area and to inspect this. It is also possible to supply the inspection results to a repair line and to indicate the repair position the subject. Specification of the repaired part to be re-inspected and assessment of repair results can be managed on images composed from radiographic images and CAD patterns.

Obviously, numerous modifications and variations of the present invention are possible in light of the above teachings. It is therefore to be understood that within the scope of the appended claims, the invention may be practiced otherwise than as specifically described herein.

What is claimed is:

1. A laminograph, comprising:

an X-ray radiation source for generating radiation towards a subject;

radiation surface sensor means, with a two-dimensional resolution, fitted opposite to said X-ray radiation source for detecting said radiation from said X-ray radiation source which has passed through said subject;

scanning means for moving said subject to take a plurality of different positions between said X-ray radiation source and said radiation surface sensor means and for scanning said subject in each of said different positions by said radiation from said X-ray radiation source;

data collection means for collection a plurality of outputs of said radiation surface sensor means during said scanning by said scanning means to obtain a plurality of radiographic images of said subject in said different positions;

position measurement means for measuring multiple positions of a focal plane at multiple places of said subject;

displacement measurement means for measuring multiple displacements based on said multiple positions of said focal plane measured by said position measurement means; and image processing means for displacing said plurality of radiographic images in relation to the multiple displacements measured by said displacement measuring means and for adding and averaging said plurality of displaced radiographic images to obtain a radiographic image of said subject focused on said focal plane as a tomographic image of said subject.

2. The laminograph according to claim 1, wherein:

said radiation surface sensor means is provided with a horizontal plane xy as a measurement surface; and said scanning means includes movement means for moving said subject in a direction x between said X-ray radiation source and said radiation surface sensor means.

3. The laminograph according to claim 1, wherein, said scanning means includes:

means for rotating said X-ray radiation source around a single axis of rotation which is approximately normal to a measurement plane of said radiation surface sensor means; and means for orbiting said radiation surface sensor means, in synchronism with a rotation of said X-ray radiation source, around said axis of rotation keeping an azimuth of said radiation surface sensor means constant.

4. A laminograph, comprising:

an X-ray radiation source for generating radiation towards a subject;

movement means for moving said subject along directions x and y which intersect each other;

radiation surface sensor means, with a measurement plane parallel to an xy plane formed by said directions x and y, fitted opposite to said X-ray radiation source for detecting said radiation from said X-ray radiation source which has passed through said subject;

scanning means for moving said subject in said x direction to take a plurality of different positions between said X-ray radiation source and said radiation surface sensor means and for scanning said subject in each of said different positions by said radiation from said X-ray radiation source;

data collection means for collecting a plurality of outputs of said radiation surface sensor means during said scanning by said scanning means to obtain a plurality of radiographic images of said subject in said different positions;

position measurement means for measuring multiple positions in a direction at a right angle to said xy plane at multiple places of a surface of said subject;

displacement measurement means for calculating multiple displacement based on said multiple positions measured by said position measurement means, so that a focal plane is formed on said surface of said subject; and image processing means for displacing said plurality of radiographic images in relation to the multiple displacements measured by said displacement measuring means and for adding and averaging said plurality of displaced radiographic images to obtain a radiographic image of said subject focused on a single plane parallel to said xy plane of said subject as a tomographic image of said subject.

5. The laminograph according to claim 4, wherein:

said subject is a laminar body fitted so that its longitudinal direction is approximately parallel to said xy plane;

said position measurement means measures said multiple positions in a direction z at a right angle to said xy plane at said multiple places of said surface of said subject; and said image processing means obtains said radiographic image of said subject focused on one of said surface of said subject and said single plane parallel to said xy plane to said subject separated by a predetermined distance from said surface.

6. The laminograph according to claim 5, wherein:

said position measurement means measures said multiple positions on said surface of said subject for respective one of multiple radiographic image preparation regions of said laminar body; and said image processing means obtains said radiographic image based on said multiple positions measured for said multiple radiographic image preparation regions.

7. The laminograph according to claim 5, wherein:

said position measurement means measures a plurality of surface measurement positions scattered on said surface of said laminar body, in direction z; and said image processing means calculates said multiple positions in direction z by interpolating said surface measurement positions for said multiple radiographic image preparation regions, respectively, and obtains said radiographic image based on said multiple positions calculated for said multiple radiographic image preparation regions.

8. A laminograph, comprising:

an X-ray radiation source for generating radiation towards a subject;

radiation surface sensor means, with a two-dimensional resolution, fitted opposite to said X-ray radiation source for detecting said radiation from said X-ray radiation source which has passed through said subject;

scanning means for moving said subject to take a plurality of different positions between said X-ray radiation source and said radiation surface sensor means and for scanning said subject in each of said different positions by said radiation from said X-ray radiation source;

data collection means for collecting a plurality of outputs of said radiation surface sensor means during said scanning by said scanning means to obtain a plurality of radiographic images of said subject in said different positions;

position measurement means for measuring multiple positions of a focal plane at multiple places of said subject;

focusing means for moving one of said subject and a combination of said X-ray radiation source and said radiation surface sensor means so that positions to be focused coincide with a focal plane formed by said combination of said X-ray radiation source and said radiation surface sensor means based on said multiple positions on said surface of said subject measured by said position measurement means; and image processing means for adding and averaging said plurality of radiographic images to obtain a radiographic image of said subject focused on said focal plane as a tomographic image of said subject.

9. The laminograph according to claim 8, wherein:

said radiation surface sensor means is provided with a horizontal plane xy as a measurement surface; and said scanning means includes movement means for moving said subject in a direction x between said X-ray radiation source and said radiation surface sensor means.

10. The laminograph according to claim 8, wherein said scanning means includes:

means for rotating said X-ray radiation source around a single axis of rotation which is approximately normal to a measurement plane of said radiation surface sensor means; and means for orbiting said radiation surface sensor means, in synchronism with a rotation of said radiation source, around said axis of rotation keeping an azimuth of said radiation surface sensor means constant.

11. A laminograph, comprising:

an X-ray radiation source for generating radiation towards a subject;

radiation surface sensor means, with a two-dimensional resolution, fitted opposite to said X-ray radiation source for detecting said radiation from said X-ray radiation source which has passed through said subject;

scanning means for rotating said radiation source around a single rotatory axis in an axial direction z, for orbiting said radiation surface sensor means around said rotatory axis with an 180° phase differences therefrom and synchronized with the rotation of said X-ray radiation source, while maintaining the direction plane of said radiation surface sensor means at right angles to said rotatory axis, and for scanning said subject in a plurality of different positions by said radiation from said X-ray radiation source;

subject locating means for setting said subject on said rotatory axis between said radiation surface sensor means and said X-ray radiation source;

data collection means for collecting a plurality of outputs of said radiation surface sensor means during said scanning by said scanning means to obtain a plurality of radiographic images of said subject in said different positions;

position measurement means for measuring multiple positions in axial direction z on said surface of said subject;

focusing means for moving said subject so that positions to be focused coincide with a focal plane formed by said X-ray radiation source and said radiation surface sensor means based on said multiple positions on said surface of said subject measured by said position measurements means; and image processing means for adding and averaging said plurality of radiographic images to obtain a radiographic image of said subject focused on a single plane parallel to said detection plane of said subject as a tomographic image of said subject.

12. The laminograph according to claim 11, wherein:

said subject locating means includes an xy table for moving said subject along directions x and y which intersect each other and also said rotatory axis and for setting said subject such that a detection area for said radiographic image to be taken is located on said rotatory axis.

13. The laminograph according to claim 12, wherein:

said focusing means includes a z table for moving said subject in direction z.

14. The laminograph according to claim 11, further comprising:

means for shifting said X-ray radiation source along a line joining said X-ray radiation source and said radiation surface sensor means and for changing a magnification of said radiographic image based on said shift.

15. The laminograph according to claim 11, further comprising:

rotating means for rotating said X-ray radiation source around a rotating axis passing through a radiation part of said X-ray radiation source.

16. A laminograph, comprising:

an X-ray radiation source for generating radiation towards a subject;

radiation surface sensor means, with a two-dimensional resolution, fitted opposite to said X-ray radiation source for detecting said radiation from said X-ray radiation source which has passed through said subject;

scanning means for moving said subject to take a plurality of different positions between said X-ray radiation source and said radiation surface sensor means and for scanning said subject in each of said different positions by said radiation from said X-ray radiation source;

data collection means for collecting a plurality of outputs of said radiation surface sensor means during said scanning by said scanning means to obtain a plurality of radiographic images of said subject in said different positions;

displacement determining means for determining multiple displacements at multiple places of said subject based on a pattern on said radiographic images; and image processing means for displacing said plurality of radiographic images in relation to the multiple displacements measured by said displacement measuring means and for adding and averaging said plurality of displaced radiographic images to obtain a radiographic image of said subject focused on a single focal plane as a tomographic image of said subject.

17. The laminograph according to claim 16, wherein:

said displacement determining means includes means for determining said multiple displacements by finding correlation between said patterns in different radiographic images.

18. The laminograph according to claim 16, wherein:

said displacement determining means includes means for determining said multiple displacements by finding differences between a specific pattern and a pattern in said radiographic image.

19. The laminograph according to claim 16, wherein:

said subject includes a mounted board;

said pattern is a solder pattern formed by solder on said mounting board;

said displacement determining means determines said multiple displacements by extracting as said pattern by digitization of said solder pattern on said radiographic images, and by finding correlation between said solder patterns in different radiographic images; and said image processing means adds and averages said plurality of radiographic images with said displacements to obtain said radiographic image of said subject focused on said solder part as a tomographic image of said subject.

20. The laminograph according to claim 17, wherein:

said displacement determining means includes means for taking correlation for edge emphasized pattern obtained by differentially processing said radiographic images.

21. A laminograph, comprising:

an X-ray radiation source for generating radiation towards a subject;

radiation surface sensor means, with a two-dimensional resolution, fitted opposite to said X-ray radiation source for detecting said radiation from said radiation X-ray source which has passed through said subject;

scanning means for moving said subject to take a plurality of different positions between said X-ray radiation source and said radiation surface sensor means and for scanning said subject in each of said different positions by said radiation from said X-ray radiation source;

data collection means for collecting a plurality of outputs of said radiation surface sensor means during said scanning by said scanning means to obtain a plurality of radiographic images of said subject in said different positions;

image pre-processing means for processing one of enhancing, weakening and deleting characteristics of said radiographic images to obtain pre-processed radiographic images; and laminograph image restoration means for restoring a tomographic image of a desired plane from said pre-processed radiographic images and from information defining a transmission direction of said radiation.

22. The laminograph according to claim 21, wherein:

said image pre-processing means includes means for performing at least one process out of image density, image shape, spatial frequency of image in a spatial frequency area, logic filtering, inter-image algorithms and morphological processing.

23. A laminograph, comprising:

an X-ray radiation source for generating radiation towards a subject;

radiation surface sensor means, with a two-dimensional resolution, fitted opposite to said X-ray radiation source for detecting said radiation from said radiation source which has passed through said subject;

scanning means for moving said subject to take a plurality of different positions between said X-ray radiation source and said radiation surface sensor means and for scanning said subject in each of said different positions by said radiation from said X-ray radiation source;

data collection means for collecting a plurality of outputs of said radiation surface sensor means during said scanning by said scanning means to obtain a plurality of radiographic images of said subject in said different positions;

laminograph image restoration means for restoring a tomographic image of a desired plane from said radiographic images and from information defining a transmission direction of said radiation; and specific point detection means for detecting images linked in the same direction as the direction for changing said transmission direction to generate a specific point detection signal.

24. The laminograph according to claim 23, further comprising:

image pre-processing means for processing one of enhancing, weakening and deleting characteristics of said radiographic images at said specific point thus detected to obtain pre-processed radiographic images; and wherein said laminograph image restoration means restores said tomographic image of said desired plane from said pre-processed radiographic images and said information for said transmission direction of said radiation.

25. A laminograph, comprising:

an X-ray radiation source for generating radiation towards a subject;

radiation surface sensor means, with a two-dimensional resolution, fitted opposite to said X-ray radiation source for detecting said radiation from said radiation source which has passed through said subject;

scanning means for moving said subject to take a plurality of different positions between said X-ray radiation source and said radiation surface sensor means and for scanning said subject in each of said different positions by said radiation from said X-ray radiation source;

data collection means for collecting a plurality of outputs of said radiation surface sensor means during said scanning by said scanning means to obtain a plurality of radiographic images of said subject in said different positions;

laminograph image restoration means for restoring a tomographic image of a desired plane from said radiographic images and from information defining a transmission direction of said radiation and for said tomographic images thus obtained to produce a composite lamino image.

26. The laminograph according to claim 25, wherein:
said composite lamino image is a type shown in three dimensions.

27. The laminograph according to claim 25, further comprising:
image pre-processing means for processing one of enhancing, weakening and deleteing characteristics of said radiographic images to obtain pre-processed radiographic images; and
wherein said laminograph image restoration means restores said tomographic images of said desired planes from said pre-processed radiographic images and said information for said transmission direction of said radiation, and adds said tomographic images thus obtained to produce said composite lamino image.

28. The laminograph according to claim 27, wherein:
said image pre-processing means includes means for performing at least one process out of image density, image shape, spatial frequency of image in a spatial frequency area, logic filtering, inter-image algorithms and morphological processing.

29. The laminograph according to claim 25, further comprising:
specification means for specifying positions on the depth direction of said composite lamino image, and
image pre-processing means for image enhancement processing to said lamino image at specified position specified by said specification means relative to said lamino images at non-specified position to obtain pre-processed lamino images; and
wherein said laminograph image restoration means obtains said composite lamino image based on said pro-processec lamino images.

30. A laminograph, comprising:
an X-ray radiation source for generating radiation towards a subject;
radiation detection means with a two-dimensional detection area positioned opposite said X-ray radiation source for detecting said radiation from said X-ray radiation source which has passed through said subject to obtain a radiographic image;
movement means for moving said subject so as to obtain radiographic images of said subject from many directions;
laminograph image restoration means for restoring a tomographic image of a desired plane from said radiographic images and from information defining a transmission direction of said radiation;
image magnification and reduction means for changing a magnification of at least one of said radiographic image and said tomographic image and for changing a magnification of a pattern showing a shape of said subject;
composite image preparation means for preparing a composite image composed of said pattern showing said shape of said subject with a changed magnification and one of said radiographic image and said tomographic images with a changed magnification in the same scale; and
display means for displaying said composite image and at least one of said radiographic image and said tomographic image.

31. The laminograph according to claim 30, further comprising:

indicator means for pointing to an optional position in said image displayed on said display means, for writing an information at said optional position and for indicating said position;
memory means for storing a coordinate in said pattern as an image directory; and
means for writing a fault assessment result at said pointed position on said composite image and for displaying said information of said fault assessment result on one of original images of said radiographic image and said tomographic image at said pointed position.

32. The laminograph according to claim 31, further comprising:
wipe means for reducing said composite image and for displaying said composite image thus reduced as a wipe image on displayed one of said original images of said radiographic image and said tomographic image at said pointed position;
whereby to display a position of said displayed one of said original images of said radiographic image and said tomographic image in said wipe image so as to distinguish a relation between said fault assessment result and said position.

33. The laminograph according to claim 30, further comprising:
information presentation means for presenting an information concerning a shape of said subject, positions of constituent parts of said subject, and locations to be inspected;
whereby said radiographic image being obtained at a position of said subject specified by said information.

34. An inspection and repair device, comprising:
a laminograph including,
an X-ray radiation source for generating radiation towards a subject,
radiation detection means with a two-dimensional detecting area positioned opposite said X-ray radiation source for detecting said radiation from said X-ray radiation source which has passed through said subject to obtain a radiographic image,
movement means for moving said subject so as to obtain radiographic images of said subject from many directions,
laminograph image restoration means for restoring a tomographic image of a desired plane from said radiographic images and from information defining a transmission direction of said radiation,
image magnification and reduction means for changing a magnification of at least one of said radiographic image and said tomographic image and for changing a magnification of a pattern showing a shape of said subject,
composition image preparation means for preparing a composite image composed of said pattern showing said shape of said subject with a changed magnification and one of said radiographic image and said tomographic image with a changed magnification in the same scale, and
display means for displaying said composite image and at least one of said radiographic image and said tomographic image;
communication and control means for communicating an inspection result, said images and a repair result to said laminograph and for controlling said inspection result and said repair result;

display input means for displaying said inspection result and said images and for inputting said repair result; and means for returning said subject repaired to an inspection process to re-inspect an part which has been repaired of said subject.

35. The inspection and repair device according to claim 34, further comprising:

locating means for locating said subject in a specified position;

position display means for optically charcterising said specified position on said subject; and control means for controlling said locating means and said position display means, whereby to display a fault position of said subject repaired on said composite image on said subject repaired.

36. The inspection and repair device according to claim 35:

wherein said position display means changes its optical characteristic according to a type of fault and displays said characteristic on said subject.

37. The inspection and repair device according to claim 34, further comprising:

information presentation means for presenting an information concerning a shape of said subject, positions of constituent parts of said subject, and locations to be inspected;

whereby said radiographic image being obtained at a position of said subject specified by said information.

38. A laminograph, comprising:

an X-ray radiation source for generating radiation towards a subject;

radiation surface sensor means, with a two-dimensional resolution, fitted opposite to said X-ray radiation source for detecting said radiation from said radiation source which has passed through said subject;

scanning means for moving said subject to take a plurality of different positions between said X-ray radiation source and said radiation surface sensor means and for scanning said subject in each of said different positions by said radiation from said X-ray radiation source;

data collection means for collection a plurality of outputs of said radiation surface sensor means during said scanning by said scanning means to obtain a plurality of radiographic images of said subject in said different positions;

position measurement means for measuring multiple positions of a focal plane at multiple places of said subject;

displacement measurement means for measuring multiple displacements based on said multiple positions of said focal plane measured by said position measurement means;

image pre-processing means for processing one of enhancing, weakening and deleting characteristics of said radiographic images to obtain pre-processed radiographic images; and image processing means for displacing said plurality of radiographic images in relation to the multiple displacements measured by said displacement measuring means and for adding and averaging said plurality of displaced radiographic images to obtain a radiographic image of said subject focused on said focal plane as a tomographic image of said subject.

* * * * *